US012730109B2

(12) United States Patent
Drake et al.

(10) Patent No.: US 12,730,109 B2
(45) Date of Patent: Sep. 8, 2026

(54) TARGETED SIALIC ACID LABELING COMPOUNDS, METHODS, AND USES THEREOF

(71) Applicant: MUSC FOUNDATION FOR RESEARCH DEVELOPMENT, Charleston, SC (US)

(72) Inventors: Richard R. Drake, Charleston, SC (US); Xiaowei Lu, Charleston, SC (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 645 days.

(21) Appl. No.: 17/231,813

(22) Filed: Apr. 15, 2021

(65) Prior Publication Data

US 2021/0325398 A1 Oct. 21, 2021

Related U.S. Application Data

(60) Provisional application No. 63/010,499, filed on Apr. 15, 2020.

(51) Int. Cl.
*G01N 33/58* (2006.01)

(52) U.S. Cl.
CPC .................................... *G01N 33/58* (2013.01)

(58) Field of Classification Search
CPC . G01N 33/58; G01N 2400/00; G01N 2560/00
See application file for complete search history.

(56) References Cited

PUBLICATIONS

Kumar et al., "Sialyltransferase inhibitors: consideration of molecular shape and charge/hydrophobic interactions", Carbohydrate Research, vol. 378, pp. 45-55, published Jan. 10, 2013. (Year: 2013).*
Hanson et al., "Tailored glycoproteomics and glycan site mapping using saccharide-selective bioorthogonal probes", J. Am. Chem. Soc., vol. 129(23), 7266-7267, published Jun. 13, 2007, cited passages are on pp. 1-6. (Year: 2007).*
Qasba et al., "Site-Specific Linking of Biomolecules via Glycan Residues Using Glycosyltransferases", Biotechnol. Prog., 2008, vol. 24, No. 3, pp. 520-526. (Year: 2008).*
Alley, Jr., et al., "Glycomic Analysis of Sialic Acid Linkages in Glycans Derived from Blood Serum Glycoproteins," Journal of Proteome Research 2010, 9, 3062-3072.
Angel, et al., "MALDI Imaging Mass Spectrometry of N-glycans and Tryptic Peptides from the Same Formalin-Fixed, Paraffin-Embedded Tissue Section," Methods Mol Biol. 2018 ; 1788: 225-241. doi:10.1007/7651_2017_81.
Angel, et al., "Mapping Extracellular Matrix Proteins in Formalin-Fixed, Paraffin-Embedded Tissues by MALDI Imaging Mass Spectrometry," J. Proteome Res. 2018, 17, 635-646.
Bertozzi, C., "A Decade of Bioorthogonal Chemistry," Accounts of Chemical Research, vol. 44, No. 9, 2011, 651-653.
Bézay, et al., "Chemoenzymatic-Chemical Synthesis of a (2-3)-Sialyl T Threonine Building Block and Its Application to the Synthesis of the N-Terminal Sequence of Leukemia-Associated Leukosialin (CD 43)," Angew. Chem. Int. Ed. 2001, 40, No. 12.
Bond, et al., "Photocrosslinking of glycoconjugates using metabolically incorporated diazirine-containing sugars," Nature Protocols, vol. 4, No. 7, 2009, all enclosed pages cited.
Borcard, et al., "Covalent Cell Surface Functionalization of Human Fetal Osteoblasts for Tissue Engineering," dx.doi.org/10.1021/bc200147m, Bioconjugate Chem. 2011, 22, 1422-1432.
Charter, et al., "Biosynthetic incorporation of unnatural sialic acids into polysialic acid on neural cells," Glycobiology, vol. 10, No. 10, 2000, pp. 1049-1056.
Danishefsky, et al., "Azaglycosylation of Complex Stannyl Alkoxides with Glycal-Derived Iodo Sulfonamides: A Straightforward Synthesis of Sialyl-Lewis X Antigen and Other Oligosaccharide Domains," J. Am. Chem. Soc. 1992, 114, 8331-8333.
De Haan, et al., "Linkage-Specific Sialic Acid Derivatization for MALDI-TOF-MS Profiling of IgG Glycopeptides," DOI: 10.1021/acs.analchem.5b02426 Anal. Chem. 2015, 87, 8284-8291.
Devaraj, N., "The Future of Bioorthogonal Chemistry," ACS Cent. Sci. 2018, 4, 952-959.
Du, et al., "Metabolic glycoengineering: Sialic acid and beyond," Glycobiology vol. 19 No. 12 pp. 1382-1401, 2009 doi:10.1093/glycob/cwp115.
Endo, et al., "Fluorescent labeling of a carboxyl group of sialic acid for MALDI-MS analysis of sialyloligosaccharides and ganglioside," Biochemical and Biophysical Research Communications 378 (2009) 890-894.
Feng, et al., "Bifunctional Unnatural Sialic Acids for Dual Metabolic Labeling of Cell-Surface Sialylated Glycans," dx.doi.org/10.1021/ja402326z | J. Am. Chem. Soc. 2013, 135, 9244-9247.
Flaherty, et al., "2D Nmr Analysis of the polylactone derivative of colominic acid. Complete IH and 13C NMR chemical shift assignments," Carbohydrate Research 281 (1996) 173-177.
Gervay, et al., "Ring Opening of Sialyllactones with Glycine Esters: Synthesis of Selectively Protected Glycinyl-NeuAc Saccharopeptides," Tetrahedron, vol. 53, No. 32, pp. 11039-11048, 1997.
Gervay, et al., "An Unexpected Sialylation: Total Syntheses of Gm* and a Positional Isomer," J. Org. Chem. 1993,58, 5465-5468.
Han, et al., "Homomultimeric complexes of CD22 in B cells revealed by protein-glycan cross-linking," Nature Chemical Biology, vol. 1, No. 2, Jul. 2005, all enclosed pages cited.
Hanamatsu, et al., "Sialic Acid Linkage Specific Derivatization of Glycosphingolipid Glycans by Ring-Opening Aminolysis of Lactones," Anal. Chem. 2018, 90, 13193-13199.
Harvey, et al., "Application of negative ion MS/MS to the identification of N-glycans released from carcinoembryonic antigen cell adhesion molecule 1 (CEACAM1)," J. Mass. Spectrom. 2009, 44, 50-60.

(Continued)

*Primary Examiner* — Shafiqul Haq
(74) *Attorney, Agent, or Firm* — Carin R. Miller; Lex Generalis, LLC

(57) ABSTRACT

Described herein are compounds, compositions, and reagents capable of labeling a biomolecule. In some embodiments, the compounds, compositions, and reagents allow for labeling to occur using a bioorthagonal reaction outside of a living cell and without a glycosyltransferase enzyme. Also described herein are methods of using the compounds compositions and reagents described herein.

18 Claims, 10 Drawing Sheets

(56) References Cited

PUBLICATIONS

Harvey, et al., "Structural and quantitative analysis of N-linked glycans by matrix-assisted laser desorption ionization and negative ion nanospray mass spectrometry," Analytical Biochemistry 376 (2008) 44-60.
Holst, et al., "Linkage-Specific in Situ Sialic Acid Derivatization for N-Glycan Mass Spectrometry Imaging of Formalin-Fixed Paraffin-Embedded Tissues," Anal. Chem. 2016, 88, 5904-5913.
Hsu, et al., "Alkynyl sugar analogs for the labeling and visualization of glycoconjugates in cells," PNAS, Feb. 20, 2007, vol. 104, No. 8, 2614-2619.
Jacobs, et al., "Substrate Specificity of the Sialic Acid Biosynthetic Pathway," Biochemistry 2001, 40, 12864-12874.
Jiang, et al., "Sialic acid linkage-specific permethylation for improved profiling of protein glycosylation by MALDI-TOF MS," Analytica Chimica Acta 981 (2017) 53-61.
Kawashima, et al., "Efficient extraction of proteins from formalin-fixed paraffin-embedded tissues requires higher concentration of tris(hydroxymethyl)aminomethane," Clinical Proteomics 2014, 11:4, all enclosed pages cited.
Kayser, et al., "Biosynthesis of a Nonphysiological Sialic Acid in Different Rat Organs, Using N-Propanoyl-D-hexosamines as Precursors," The Journal of Biological Chemistry, 1992, vol. 267, No. 24, Issue of Aug. 25, pp. 16934-16938.
Kim, et al., "Characterization of the Metabolic Flux and Apoptotic Effects of O-Hydroxyl- and N-Acyl-modified N-Acetylmannosamine Analogs in Jurkat Cells," The Journal of Biological Chemistry, vol. 279, No. 18, Issue of Apr. 30, pp. 18342-18352, 2004.
Lageveen-Kammeijer, et al., "Highly sensitive CE-ESI-MS analysis of N-glycans from complex biological samples," Nature Communications, (2019) 10:2137, https://doi.org/10.1038/s41467-019-09910-7.
Laughlin, et al., "Imaging the glycome," PNAS, vol. 106, No. 1, Jan. 6, 2009, all enclosed pages cited.
Li, et al., "MALDI-MS analysis of sialylated N-glycan linkage isomers using solid-phase two step derivatization method," Analytica Chimica Acta 924 (2016) 77-85.
Lifely, et al., "Sialic Acid Polysaccharide Antigens of Neisseria Meningitidis and *Escherichia coli*: esterification between adjacent residues," Carbohydrate Research, 94 (1981), 193-203.
Luchansky, et al., "Expanding the Diversity of Unnatural Cell-Surface Sialic Acids," ChemBioChem 2004, 5, 371-374, DOI: 10.1002/cbic.200300789.
Mahal, et al., "Engineering Chemical Reactivity on Cell Surfaces Through Oligosaccharide Biosynthesis," Science, vol. 276, May 16, 1997, all enclosed pages cited.
Mahal, et al., "A Small-Molecule Modulator of Poly-a2,8-Sialic Acid Expression on Cultured Neurons and Tumor Cells," Science, vol. 294, Oct. 12, 2001, all enclosed pages cited.
McDowell, et al., "Imaging Mass Spectrometry and Lectin Analysis of N-Linked Glycans in Carbohydrate Antigen-Defined Pancreatic Cancer Tissues," Mol Cell Proteomics (2021) 20, all enclosed pages cited.
Meng, et al., "Regioselective Chemoenzymatic Synthesis of Ganglioside Disialyl Tetrasaccharide Epitopes," J. Am. Chem. Soc. 2014, 136, 5205-5208.
Nishikaze, et al., "Differentiation of Sialyl Linkage Isomers by One-Pot Sialic Acid Derivatization for Mass Spectrometry-Based Glycan Profiling," Anal. Chem. 2017, 89, 2353-2360.
Nishikaze, et al., "Sialic acid derivatization for glycan analysis by mass spectrometry," Proc. Jpn. Acad., Ser. B 95, No. 9, (2019), all enclosed pages cited.
Palaniappan, et al., "Chemical Glycoproteomics," Chem. Rev. 2016, 116, 14277-14306.
Parsons, et al., "Optimal Synthetic Glycosylation of a Therapeutic Antibody," Angew. Chem. Int. Ed. 2016, 55, 2361-2367.
Pongracz, et al., "Expanding the Reaction Space of Linkage-Specific Sialic Acid Derivatization," Molecules 2019, 24, 3617; doi:10.3390/molecules24193617, all enclosed pages cited.
Powers, et al., "MALDI Imaging Mass Spectrometry Profiling of N-Glycans in Formalin-Fixed Paraffin Embedded Clinical Tissue Blocks and Tissue Microarrays," PLOS One, vol. 9, Issue 9, Sep. 2014, all enclosed pages cited.
Presolski, et al., "Copper-Catalyzed Azide-Alkyne Click Chemistry for Bioconjugation," Curr Protoc Chem Biol. 2011 ; 3(4): 153-162. doi:10.1002/9780470559277.ch110148.
Pudelko, et al., "Formation of lactones from sialylated MUC1 glycopeptides," Org. Biomol. Chem., 2006, 4, 713-720.
Reiding, et al., "High-Throughput Profiling of Protein N-Glycosylation by MALDITOF-MS Employing Linkage-Specific Sialic Acid Esterification," dx.doi.org/10.1021/ac500335t | Anal. Chem. 2014, 86, 5784-5793.
Ruhaak, et al., "Mass Spectrometry Approaches to Glycomic and Glycoproteomic Analyses," Chem. Rev. 2018, 118, 7886-7930.
Sakamoto, et al., "Chemoselective glycosidation strategy based on glycosyl donors and acceptors carrying phosphorus-containing leaving groups: a convergent synthesis of ganglioside GM," Tetrahedron Letters 41 (2000) 7691-7695.
Saludes, et al., "Synthesis and Structural Characterization of Sialic Acid-Glutamic Acid Hybrid Foldamers as Conformational Surrogates of r-2,8-Linked Polysialic Acid," J. Am. Chem. Soc. 2009, 131, 5495-5505.
Saxon, et al., "Cell Surface Engineering by a Modibed Staudinger Reaction," Science, vol. 287, Mar. 17, 2000, all enclosed pages cited.
Saxon, et al., "Investigating Cellular Metabolism of Synthetic Azidosugars with the Staudinger Ligation," J. Am. Chem. Soc. 2002, 124, 14893-14902.
Sekiya, et al., "Derivatization for Stabilizing Sialic Acids in MALDI-MS," Analytical Chemistry, vol. 77, No. 15, Aug. 1, 2005 10.1021/ac0502870.
Shariatgorji, et al., "Comprehensive mapping of neurotransmitter networks by MALDI-MS imaging," Nature Methods, vol. 16, Oct. 2019, 1021-1028.
Sletten, et al., "Bioorthogonal Chemistry: Fishing for Selectivity in a Sea of Functionality," Angew. Chem. Int. Ed. 2009, 48, 6974-6998.
Su, et al., "Synthesis of New Polysialic Acid Derivatives," Macromol. Biosci. 2010, 10, 1028-1033.
Tan, et al., "Toward Homogeneous Erythropoietin: Non-NCL-Based Chemical Synthesis of the Gln78-Arg166 Glycopeptide Domain," J. Am. Chem. Soc., 2009, 131, 5424-5431.
Tanaka, et al., "Photoactivatable Crosslinking Sugars for Capturing Glycoprotein Interactions," J. Am. Chem. Soc. 2008, 130, 3278-3279.
Toyoda, et al., Quantitative Derivatization of Sialic Acids for the Detection of Sialoglycans by MALDI MS, Analytical Chemistry, vol. 80, No. 13, Jul. 1, 2008.
Varki, et al., "Chapter 14 Sialic Acids," Essentials of Glycobiology. 2nd edition. Cold Spring Harbor (NY): Cold SpringHarbor Laboratory Press; 2009.
Viswanathan, et al., "Engineering Sialic Acid Synthetic Ability into Insect Cells: Identifying Metabolic Bottlenecks and Devising Strategies to Overcome Them," Biochemistry 2003, 42, 15215-15225.
Wen, et al., "Two-Step Chemoenzymatic Detection of N-Acetylneuraminic Acid-α(2-3)-Galactose Glycans," J. Am. Chem. Soc. 2016, 138, 11473-11476.
Wen, et al., "A One-Step Chemoenzymatic Labeling Strategy for Probing Sialylated Thomsen-Friedenreich Antigen," ACS Cent. Sci. 2018, 4, 451-457.
Wheeler, et al., "Derivatization of sialic acids for stabilization in matrix-assisted laser desorption/ionization mass spectrometry and concomitant differentiation of a(2-3)- and a(2-6)-isomers," Rapid Commun. Mass Spectrom. 2009; 23: 303-312.
Wollscheid, et al., "Mass spectrometric identification and relative quantification of N-linked cell surface glycoproteins," Nature Biotechnology, vol. 27, No. 4, Apr. 2009, all enclosed pages cited.

(56) References Cited

PUBLICATIONS

Wratil, et al., "Metabolic Glycoengineering with N-Acyl Side Chain Modified Mannosamines," Angew. Chem. Int. Ed. 2016, 55, 9482-9512.
Wu, et al., "Mature homogeneous erythropoietin building blocks by chemical synthesis: the EPO 22-37 glycopeptide domain presenting the full N-linked dodecasaccharide," Tetrahedron Letters 47 (2006) 8009-8011.
Xie, et al., "Cell-Selective Metabolic Glycan Labeling Based on Ligand-Targeted Liposomes," J. Am. Chem. Soc. 2012, 134, 9914-9917.
Yang, et al., "Solid-Phase Chemical Modification for Sialic Acid Linkage Analysis: Application to Glycoproteins of Host Cells Used in Influenza Virus Propagation," Anal. Chem. 2017, 89, 9508-9517.
Yang, et al., "Identification of Sialic Acid Linkages on Intact Glycopeptides via Differential Chemical Modification Using IntactGIG-HILIC," J. Am. Soc. Mass Spectrom. (2018) 29:1273Y1283.
Yarema, et al., "A photochemical snapshot of CD22 binding," Nature Chemical Biology, vol. 1, No. 2 Jul. 2005, all enclosed pages cited.
Zeng, et al., "High-efficiency labeling of sialylated glycoproteins on living cells," Nature Methods, vol. 6, No. 3, Mar. 2009, all enclosed pages cited.
Zhou, et al.,"Biological Functions and Analytical Strategies of Sialic Acids in Tumor," Cells 2020, 9, 273; doi:10.3390/cells9020273, all enclosed pages cited.

* cited by examiner

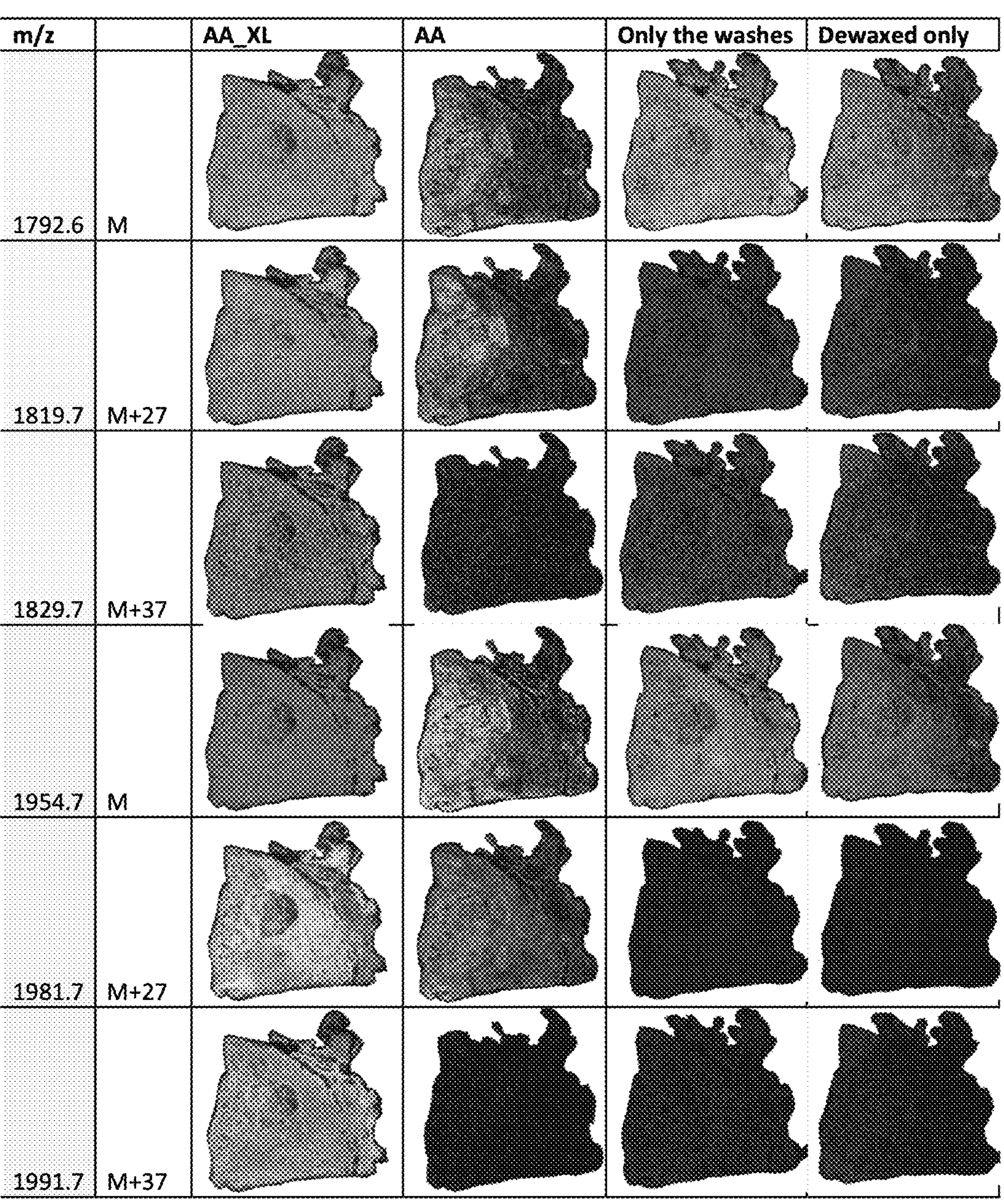
FIG. 2 (cntd.)

| m/z | | AA_XL | AA | Only the washes | Dewaxed only |
|---|---|---|---|---|---|
| 2100.7 | M | 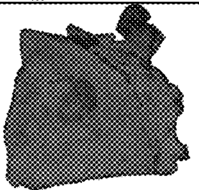 | 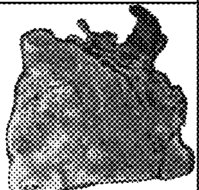 | 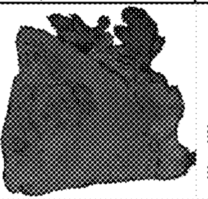 | 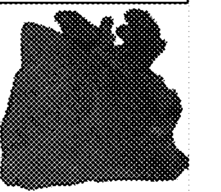 |
| 2127.8 | M+27 | 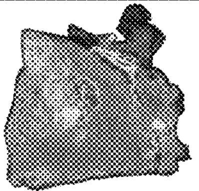 | 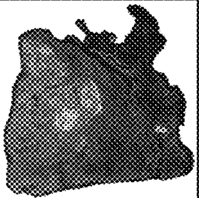 | 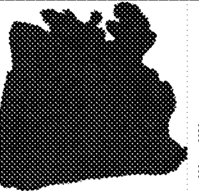 | 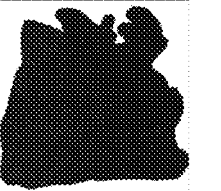 |
| 2137.8 | M+37 | 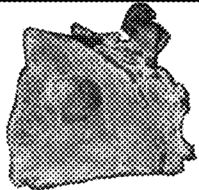 | 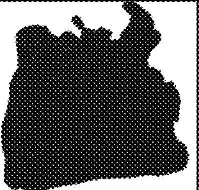 | 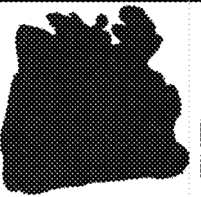 | 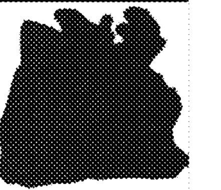 |
| 2272.8 | M+27 | 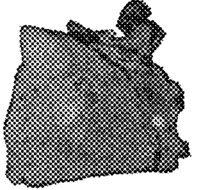 | 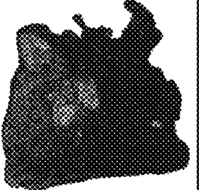 | 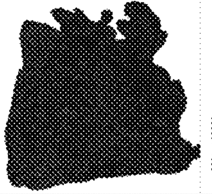 | 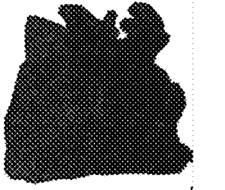 |
| 2294.8 | M+Na +27 | 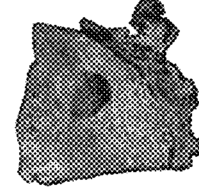 | 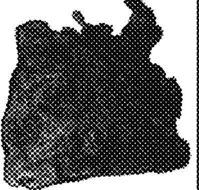 | 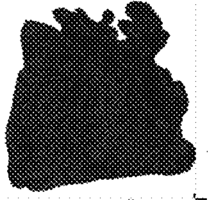 | 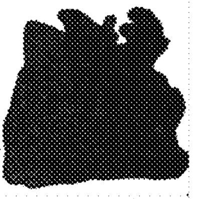 |
| 2299.9 | M+27 *2 | 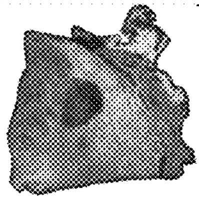 | 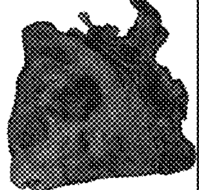 | 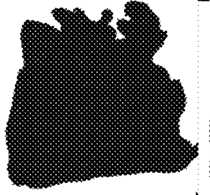 | 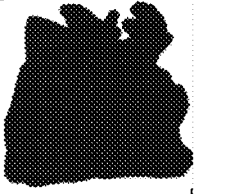 |
FIG. 2 (cntd.)

| m/z | | AA_XL | AA | Only the washes | Dewaxed only |
|---|---|---|---|---|---|
| 2418.9 | M+27 | 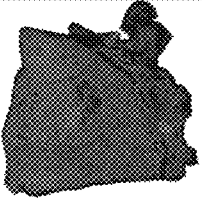 | 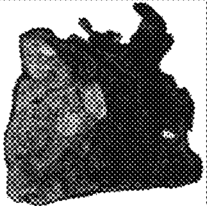 | 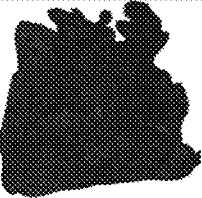 | 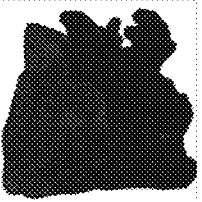 |
| 2440.9 | M+Na +27 | 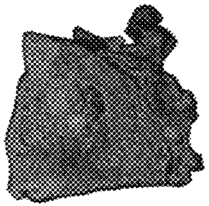 | 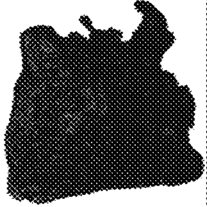 | 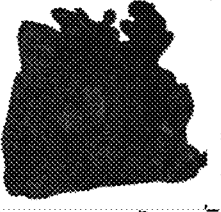 | 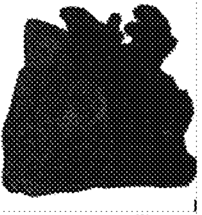 |
| 2428.9 | M+37 | 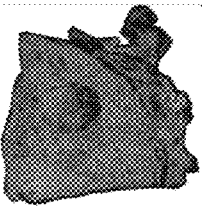 | 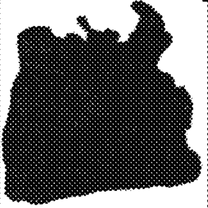 | 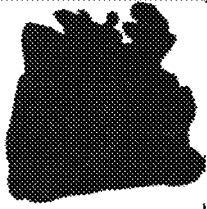 | 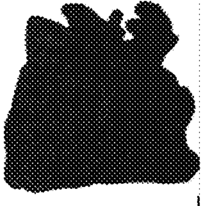 |
| 2450.8 | M+Na +37 | 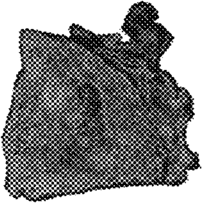 | 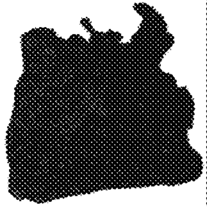 | 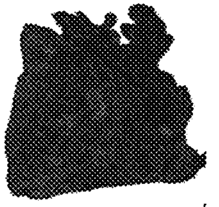 | 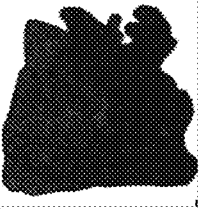 |
| 2168.8 | M+27 | 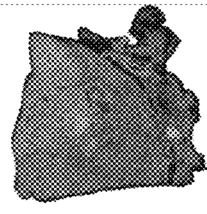 | 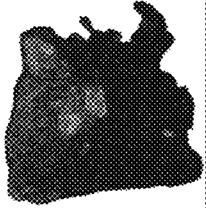 | 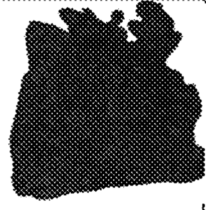 | 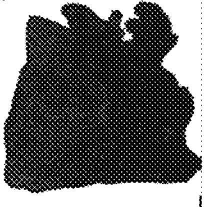 |
| 2178.8 | M+37 | 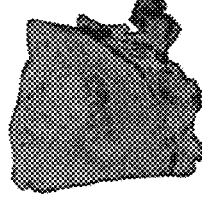 | 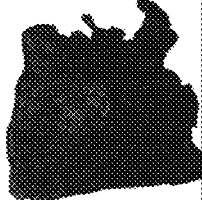 | 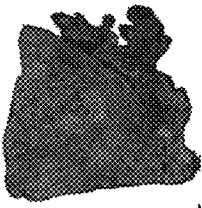 | 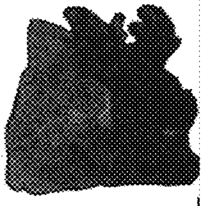 |
FIG. 2 (cntd.)

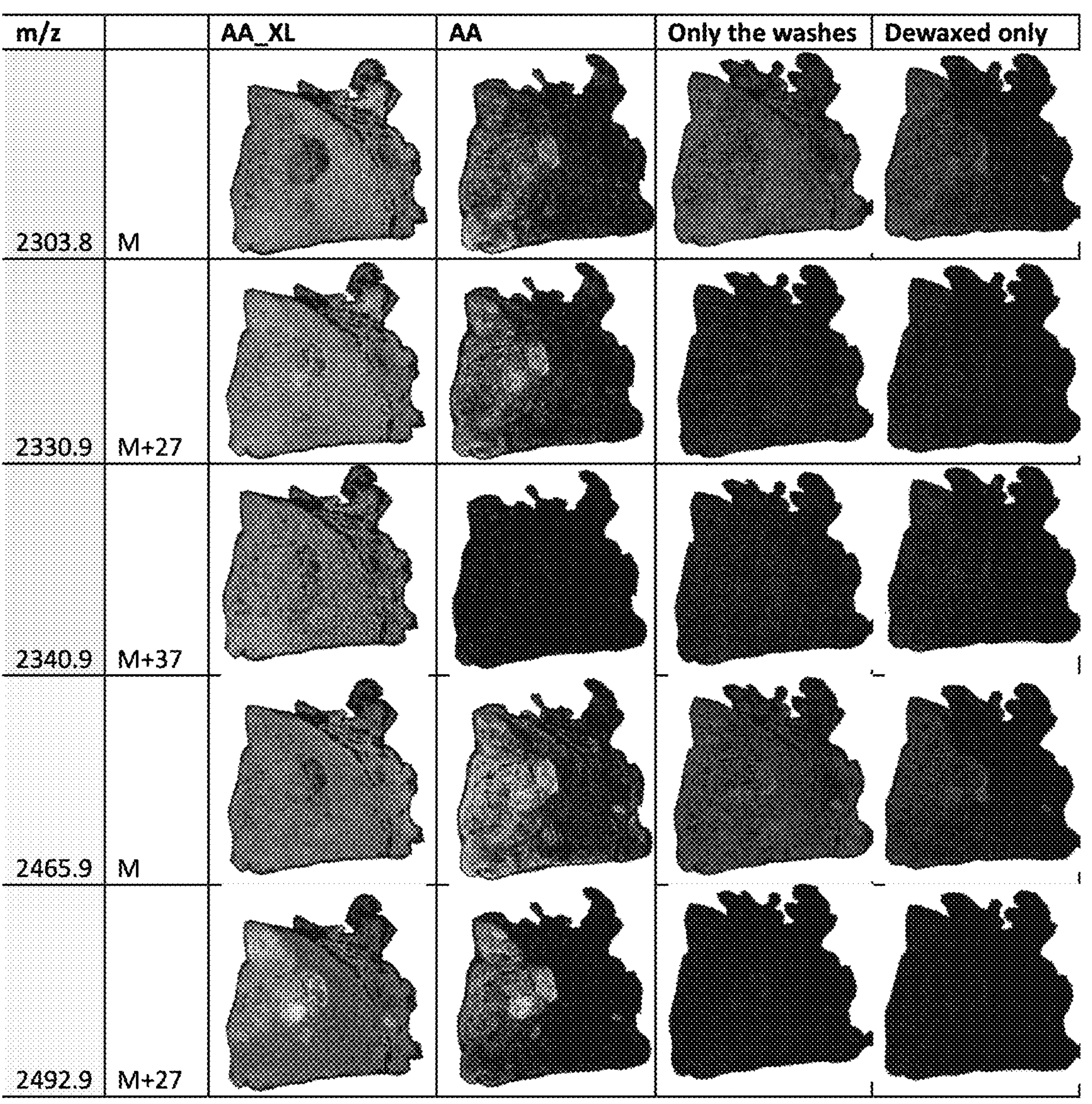
FIG. 2 (cntd.)

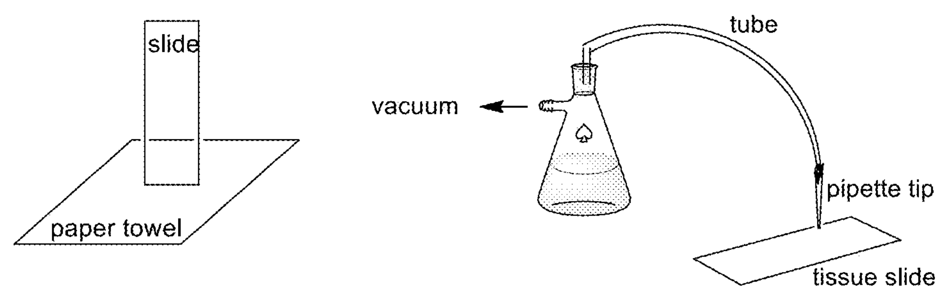
FIG. 4A
FIG. 4B
| 1 | 2 | 3 | 4 |
|---|---|---|---|
| Seeblue ladder | Mixture 20 | Mixture 19 | biotin-AAL |
| 5 ul | 0.83 ug | 0.83 ug | 0.83 ug |
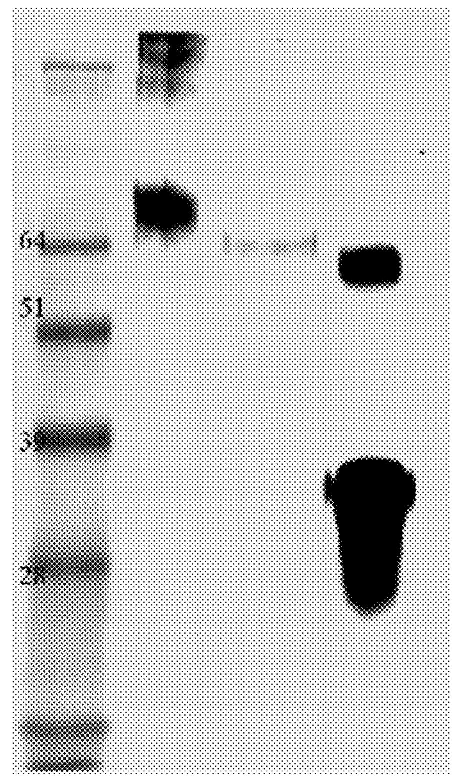
FIG. 5

| | dewax | HIER (pH3) | Sialidase treatment | AA_N3 | CuAAC (biotin-alkyne) | Protein extraction |
|---|---|---|---|---|---|---|
| A | + | - | - | + | catalyst + | + |
| B | + | - | - | + | catalyst - | + |
| C | + | + | + | + | catalyst + | + |
| D | + | - | - | - | - | + |

TARGETED SIALIC ACID LABELING COMPOUNDS, METHODS, AND USES THEREOF

CROSS-REFERENCE TO RELATED APPLICATIONS

This application claims the benefit of and priority to U.S. Provisional Patent Application No. 63/010,499, filed on Apr. 15, 2020, entitled "TARGETED SIALIC ACID LABELING COMPOUNDS, METHODS, AND USES THEREOF," the contents of which is incorporated by reference herein in its entirety.

TECHNICAL FIELD

The subject matter disclosed herein is generally directed to bioorthagonal chemistry.

BACKGROUND

Bioorthagonal reactions have found widespread use in applications ranging from glycan engineering to in vivo imaging. Researchers have devised numerous reactions that can be predictably performed in a biological setting. Despite there being a plethora of bioorthagonal reaction schemes and reagents available, there still exists a need for new reactions, reagents, and/or methods that can improve, for example, the efficiency, the specificity, and/or the application of bioorthagonal reactions.

Citation or identification of any document in this application is not an admission that such a document is available as prior art to the present invention.

SUMMARY

In certain example embodiments, described herein are methods of selectively modifying a linked sialic acid or polysialic acid comprising exposing a 2,3 linked sialic acid and/or a 2,8 linked polysialic acid to one or more condensing reagents (e.g. EDC, HOBt) under suitable reaction conditions to form a lactone at the 2,3 and/or 2,8 linkages; and exposing the lactone to a bi-functional linker with a primary amine the second functionality under suitable reaction conditions to selectively modify the linked sialic acid and/or polysialic acid with the second functionality.

In certain example embodiments, the method further comprises exposing the selectively modified sialic acid and/or polysialic acid with a reactive cargo molecule whereby the reactive cargo molecule reacts with the second functionality on the modified sialic acid or polysialic acid to selectively attach a cargo molecule the linked sialic acid or polysialic acid.

In certain example embodiments, the bi-functional linker is or comprises a propargyl amine or an azido amine, whereby the resulting selectively modified sialic acid and/or polysialic acid is modified to contain a reactive alkyne and/or a reactive azide.

In certain example embodiments, the linked sialic acid and/or polysialic acid is attached to or otherwise incorporated with a biological molecule.

In certain example embodiments, the linked sialic acid and/or polysialic acid is attached to or otherwise incorporated with a biological molecule before exposing to the condensing reagent(s) (e.g., EDC, HOBt) and/or exposing the lactone, and/or exposing the selectively modified sialic acid and/or polysialic acid, or a combination thereof.

In certain example embodiments, the linked sialic acid and/or polysialic acid is attached to or otherwise incorporated with a biological molecule after exposing to the condensing reagent(s) (e.g., EDC, HOBt) and/or exposing the lactone, and/or exposing the selectively modified sialic acid and/or polysialic acid, or a combination thereof.

In certain example embodiments, the biologic molecule is a protein.

In certain example embodiments, the protein is an antibody.

In certain example embodiments, the biologic molecule is integrated into or is otherwise part of or coupled to one or more components of a cell.

In certain example embodiments, the biologic molecule is integrated into or is otherwise part of or coupled to one or more components of a micelle, exosome, or other vesicle.

In certain example embodiments, the reactive cargo molecule is a mass spectrometry matrix molecule.

In certain example embodiments, one or more of the steps is performed in vitro, ex vivo or in situ.

In certain example embodiments, the protein or biologic molecule is integrated into or is otherwise part of or coupled to one or more components of a cell.

In certain example embodiments, described herein are mass spectrometry labeling reagents as prepared by any of the methods of described herein to produce a selectively labeled 2,3 linked sialic acid or 2,8 linked polysialic acid.

In certain example embodiments, described herein are cargo delivery agents as prepared by any of the methods of described herein to produce a selectively labeled 2,3 linked sialic acid or 2,8 linked polysialic acid.

In certain example embodiments, described herein are imaging agents as prepared by any of the methods of described herein to produce a selectively labeled 2,3 linked sialic acid or 2,8 linked polysialic acid.

In certain example embodiments, described herein are kits containing a mass spectrometry labeling reagent as described herein, a cargo delivery agent as described herein, an imaging agent as described herein or a combination thereof.

In certain example embodiments, described herein are methods of specifically imaging a tissue and/or one or more cells or component thereof comprising performing a method herein to produce a selectively labeled 2,3 linked sialic acid or 2,8 linked polysialic acid; and imaging the one or more cells or component thereof.

In certain example embodiments, the tissue and/or one or more cells or component thereof are fixed in formalin.

Described in certain example embodiments herein are assays comprising exposing a cell or cell population, a tissue, or the component thereof to a selectively modified linked sialic acid or polysialic acid, wherein the sialic acid or poly sialic acid is selectively modified at the 2 position of the linked sialic acid or the polysialic acid, wherein the polysialic acid is 2,3 linked, 2,6 linked, or a 2,8 linked, and wherein the selectively modified linked sialic acid or polysialic acid is selectively modified to comprise a cargo molecule; and detecting, quantifying, or both one or more characteristics of the cell or cell population, tissue, or component thereof.

In certain example embodiments, the assay further comprises selectively modifying a linked sialic acid or polysialic acid, wherein selectively modifying comprises exposing a 2,3 linked, a 2,6 linked, or a 2,8 linked sialic acid or polysialic acid to a condensing reagent under suitable reaction conditions to form a lactone at the 2,3, 2,6 or 2,8 linkages; and exposing the lactone to a bi-functional linker with a primary amine under suitable reaction conditions to selectively modify the linked sialic acid or polysialic acid with a functionality on the bi-functional linker thereby selectively modifying the linked sialic acid or polysialic acid with the bi-functional linker at the 2 position of the linked sialic acid or polysialic acid.

In certain example embodiments, the assay further comprises selectively attaching a cargo molecule to the selectively modified linked sialic or polysialic acid by exposing the selectively modified linked sialic acid or polysialic acid with a reactive cargo molecule whereby the reactive cargo molecule reacts with an available reactive functionality on the bi-functional linker to selectively attach the cargo molecule the linked sialic acid or polysialic acid.

In certain example embodiments, the bi-functional linker is or comprises a propargyl amine or an azide amine, whereby the resulting selectively modified linked sialic acid or polysialic acid is modified to contain a reactive alkyne, a reactive azide, or both.

In certain example embodiments, the linked sialic acid or polysialic acid is attached to or is otherwise incorporated with a biological molecule.

In certain example embodiments, the linked sialic acid or polysialic acid is attached to or otherwise incorporated with a biological molecule before exposing to the condensing reagent, exposing the lactone, exposing the selectively modified linked sialic acid or polysialic acid, or a combination thereof.

In certain example embodiments, the linked sialic acid or polysialic acid is attached to or otherwise incorporated with a biological molecule after exposing to a dimethyl amine, exposing the lactone, exposing the selectively modified linked sialic acid or polysialic acid, or a combination thereof.

In certain example embodiments, the biologic molecule is a protein.

In certain example embodiments, the protein is an antibody.

In certain example embodiments, the biologic molecule is integrated into or is otherwise part of or coupled to one or more components of a cell.

In certain example embodiments, the biologic molecule is integrated into, is otherwise part of, or is coupled to one or more components of a micelle, exosome, or other vesicle.

In certain example embodiments, the cargo molecule is a mass spectrometry matrix molecule, an imaging agent, a therapeutic agent, a biologically active agent, or any combination thereof.

In certain example embodiments, exposing the cell or cell population, the tissue, or the component thereof in vitro, ex vivo, or in situ.

In certain example embodiments, the cell or cell population, the tissue, or the component thereof is/are fixed in formalin.

In certain example embodiments, the one or more characteristics of the cell or cell population, the tissue, or the component thereof detected, quantified, or both is gene expression, protein expression, metabolites, growth, protein modification, cell or tissues composition, and combinations thereof.

In certain example embodiments, detecting, quantifying, or both comprises mass spectrometry, a cell or tissue staining technique, an affinity detection technique, an immunodetection technique, sequencing, a cell or tissue imaging technique, or any combination thereof.

Described in certain example embodiments herein are methods of selectively modifying a linked sialic acid or polysialic acid comprising exposing a 2,3 linked sialic acid or a 2,8 linked polysialic acid to a condensing reagent under suitable reaction conditions to form a lactone at the 2,3 or 2,8 linkages; and exposing the lactone to a bi-functional linker with a primary amine under suitable reaction conditions to selectively modify the linked sialic acid or polysialic acid with a first reactive functionality on the bi-functional linker thereby selectively modifying the linked sialic acid or polysialic acid with the bi-functional linker at the 2 position.

In certain example embodiments, the method further comprises selectively attaching a cargo molecule to a selectively modified linked sialic acid or polysialic acid by exposing the selectively modified linked sialic acid or polysialic acid with a reactive cargo molecule whereby the reactive carbo molecule reacts with a second reactive functionality on the bi-functional linker thereby selectively attaching a cargo molecule to the linked sialic acid or polysialic acid.

In certain example embodiments, the cargo molecule is a mass spectrometry matrix molecule, an imaging agent, a therapeutic agent, a biologically active agent, or any combination thereof.

In certain example embodiments, the bi-functional linker is or comprises a propargyl amine or an azide amine, whereby the resulting selectively modified linked sialic acid or polysialic acid is modified to contain a reactive alkyne or a reactive azide.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIGS. 4A-4B show washes performed after the first step of AA_XL.

FIG. 5 shows a western blot analysis for mixture 20 and 19. 3'-BSA were subject to AA_XL and CuAAC with biotin azide as described in Scheme 2 to yield mixture 20. With the same protocol, 6'sialyllactose-BSA was converted to mixture 19. Gel (loaded with ladder, mixture 20, mixture 19 and biotin-AAL) was developed and transferred. Membrane was blotted with streptavidin-IR800 and scanned with LI-COR.

Figure 1:
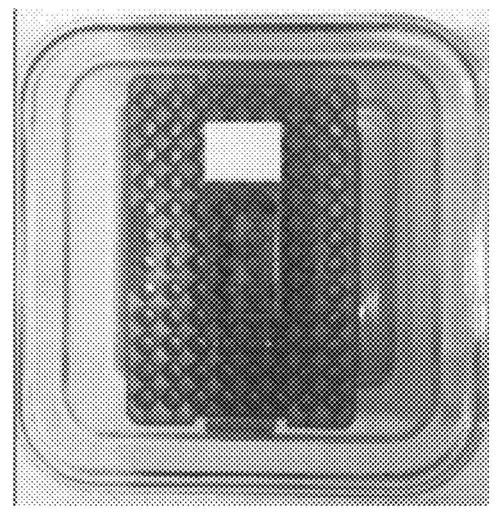
FIG. 1 shows an image of an exemplary humidity chamber for click reaction on FFPE slide.

The figures herein are for illustrative purposes only and are not necessarily drawn to scale.

DETAILED DESCRIPTION OF THE EXAMPLE EMBODIMENTS

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g., the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

Definitions of common terms and techniques in chemistry and organic chemistry can be found in Smith. Organic Synthesis, published by Academic Press. 2016; Tinoco et al. Physical Chemistry, $5^{th}$ edition (2013) published by Pearson; Brown et al., Chemistry, The Central Science $14^{th}$ ed. (2017), published by Pearson, Clayden et al., Organic Chemistry, $2^{nd}$ ed. 2012, published by Oxford University Press; Carey and Sunberg, Advanced Organic Chemistry, Part A: Structure and Mechanishms, $5^{th}$ ed. 2008, published by Springer; Carey and Sunberg, Advanced Organic Chemistry, Part B: Reactions and Synthesis, $5^{th}$ ed. 2010, published by Springer, and Vollhardt and Schore, Organic Chemistry, Structure and Function; $8^{th}$ ed. (2018) published by W. H. Freeman.

As used herein, the singular forms “a”, “an”, and “the” include both singular and plural referents unless the context clearly dictates otherwise.

As used herein, “about,” “approximately,” “substantially,” and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosed invention. As used herein, the terms “about,” “approximate,” “at or about,” and “substantially” can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is “about,” “approximate,” or “at or about” whether or not expressly stated to be such. It is understood that where “about,” “approximate,” or “at or about” is used before a quantitative value, the parameter also includes the specific quantitative value itself, unless specifically stated otherwise.

The term “optional” or “optionally” means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

As used herein, a “biological sample” may contain whole cells and/or live cells and/or cell debris. The biological sample may contain (or be derived from) a “bodily fluid”. The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms “subject,” “individual,” and “patient” are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured ex vivo or in vitro are also encompassed within the term “subject” and the like.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to “one embodiment”, “an embodiment,” “an example embodiment,” means that a particular feature, structure or characteristic described in connection with the embodiment is included in at least one embodiment of the present invention. Thus, appearances of the phrases “in one embodiment,” “in an embodiment,” or “an example embodiment” in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

As used herein, “antibody” can refer to a glycoprotein containing at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen. “Antibody” includes single valent, bivalent and multivalent antibodies.

As used herein, “polymer” refers to molecules made up of monomers repeat units that are linked together. “Polymers” are understood to include, but are not limited to, homopolymers, copolymers, such as for example, block, graft, random and alternating copolymers, terpolymers, etc. and blends and modifications thereof. “A polymer” can be a three-dimensional network (e.g. the repeat units are linked together left and right, front and back, up and down), a two-dimensional network (e.g. the repeat units are linked together left, right, up, and down in a sheet form), or a one-dimensional network (e.g. the repeat units are linked left and right to form a chain). "Polymers" can be composed, natural monomers or synthetic monomers and combinations thereof. The polymers can be biologic (e.g., the monomers are biologically important (e.g., an amino acid), natural, or synthetic.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-it interactions, polar π-interactions, and hydrophobic effects.

As used herein, "substituted," refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted. "Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-30 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

As used herein, "alkyl," refers to the radical of saturated aliphatic groups, including straight-chain alkyl, alkenyl, or alkynyl groups, branched-chain alkyl, cycloalkyl (alicyclic), alkyl substituted cycloalkylgroups, and cycloalkyl substituted alkyl. In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

As used herein, "alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —$CON(R)_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —$CF_3$, —$CH_2$—$CF_3$, —$CCl_3$); —CN; —$NCOCOCH_2CH_2$, —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), haloalkyls, —CN and the like. Cycloalkyls can be substituted in the same manner.

As used herein, "alkenyl" and "alkynyl" refer to unsaturated aliphatic groups analogous in length and possible substitution to the alkyls described above, but that contain at least one double or triple bond, respectively. The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof. The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

As used herein, "alkoxyl" or "alkoxy," "aroxy" or "aryloxy," generally describe compounds represented by the formula —OR', wherein $R^v$ includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl. The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto. The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

As used herein, "amino" and "amine," are art-recognized and refer to both substituted and unsubstituted amines, e.g., a moiety that can be represented by the general formula:

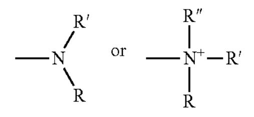

wherein, R, R', and R" each independently represent a hydrogen, substituted or unsubstituted alkyl, substituted or unsubstituted alkenyl, substituted or unsubstituted alkynyl, substituted or unsubstituted carbonyl, —$(CH_2)_m$—R'", or R and R' taken together with the N atom to which they are attached complete a heterocycle having from 3 to 14 atoms in the ring structure; R'" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' (and optionally R") each independently represent a hydrogen atom, substituted or unsubstituted alkyl, a substituted or unsubstituted alkenyl, or —$(CH_2)_m$—R'". Thus, the term 'alkylamine' as used herein refers to an amine group, as defined above, having a substituted or unsubstituted alkyl attached thereto (i.e., at least one of R, R', or R" is an alkyl group).

As used herein, "arylalkyl," refers to an alkyl group that is substituted with a substituted or unsubstituted aryl or heteroaryl group.

As used herein, "alkylaryl," refers to an aryl group (e.g., an aromatic or hetero aromatic group), substituted with a substituted or unsubstituted alkyl group.

As used interchangeably herein, the terms "amide" or "amido" refer to both "unsubstituted amido" and "substituted amido" and are represented by the general formula:

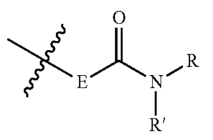

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $—(CH_2)_m—R'''$, or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' each independently represent a hydrogen atom, substituted or unsubstituted alkyl, a substituted or unsubstituted alkenyl, or $—(CH_2)_m—R'''$. When E is oxygen, a carbamate is formed. The carbamate cannot be attached to another chemical species, such as to form an oxygen-oxygen bond, or other unstable bonds, as understood by one of ordinary skill in the art.

As used herein, "arylthio" refers to —S-aryl or —S-heteroaryl groups, wherein aryl and heteroaryl are as defined herein. The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein. The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

As used herein, "aryl" refers to $C_5$-$C_{26}$-membered aromatic, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, for example, benzene, naphthalene, anthracene, phenanthrene, chrysene, pyrene, corannulene, coronene, etc. "Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, $—CH_2—CF_3$, $—CCl_3$), —CN, aryl, heteroaryl, and combinations thereof.

As used herein, "carbonyl," is art-recognized and includes such moieties as can be represented by the general formula:

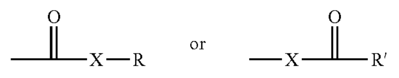

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $—(CH_2)_m—R''$, or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or $—(CH_2)_m—R''$; R'' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defined as above, the moiety is also referred to as a carboxyl group. When X is oxygen and R is hydrogen, the formula represents a 'carboxylic acid'. Where X is oxygen and R' is hydrogen, the formula represents a 'formate'. Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

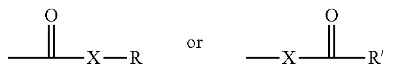

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "carboxyl" is as defined above for the formula

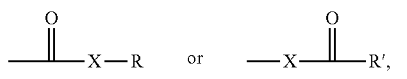

and is defined more specifically by the formula $—R^{iv}COOH$, wherein $R^{iv}$ is an alkyl, alkenyl, alkynyl, cycloalkyl, heterocyclyl, alkylaryl, arylalkyl, aryl, or heteroaryl. In preferred embodiments, a straight chain or branched chain alkyl, alkenyl, and alkynyl have 30 or fewer carbon atoms in its backbone (e.g., $C_1$-$C_{30}$ for straight chain alkyl, $C_3$-$C_{30}$ for branched chain alkyl, $C_2$-$C_{30}$ for straight chain alkenyl and alkynyl, $C_3$-$C_{30}$ for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure. The term "substituted carboxyl" refers to a carboxyl, as defined above, wherein one or more hydrogen atoms in R are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

As used herein, "administering" refers to the act of delivering a substance to a subject by any suitable methods, techniques, or routes. Administration routes, can include, but are not limited to, auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intraci sternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratym panic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease or condition to be treated/prevented, one or more characteristics of the subject, the compositions/substance being delivered, or a combination thereof. One of ordinary skill in the art, unless otherwise noted herein, will appreciate such parameters and be capable of determine a suitable delivery technique and route.

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups.

As used interchangeably herein, "heterocycle," "heterocyclic" and "heterocyclyl" refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

As used herein, "heteroaryl" refers to $C_5$-$C_{26}$-membered aromatic, fused aromatic, biaromatic ring systems, or combinations thereof, in which one or more carbon atoms on one or more aromatic ring structures have been substituted with an heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined for "substituted heteroaryl". The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, $-CH_2-CF_3$, $-CCl_3$), —CN, aryl, heteroaryl, and combinations thereof.

As used herein, "heteroalkyl," refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

The term "phenyl" is art recognized, and refers to the aromatic moiety $-C_6H_5$, i.e., a benzene ring without one hydrogen atom. The term "substituted phenyl" refers to a phenyl group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenoxy" is art recognized, and refers to a compound of the formula —OR' wherein $R^v$ is (i.e., —O—$C_6H_5$). One of skill in the art recognizes that a phenoxy is a species of the aroxy genus. The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenylthio" is art recognized, and refers to —S—$C_6H_5$, i.e., a phenyl group attached to a sulfur atom. The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phosphonyl" is represented by the formula

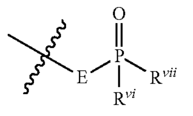

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, R" and R'" are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R", or R and R' taken together with the P atom to which they are attached complete a heterocycle having from 3 to 14 atoms in the ring structure; R'" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. The term "substituted phosphonyl" represents a phosphonyl in which E, $R^{vi}$ and $R^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phosphoryl" defines a phoshonyl in which E is absent, oxygen, alkoxy, aroxy, substituted alkoxy or substituted aroxy, as defined herein, and independently of E, $R^{vi}$ and $R^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, $R^{vi}$ and $R^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

As used herein, "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof. The term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof. The term "$C_3$-$C_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

As used herein, "sulfonyl" is represented by the formula

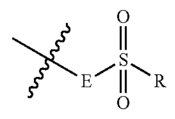

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of E and R can be substituted or unsubstituted amine, to form a "sulfonamide" or "sulfonamido." The substituted or unsubstituted amine is as defined above. The term "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

As used herein, "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

As used herein, "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

As used herein, the term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

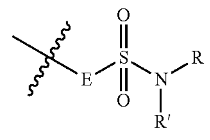

where E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide.

As used herein, "anti-infective" refers to compounds or molecules that can either kill an infectious agent or inhibit it from spreading. Anti-infectives include, but are not limited to, antibiotics, antibacterial s, antifungals, antiviral s, and anti protozoans.

As used herein, "chemotherapeutic agent" or "chemotherapeutic" refers to a therapeutic agent utilized to prevent or treat cancer.

As used herein, "immunomodulator," refers to an agent, such as a therapeutic agent, which is capable of modulating or regulating one or more immune function or response.

As used herein, "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, in aspects modulation may encompass an increase in the value of the measured variable by about 10 to 500 percent or more. In aspects, modulation can encompass an increase in the value of at least 10%, 20%, 30%, 40%, 50%, 75%, 100%, 150%, 200%, 250%, 300%, 400% to 500% or more, compared to a reference situation or suitable control without said modulation. In aspects, modulation may encompass a decrease or reduction in the value of the measured variable by about 5 to about 100%. In some embodiments, the decrease can be about 5%, 10%, 20%, 30%, 40%, 50%, 60%, 70%, 80%, 90%, 95%, 96%, 97%, 98%, 99% to about 100%, compared to a reference situation or suitable control without said modulation. In embodiments, modulation may be specific or selective, hence, one or more desired phenotypic aspects of a cell or cell population may be modulated without substantially altering other (unintended, undesired) phenotypic aspect(s).

As used herein, "nucleic acid," "nucleotide sequence," and "polynucleotide" are used interchangeably herein and generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein can refer to triple-stranded regions comprising RNA or DNA or both RNA and DNA. The strands in such regions can be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide as used herein can include DNAs or RNAs as described herein that contain one or more modified bases. Thus, DNAs or RNAs including unusual bases, such as inosine, or modified bases, such as tritylated bases, to name just two examples, are polynucleotides as the term is used herein. "Polynucleotide", "nucleotide sequences" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotides" as that term is intended herein. As used herein, "nucleic acid sequence" and "oligonucleotide" also encompasses a nucleic acid and polynucleotide as defined elsewhere herein.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "substantial" and "substantially," specify an amount of between 95% and 100%, inclusive, between 96% and 100%, inclusive, between 97% and 100%, inclusive, between 98% 100%, inclusive, or between 99% 100%, inclusive.

As used herein, "substantially free" means an object species is present at non-detectable or trace levels so as not to interfere with the properties of a composition or process.

As used herein, "substantially pure" means an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," refer to an amount (e.g., mass, volume, dosage, concentration, and/or time period) needed to achieve one or more desired result(s). For example, a therapeutically effective amount refers to an amount needed to achieve one or more therapeutic effects.

As used herein, "therapeutic" refers to treating, healing, and/or ameliorating a disease, disorder, condition, or side effect, or to decreasing in the rate of advancement of a disease, disorder, condition, or side effect. A "therapeutically effective amount" therefore refers to an amount of a compound that is capable of yeilding a therapeutic effect.

As used herein, the terms "treating" and "treatment" refer generally to obtaining a desired pharmacological and/or physiological effect. The effect can be, but does not necessarily have to be, prophylactic in terms of preventing or partially preventing a disease, symptom or condition thereof. effect can be therapeutic in terms of a partial or complete cure of a disease, condition, symptom or adverse effect attributed to the disease, disorder, or condition. The term "treatment" as used herein covers any treatment of a disease in a subject, particularly a human, and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, "water-soluble", generally means at least about 10 g of a substance is soluble in 1 L of water, i.e., at neutral pH, at 25° C.

All publications, published patent documents, and patent applications cited herein are hereby incorporated by reference to the same extent as though each individual publication, published patent document, or patent application was specifically and individually indicated as being incorporated by reference.

Overview

Bioorthagonal reactions have found widespread use in applications ranging from glycan engineering to in vivo imaging. Researchers have devised numerous reactions that can be predictably performed in a biological setting. Despite there being a plethora of bioorthagonal reaction schemes and reagents available, there still exists a need for new reactions, reagents, and/or methods that can improve, for example, the efficiency, the specificity, and/or the application of bioorthagonal reactions.

With that said, embodiments disclosed herein provide methods of selectively modifying a linked sialic acid or polysialic acid that include the steps of exposing a 2,3 linked sialic acid and/or a 2,8 linked polysialic acid to one or more condensing reagents (e.g., EDC, HOBt) under suitable reaction conditions to form a lactone at the 2,3 and/or 2,8 linkages; and exposing the lactone to a bi-functional linker or a primary amine under suitable reaction conditions to selectively modify the linked sialic acid and/or polysialic acid with the bi-functional linker or primary amine to selectively modify the linked sialic acid or polysialic acid. Also described herein are compositions and reagents produced by the methods of selectively modifying a linked sialic acid or polysialic acid. Also described herein are methods of using the modified linked sialic acid or polysialic acids described herein, such as in assays and/or delivery of a cargo or payload. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Methods of Selectively Modifiying Sialic and Polysialic Acids

Described herein are methods of selectively modifying sialic and polysialic acids. More specifically the methods described herein can selectively modify a 2,3 linked sialic acid and/or a 2,8 linked polysialic acid with one or more bi-functional linkers. The bi-functional linker contains a primary amine, and a second functionality that, in some embodiments, can be an alkyne, an azide, a biotin, an aromatic ring or a fused ring, a fluorescent dye, a mass spectrometry (MS) tag, a MS matrix (e.g., CHCA, DHB) or another biorthogonal group. The second functionality could be used as is or can be further modified. The methods described herein can render the selectively modified sialic or polysialic acids capable of being further modified with functional moieties via a reactive cargo molecule capable of reacting with the second functionality on the bi-functional linker on the modified sialic or polysialic acid. As used herein, the term "sialic acid" refers to any derivative of neuraminic acid. See e.g., Varki, Ajit; Roland Schauer (2008). "Sialic Acids". in Essentials of Glycobiology. Cold Spring Harbor Press. pp. Ch. 14 and Zhou et al. 2020. Cells. 9, 273; doi:10.3390. The numbering of the sialic acid structure begins at the carboxylate carbon and continues around the chain. The configuration that places the carboxylate in the axial position is the alpha-anomer as shown in the structures below.

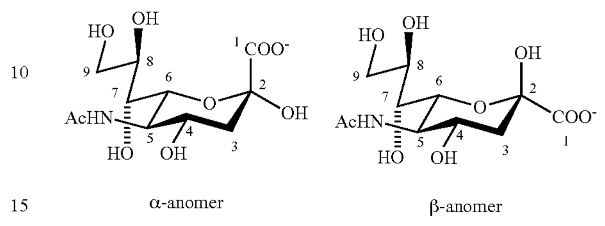
α-anomer β-anomer

The term "linked sialic acid" refers to the linkage, such as a glyosidic linkage, between the sialic acid and another sugar molecule, which can be optionally present in an oligosaccharide. Generally, sialic acids can be linked to another sugar molecule via a 2,3, 2,6, 2,8, or 2,9 linkage.

The term "polysialic acid" refers to a linear homopolymer of sialic acid units. Generally, the sialic acid subunits of a polysialic acid can be linked via 2,8 or 2,9 linkages.

In some embodiments, the method of selectively modifying a linked sialic acid or polysialic acid can include the steps of exposing a 2,3 linked sialic acid and/or a 2,8 linked polysialic acid to condensing reagents (e.g., EDC, HOBt) under suitable reaction conditions to form a lactone at the 2,3 and/or 2,8 linkages and exposing the lactone to a bi-functional linker with a primary amine under suitable reaction conditions to selectively modify the linked sialic acid and/or polysialic acid with the bi-functional linker with a primary amine to selectively modify the linked sialic acid or polysialic acid.

As used herein, "bi-functional linker" refers to any linking molecule that contains two reactive or functional moieties that allow linkage between two different molecules or compounds. In the context of the embodiments described herein, the bi-functional linker can react with the lactone formed from a 2,3 linked sialic acid and/or 2,8 linked polysialic acid as previously described. Bi-functional linkers can include, but are not limited to, bioorthangoanal reaction or "click chemistry" reaction handles or reagents. In some embodiments, the bi-functional linker includes a primary amine. The second functionality, in some embodiments, can be an alkyne, an azide or other functionalities. Exemplary bi-functional linkers include, but are not limited to Azido-PEG4-Amine, azido-propylamine, methyltetrazine amine, methyltetrazine-PEG4-amine, Azido-PEG3-Amine, Biotin-PEG3-amine, IsoTaG Biotin amine, Desthiobiotin-linker-amine, DBCO-linker-amine, FITC-linker-amine, CHCA-linker-amine, DHB-linker-amine, biotin-linker-amine, azido-linker-amine, alkyne-linker-amine. Other suitable bifunctional linkers will be appreciated by one of ordinary skill in the art in view of this description.

Non-limiting exemplary reactions and reaction conditions are provided in the Working Examples elsewhere herein. Additional exemplary suitable reaction conditions for forming the lactone by exposing the 2,3 linked sialic acid and/or the 2,8 linked polysialic acid to condensing reagents (EDC, HOBt) can include, but are not limited to condensing reagent (PyAOP) and condensing reagent (DMT-MM). Additional suitable reaction conditions for adding a bifunctional linker with primary amine to the lactone formed by reacting the linked sialic or poly sialic acid with condensing reagents (e.g., EDC, HOBt) include but are not limited to reacting the amino linker and an aprotic solvent. In some embodiments, the aprotic solvent can be DMSO. Other suitable aprotic solvents will be appreciated by one of ordinary skill in the art in view of the description herein. In some embodiments, the ratio of the aprotic solvent and the amino linker can be varied from 1: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more aprotic solvent to amino linker. In some embodiments, the ratio of amino linker to aprotic solvent can be varied from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino linker to aprotic solvent.

In some embodiments, the step of exposing can include reacting the condensing reagents (e.g., EDC, HOBt) and the 2,3 linked sialic acid and/or a 2,8 linked polysialic acid. Such reaction can occur under suitable conditions.

In some embodiments, the method further includes the step of exposing the selectively modified sialic acid and/or polysialic acid with a reactive cargo molecule whereby the reactive cargo molecule reacts with the second functionality on the bi-functional linker on the modified sialic acid or polysialic acid to selectively attach a cargo molecule at the linked sialic acid or polysialic acid.

The reactive cargo molecule can be a targeting moiety, a label (e.g., an optically active compound, a radioactive label, non-radioactive label, a mass separation label, or other label), a payload molecule, or a combination thereof. The reactive cargo can be a protein, peptide nucleic acid, nucleotide, radionuclide, sugar, oligosaccharide. In some embodiments, the reactive cargo can be an antibody or fragment thereof. In some embodiments, the reactive cargo can be an aptamer. In some embodiments, the reactive cargo can be a bioorthognal reaction handle or "click chemistry" reagent. Exemplary click chemistry reagents include, but are not limited to, fluorescent dyes, biotinylation reagents, FLAG or other epitope reaagents, nucleotide reagents, nucleoside reagents, amino acid reagents, monosaccharide reagents, oligosaccharide reagents, polysaccharide reagents, magnetic bead reagents, nanoparticle reagents, quantum dot reagents, and the like. In some embodiments, the click chemistry reagent is an azide containing click chemistry reagent. Exemplary click chemistry reagents include, but are not limited to, 3-Azido-7-hydroxycoumarin, axide-BDP=FL, 5-FAM-azide, 6-FAM-azide, picolyl-axide/6-FAM, AF488-azide, 5/6-Carboxyrhodamine 110-PEG3-Azide, 5-SIMA azide, 5-TAMARA azide, 5/6-TAMARA-PEG3-Azide, Cy3-Azide, Sulfo-Cy3-Azide, AF546-Azide, AF555-Azide, 5/6-Texas Red-PEG3-Azide, Cy5-azide, Sulfo-Cy5-Azide, AF647-Azide, Cy5.5-Azide, Cy7-Azide, Azide-PEG3-Biotin, Biotin-Azide, Picolyl-Azide-PEG4-Biotin, Diazo Biotin-azide, Dde-biotin-azide, Disulfide Biotin-Azide, DADPS Biotin-Azide, photocleavable biotin-azide, Azide-PEG3-desthiobiotin, Azide-$PEG_3$-FLAG, 8-Azido-AMP, 8-Azido-ADP, 8-Azido-ATP, 2'-Azido-2'-dATP, 3'-Azido-3'-dATP, 3'-Azido-2,3'-ddATP, gamma-(2-Azidoethyl)-ATP, gamma-(6-Azidohexyl)-ATP, gamma-[(6-Azidohexyl)-imido]-ATP, $N^6$-(6-Azido)hexyl-ATP, $N^6$-(6-Azido)3'-hexyl-ATP, 3'-Azido-3'-dGTP, 3'-Azido-2,3'-ddGTP, 3'-Azido-3'-dUTP, 3'-Azido-2,3'-ddUTP, 5-Azido-$PEG_4$-UTP, 5-Azido-$C_3$-UTP, 5-Azidomethyl-dUTP, 5-Azidomethyl-UTP, Azide-$PEG_4$-aminoallyl-dUTP, 5-Azido-$PEG_4$-CTP, 5-Azido-$PEG_4$-dCTP, 3'-Azido-3'-dCTP, pCp-Azide, AzTMP, AzTTP, 2-azido-adenosine, 8-azido-adenosine, 3'-Azido-3'-deoxyadenosine, 5-Azidomethyl-uridine (5-AmU), 5-Azidomethyl-2'-deoxyuridine (5-AmdU), 5-(3-Azidopropyl)-2'-dideoxyuridine, 3'-Azido-2',3'-dideoxythymidine, 3-azido-D-alanine HCl, 3-azido-L-alanine HCl, 4-azido-D-homoalanine HCl, 4-azido-L-homoalanine HCl, 4-azido-D-phenylalanine, 4-azido-L-phenylalanine, 5-azido-D-ornithine HCl, 5-azido-L-ornithine HCl, 6-Azido-D-lysine HCl, 6-Azido-L-lysine HCl, Ac4ManNAz, AC4GlcNAz, AC4GalNAz, UDP-GalNAz, UDP-6-azide-glucose, 6-azido-trehalose, pLEG-Azide, Kdo-Azide, azide-agarose, Dde Azide-agarose, In some embodiments, the reactive cargo molecule can be a payload molecule. As used herein, "payload molecule" refers to a molecule or compound that is an active agent to be delivered to a subject. As used herein, "active agent" or "active ingredient" refers to a substance, compound, or molecule, which is biologically active or otherwise induces a biological or physiological effect on a subject to which it is administered to or otherwise results in a detectable change in the subject to which it is administered. In other words, "active agent" or "active ingredient" refers to a component or components of a composition to which the whole or part of the effect of the composition is attributed. In some embodiments, the payload molecule is a pharmaceutical agent or drug. In some embodiments, the payload molecule is a polynucleotide modifying agent (e.g., a CRISPR-Cas system or component thereof, TALEN, ZFN or other polynucleotide-guided nuclease), immunomodulator, antibody or fragment thereof, antipyretic, chemotherapeutic, anti-neoplastic agent, anti-fungal, anti-bacterial, anti-viral, a pain modulating agent, anti-microbial agent, anti-infective agent, radioactive agent, acoustic agent, or a combination thereof. The payload can be a polynucleotide, amino acid, peptide, protein, organic compound, inorganic compound, or a combination thereof. In some embodiments, the payload can be an imaging agent.

The term "targeting moiety" is used herein to refer to a molecular structure that facilitates the modified sialic acids and/or modified polysialic acids to localize to a targeting area, region, tissue, cell etc., e.g., to help enter a cell, or bind a receptor. The moiety can be composed of or be a vitamin, antibody, antigen, receptor, receptor substrate, DNA, RNA, sialyl Lewis X antigen, hyaluronic acid, sugars, cell specific lectins, steroid or steroid derivative, RGD peptide, ligand for a cell surface receptor, serum component, or combinatorial molecule directed against various intra- or extracellular receptors. The targeting moiety can be or include a lipid or a phospholipid. Exemplary phospholipids include, without limitation, phosphatidylcholines, phospatidylserine, phospatidylinositol, phospatidylglycerol, and phospatidylethanolamine. These lipids may be in the form of micelles or liposomes and the like. The targeting moiety may further comprise a detectable label or alternately a detectable label may serve as a targeting moiety. When the conjugate has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, calorimetric (e.g., dyes), metal ions, radioactive moieties, gold particles, quantum dots, and the like.

The term "optically active compound" as used herein refers to any molecule or atom e.g., nucleic acid, amino acid, peptide, polypeptide, particle (e.g., quantum dots, nanotubes, fullerenes, metallic clusters, and the like) that exhibits the property of "optical activity". Optical activity is the ability to rotate the plane of incident linearly polarized light, with a dependence on wavelength, the ability to reflect or emit a wavelength of light. In some embodiments, the wavelength of light reflected or emitted is in the visible (about 430 nm to 750 nm) infrared, ultra-violet, or X-ray range. Light can be produced by the optically active compound by any method including, but not limited resonance transfer, resonance, florescence, and luminescence.

The term "radioactive label" refers to a molecule or compound that includes a radioactive atom. Such radioactive atoms can include, but are not limited to, isotopes of H (e.g. $^{1}H$ and $^{3}H$), C (e.g. $^{14}C$) Na (e.g. $^{22}Na$), P (e.g. $^{32}P$ and $^{33}P$), S (e.g. $^{35}S$), Cl (e.g. $^{36}Cl$), Ca (e.g. $^{45}Ca$), Cr (e.g. $^{51}Cr$) Co (e.g. $^{57}Co$ and $^{58}Co$), Fe (e.g. $^{59}Fe$), Rb (e.g. $^{86}Rb$) and I (e.g. $^{125}I$ and $^{131}I$). Other suitable radio isotopes are known in the art.

The term "non-radioactive label" refers to a molecule or compound that facilitates indirect detection or measurement of a compound (by measuring the presence, activity, or function of the label molecule or compound by non-radioactive means, including, but not limited to, enzyme activity, immunodetection of the label, non-radioactive optical activity (e.g., luminescence, fluorescence, and the like). Exemplary non-radioactive labels include an optically active compounds (e.g. luciferase, fluorescent proteins (GFP, YFP, BFP, RFP, etc. and variants thereof), dyes (e.g. epitope tags (e.g. V5-tag, Myc-tag, HA-tag, Spot-tag, T7-tag, FLAG-tag, His-tag, S-tag, TC tag, Ty tag, Xpress tag, and the like), binding tags (isopeptag, spyTag, SnoopTag, DogTag, SdyTag, and the like), protein/enzyme tags (biotin, streptavidin, BCCP, Glutithione-S-transferase-tag, fluorescent tags, HaloTag, SNAP-tag, CLIP-tag, Maltose binding protein tag, Nus-tag, Thioredoxin-tag, Fc-tag, beta-galactosidase, and the like).

As used herein, the term "mass separation label" refers to any compound or molecule that changes the mass, ionization, or other characteristic that allows identification of the labeled molecule using a mass spectrometry or other mass separation method. Such labels include, but are not limited to any suitable label described herein, stable isotope labels (including stable isotope-coded affinity tags, isobaric labeling (e.g., TMT), isobaric tags for relative and absolute quantification (iTRAQ), metal-coded tags (e.g. MeCAT), N-terminal labelling, stable isotope labeling with amino acids in cell culture (SILAC), and terminal amine isotopic labeling of substrates (TAILS).

In some embodiments, the bi-functional linker is a propargyl amine or an azido amine, whereby the resulting selectively modified sialic acid and/or polysialic acid is modified to contain a reactive alkyne and/or a reactive azide. The propargyl amine or azide can be substituted or unsubstituted.

The term "reactive alkyne" refers to a substituted or unsubstituted unsaturated hydrocarbon containing at least one triple bond. In some embodiments, the reactive alkyne can have the general formula: R—C≡C—R' as represented by the empirical formula of $C_nH_{2n-2}$, where n can range from 1 to 30. In some embodiments, n is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. The reactive alkyne can be straight chained or branched chained.

The term "azide" is a term of art that refers to a chemical compound containing an azido group ($N_3^-$), can have an azdie functional group having the general formula of $RN_3$ and can be capable of reacting with one or more other groups in a reaction. In some embodiments, the azide functional group can be represented by resonance structures:

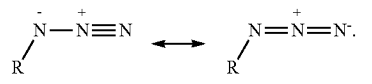

In some embodiments, the linked sialic acid and/or polysialic acid is attached to or otherwise incorporated with a biologic molecule. Suitable biologic molecules include, but are not limited to, polynucleotides, peptides, proteins, lipids, carbohydrates, and combinations thereof.

In some embodiments, the biological molecule is a protein. In some embodiments, the biologic molecule is an antibody or a fragment thereof. In some embodiments, the biologic molecule is a glycoprotein.

In some embodiments, the linked sialic acid and/or polysialic acid is attached to or otherwise incorporated with a biological molecule before exposing to condensing reagents (e.g., EDC, HOBt) and/or exposing the lactone, and/or exposing the selectively modified sialic acid and/or polysialic acid, or a combination thereof. In some embodiments, the linked sialic acid and/or polysialic acid is attached to or otherwise incorporated with a biological molecule after exposing to condensing reagents (e.g., EDC, HOBt) and/or exposing the lactone, and/or exposing the selectively modified sialic acid and/or polysialic acid, or a combination thereof.

In some embodiments, the biologic molecule is integrated into or is otherwise part of or coupled to one or more components of a cell. In some embodiments, the biologic molecule is integrated into or is otherwise part of or coupled to one or more components of a micelle, exosome, or other vesicle. In some embodiments, the biologic molecule is a protein and is integrated into, is otherwise part of, and/or is coupled to one or more components of a cell. In some embodiments, the biological molecule is further coupled to, integrated with, or otherwise associated with or a cell or component thereof (e.g., receptor, organelle, membrane thereof (e.g., cell, nuclear, vesicle, and/or endoplasmic reticulum), or a vesicle (e.g., exosome, endosome, micelle, liposome, etc.).

In some embodiments, the reactive cargo molecule is a mass spectrometry matrix molecule. As used herein, "mass spectrometry matrix molecule" refers to a compound that can form or become part of a mass spectrometry matrix, which can be any compound that promoters the formation of ions during certain mass spectrometry techniques. Exemplary compounds include, but are not limited to, 9-aminoacridine, alpha-cyano-4-hydroxycinnamic acid, ferulic acid, 2,5-dihydroxy benzoic acid, 3-hydroxy picolinic acid, picolinic acid, sinapinic acid 2,5-dihydroxybenzoic acid, 2-aminobenzyl alcohol, anthranilic acid, 2-hydroxyacetophenone, glycerol, thioglycerol, 3-nitrobenzyl alcohol, 18-crown-6 etherm 2-nitrophenyloctyl ether, diethanolamine, and triethanolamine. Others will be appreciated by those of ordinary skill in the art and are within the scope of this disclosure.

In some embodiments, one or more of the steps is performed in vitro, ex vivo, or in situ.

Selectively Modified Sialic and Polysialic Acids and Uses Thereof

Also described herein, are the selectively modified sialic acid and polysialic acid compounds and compositions that can be generated by any of the methods described herein. It will be appreciated that such compositions can include a biological molecule (e.g., proteins, vesicles, membranes, and/or cells, for example) to which the modified sialic acids can be attached and any other molecule or composition to which the biological molecule is coupled to, attached, or otherwise associated with. By adding a reactive cargo molecule, the biological molecule and any other composition the biological molecule is coupled, attached to, or otherwise associated with can be afforded the attributes of the reactive cargo molecule and/or become a delivery vehicle for the cargo molecule.

Pharmaceutical Formulations

Also described herein are pharmaceutical formulations that can contain an amount, effective amount, and/or least effective amount, and/or therapeutically effective amount of one or more compounds and compositions containing a selectively modified 2,3 linked sialic acid and/or 2,8 linked polysialic acid, (which are also referred to as the primary active agent or ingredient elsewhere herein) described in greater detail elsewhere herein a pharmaceutically acceptable carrier. When present, the compound can optionally be present in the pharmaceutical formulation as a pharmaceutically acceptable salt. In some embodiments, the pharmaceutical formulation can include, such as an active ingredient, one or more of the compounds and compositions containing a selectively modified 2,3 linked sialic acid and/or 2,8 linked polysialic acids that can be made by a method described herein.

The pharmaceutical formulations described herein can be administered via any suitable method or route to a subject in need thereof. Suitable administration routes can include, but are not limited to auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratym panic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated and/or the active ingredient(s).

Where appropriate, compounds, molecules, other composition, or a combination thereof described in greater detail elsewhere herein can be provided to a subject in need thereof as an ingredient, such as an active ingredient or agent, in a pharmaceutical formulation. As such, also described are pharmaceutical formulations containing one or more of the compounds and salts thereof, or pharmaceutically acceptable salts thereof described herein. Suitable salts include, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, malonate, mandelate, malate, phthalate, and pamoate.

In some embodiments, the subject in need thereof has or is suspected of having an disease or a symptom thereof. As used herein, "agent" refers to any substance, compound, molecule, and the like, which can be biologically active or otherwise can induce a biological and/or physiological effect on a subject to which it is administered to. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

Pharmaceutically Acceptable Carriers and Auxiliary Ingredients and Agents

The pharmaceutical formulation can include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active compound.

In some embodiments, the pharmaceutical formulation can also include an effective amount of auxiliary active agents, including but not limited to, biologic agents or molecules (including but not limited to (e.g. polypeptides, polynucleotides, antibodies and fragments thereof, aptamers, and the like), chemotherapeutics, antineoplasic agents, hormones, antibiotics, antivirals, immunomodulating agents, antinausea, pain modifying compounds (such as opiates), anti-inflammatory agents, antipyretics, antibiotics, and combinations thereof.

Effective Amounts

In some embodiments, the amount of the primary active agent and/or optional auxiliary active agent can be an effective amount, least effective amount, and/or therapeutically effective amount. The effective amount, least effective amount, and/or therapeutically effective amount of the primary and optional auxiliary active agent described elsewhere herein contained in the pharmaceutical formulation can range from about 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 pg, ng, μg, mg, or g or be any numerical value with any of these ranges. In some embodiments, the effective amount, least effective amount, and/or therapeutically effective amount can be an effective concentration, least effective concentration, and/or therapeutically effective concentration, which can each range from about 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 pM, nM, μM, mM, or M or be any numerical value with any of these ranges.

In other embodiments, the effective amount, least effective amount, and/or therapeutically effective amount of the auxiliary active agent can range from about 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 IU or be any numerical value with any of these ranges.

In some embodiments, a primary active agent can be present in the pharmaceutical formulation can range from about 0 to 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.9, to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the pharmaceutical formulation.

In some embodiments, the auxiliary active agent, when optionally present, can range from about 0 to 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.9, to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the pharmaceutical formulation.

In some embodiments where a cell population is delivered, the effective amount of cells can range from about $1\times10^1$/mL to $1\times10^{20}$/mL or more, such as about $1\times10^1$/mL, $1\times10^2$/mL, $1\times10^3$/mL, $1\times10^4$/mL, $1\times10^5$/mL, $1\times10^6$/mL, $1\times10^7$/mL, $1\times10^8$/mL, $1\times10^9$/mL, $1\times10^{10}$/mL, $1\times10^{11}$/mL, $1\times10^{12}$/mL, $1\times10^{13}$/mL, $1\times10^{14}$/mL, $1\times10^{15}$/mL, $1\times10^{16}$/mL, $1\times10^{17}$/mL, $1\times10^{18}$/mL, $1\times10^{19}$/mL, to/or about $1\times10^{20}$/mL.

In embodiments where there is an auxiliary active agent contained in the pharmaceutical formulation, the effective amount of the auxiliary active agent will vary depending on the auxiliary active agent.

When optionally present in the pharmaceutical formulation, the auxiliary active agent can be included in the pharmaceutical formulation or can exist as a stand-alone compound or pharmaceutical formulation that can be administered contemporaneously or sequentially with the compound, derivative thereof, or pharmaceutical formulation thereof. In yet other embodiments, the effective amount of the auxiliary active agent can range from about 0 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the total auxiliary active agent pharmaceutical formulation. In additional embodiments, the effective amount of the auxiliary active agent can range from about 0 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the total pharmaceutical formulation.

Dosage Forms

In some embodiments, the pharmaceutical formulations described herein can be in a dosage form. The dosage form can be administered to a subject in need thereof. The dosage form can be effective generate specific concentration, such as an effective concentration, at a given site in the subject in need thereof. In some cases, the dosage form contains a greater amount of the active ingredient than the final intended amount needed to reach a specific region or location within the subject to account for loss of the active components such as via first and second pass metabolism.

The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, internasal, and intradermal. Other appropriate routes are described elsewhere herein. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. Where appropriate, the dosage forms described herein can be microencapsulated.

The dosage form can also be prepared to prolong or sustain the release of any ingredient. In some embodiments, compounds, molecules, compositions, vectors, vector systems, cells, or a combination thereof described herein can be the ingredient whose release is delayed. In some embodiments the primary active agent is the ingredient whose release is delayed. In some embodiments, an optional auxiliary agent can be the ingredient whose release is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water-soluble polymer, water insoluble polymers, and/or pH dependent polymers, with or without water insoluble/water soluble non-polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these embodiments, primary active ingredient(s), and/or optional auxiliary active ingredient(s), and/or pharmaceutically acceptable salt thereof where appropriate are incorporated into a liposome. In embodiments where the dosage form is a liposome, the pharmaceutical formulation is thus a liposomal formulation. The liposomal formulation can be administered to a subject in need thereof.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, a primary active ingredient, optional auxiliary active ingredient, and/or pharmaceutically acceptable salt thereof where appropriate can be formulated with a paraffinic or water-miscible ointment base. In other embodiments, the primary and/or auxiliary active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, a primary active ingredient, optional auxiliary active ingredient, and/or pharmaceutically acceptable salt thereof where appropriate can be in a dosage form adapted for inhalation is in a particle-size-reduced form that is obtained or obtainable by micronization. In some embodiments, the particle size of the size reduced (e.g., micronized) compound or salt or solvate thereof, is defined by a $D_{50}$ value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active (primary and/or auxiliary) ingredient, which may be generated by various types of metered dose pressurized aerosols, nebulizers, or insufflators. The nasal/inhalation formulations can be administered to a subject in need thereof.

In some embodiments, the dosage forms are aerosol formulations suitable for administration by inhalation. In some of these embodiments, the aerosol formulation contains a solution or fine suspension of a primary active ingredient, auxiliary active ingredient, and/or pharmaceutically acceptable salt thereof where appropriate and a pharmaceutically acceptable aqueous or non-aqueous solvent. Aerosol formulations can be presented in single or multidose quantities in sterile form in a sealed container. For some of these embodiments, the sealed container is a single dose or multi-dose nasal or an aerosol dispenser fitted with a metering valve (e.g., metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a primary active ingredient, optional auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time. The aerosol formulations can be administered to a subject in need thereof.

For some dosage forms suitable and/or adapted for inhaled administration, the pharmaceutical formulation is a dry powder inhalable-formulations. In addition to a primary active agent, optional auxiliary active ingredient, and/or pharmaceutically acceptable salt thereof where appropriate, such a dosage form can contain a powder base such as lactose, glucose, trehalose, manitol, and/or starch. In some of these embodiments, a primary active agent, auxiliary active ingredient, and/or pharmaceutically acceptable salt thereof where appropriate is in a particle-size reduced form. In further embodiments, a performance modifier, such as L-leucine or another amino acid, cellobiose octaacetate, and/or metals salts of stearic acid, such as magnesium or calcium stearate. In some embodiments, the aerosol formulations are arranged so that each metered dose of aerosol contains a predetermined amount of an active ingredient, such as the one or more of the compositions, compounds, vector(s), molecules, cells, and combinations thereof described herein.

Dosage forms adapted for vaginal administration can be presented as pessaries, tampons, creams, gels, pastes, foams, or spray formulations. Dosage forms adapted for rectal administration include suppositories or enemas. The vaginal formulations can be administered to a subject in need thereof.

Dosage forms adapted for parenteral administration and/or adapted for injection can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and re-suspended in a sterile carrier to reconstitute the dose prior to administration. Extemporaneous injection solutions and suspensions can be prepared in some embodiments, from sterile powders, granules, and tablets. The parenteral formulations can be administered to a subject in need thereof.

For some embodiments, the dosage form contains a predetermined amount of a primary active agent, auxiliary active ingredient, and/or pharmaceutically acceptable salt thereof where appropriate per unit dose. In an embodiment, the predetermined amount of primary active agent, auxiliary active ingredient, and/or pharmaceutically acceptable salt thereof where appropriate can be an effective amount, a least effect amount, and/or a therapeutically effective amount. In some embodiments, the predetermined amount can be effective to treat and/or prevent a disease or symptom thereof in a subject to which it is administered.

In other embodiments, the predetermined amount of a primary active agent, auxiliary active agent, and/or pharmaceutically acceptable salt thereof where appropriate, can be an appropriate fraction of the effective amount of the active ingredient. Such unit doses may therefore be administered once or more than once a day, month, or year (e.g., 1, 2, 3, 4, 5, 6, or more times per day, month, or year). Such pharmaceutical formulations may be prepared by any of the methods well known in the art.

Kits

Any of the compounds, compositions, formulations, particles, cells, described herein or a combination thereof, such as the compounds and compositions that can contain a selectively modified 2,3-linked and/or 2,8-linked polysialic acid described herein, can be presented as a combination kit. As used herein, the terms “combination kit” or “kit of parts” refers to the compounds, compositions, formulations, particles, cells and any additional components that are used to package, sell, market, deliver, and/or administer the combination of elements or a single element, such as the active ingredient, contained therein. Such additional components include, but are not limited to, packaging, syringes, blister packages, bottles, and the like. When one or more of the compounds, compositions, formulations, particles, cells, described herein or a combination thereof (e.g., agents) contained in the kit are administered simultaneously, the combination kit can contain the active agents in a single formulation, such as a pharmaceutical formulation, (e.g., a tablet) or in separate formulations. When the compounds, compositions, formulations, particles, and cells described herein or a combination thereof and/or kit components are not administered simultaneously, the combination kit can contain each agent or other component in separate pharmaceutical formulations. The separate kit components can be contained in a single package or in separate packages within the kit.

In some embodiments, the combination kit also includes instructions printed on or otherwise contained in a tangible medium of expression. The instructions can provide information regarding the content of the compounds, compositions, formulations, particles, cells, described herein or a combination thereof contained therein, safety information regarding the content of the compounds, compositions, formulations (e.g., pharmaceutical formulations), particles, and cells described herein or a combination thereof contained therein, information regarding the dosages, indications for use, and/or recommended treatment regimen(s) for the compound(s) and/or pharmaceutical formulations contained therein. In some embodiments, the instructions can provide directions for administering the compounds, compositions, formulations, particles, and cells described herein or a combination thereof to a subject in need thereof.

Uses

The compounds and compositions containing a selectively modified sialic and/or polysialic acid described herein can be used in a variety of applications. In some embodiments, the compounds and compositions containing a selectively modified sialic and/or polysialic acid described herein can be administered to a subject or a sample therefrom. In some embodiments, the compounds and compositions containing a selectively modified sialic and/or polysialic acid described herein can be delivered to a sample. In some embodiments, the compounds and compositions containing a selectively modified sialic and/or polysialic acid described herein can be used a delivery vehicle for a payload (or cargo) molecule to a subject or sample.

In some embodiments, the compounds and compositions containing a selectively modified sialic and/or polysialic acid described herein can be used as an imaging or analytic composition. In some embodiments the sample can be prepared for microscopic imaging or other analysis technique. In some embodiments, the sample can be prepared/processed using a composition described herein can be analyzed using a mass spectrometry technique. Suitable mass spectrometry analysis techniques are described herein, such as in the Working Examples herein, and will be further appreciated by those of ordinary skill in the art in view of this disclosure. In some embodiments, the sample is or has been embedded partially or completely fixed in formalin or other fixing agent, and/or wholly or partially embedded in paraffin. In some embodiments, the sample already contains a 2,3 linked sialic acid or 2,8 linked polysialic acid and one or more of the methods previously described are performed on the sample to selectively modify the 2,3 linked sialic acid or 2,8 linked polysialic acid in situ, in vito, or ex vivo. In this way, the compounds and compositions can allow for analyzing a previously processed sample. In some embodiments, where a sample does not contain a 2,3 linked sialic acid or 2,8 linked polysialic acid, the sample can be first modified to contain one or both.

In some embodiments, the compounds and compositions containing a selectively modified sialic and/or polysialic acid described herein can be used an agent delivery composition. In other words, the compounds and compositions containing a selectively modified sialic and/or polysialic acid described herein can deliver an attached cargo to one or more cells. In some embodiments, the compounds and compositions containing a selectively modified sialic and/or polysialic acid described herein can be used to deliver a cargo molecule that is a treatment or prevention for a disease or a diagnostic agent to a subject. In some embodiments, the reactive cargo is a targeting moiety and the biological molecule is or contains a therapeutic or diagnostic agent (e.g., an imaging agent). Thus, in this way, the compounds described herein can provide a targeted therapy or diagnostic.

In some embodiments, the compounds and compositions containing a selectively modified sialic and/or polysialic acid described herein can be used as a mass spectrometry reagent. In some of these embodiments, the use of the compounds and compositions containing a selectively modified sialic and/or polysialic acid described herein can eliminate the need for a matrix.

In some embodiments described herein are assays that include utilizing the compounds and compositions containing a selectively modified sialic and/or polysialic acid described herein that contains one or more cargos. The assays can be used to detect and/or quantify a characteristic of a cell, cell population, tissue, component thereof, or any combination thereof.

In some embodiments, the assay includes exposing a cell or cell population, a tissue, or the component thereof to a selectively modified sialic acid or polysialic acid described herein containing a cargo molecule and detecting, quantifying, or both one or more characteristics of the cell or cell population, tissue, component thereof or a combination thereof. In some embodiments, the sialic acid or poly sialic acid is selectively modified at the 2 position of the linked sialic acid or the polysialic acid. In some embodiments, the linked sialic acid or the polysialic acid is 2,3 linked, 2,6 linked, or 2,8 linked. In some embodiments, the selectively modified linked sialic acid or polysialic acid is selectively modified to include a cargo molecule. In some embodiments, the assay includes detecting, quantifying, or both one or more characteristics of the cell or cell population, tissue, or component thereof. In some embodiments, exposing the cell or cell population, the tissue, or the component thereof in vitro, ex vivo, or in situ. In some embodiments, the one or more characteristics of the cell or cell population, the tissue, or the component thereof detected, quantified, or both is gene expression, protein expression, metabolites, growth, protein modification, cell or tissue composition, cell or tissue morphology, cell or tissue temporal or spatial localization and combinations thereof. In some embodiments, detecting, quantifying, or both comprises mass spectrometry, a cell or tissue staining technique, an affinity detection technique, an immunodetection technique, sequencing (e.g., nucleic acid sequencing and protein sequencing), post translation protein modification detection, a cell or tissue imaging technique, or any combination thereof.

In some embodiments, the assay further includes selectively modifying a linked sialic acid or polysialic acid, wherein selectively modifying includes exposing a 2,3 linked, a 2,6 linked, or a 2,8 linked sialic acid or polysialic acid to a condensing reagent under suitable reaction conditions to form a lactone at the 2,3, 2,6 or 2,8 linkages and exposing the lactone to a bi-functional linker with a primary amine under suitable reaction conditions to selectively modify the linked sialic acid or polysialic acid with a functionality on the bi-functional linker thereby selectively modifying the linked sialic acid or polysialic acid with the bi-functional linker at the 2 position of the linked sialic acid or polysialic acid.

In some embodiments, the assay can further include selectively attaching a cargo molecule to the selectively modified linked sialic or polysialic acid by exposing the selectively modified linked sialic acid or polysialic acid with a reactive cargo molecule whereby the reactive cargo molecule reacts with an available reactive functionality on the bi-functional linker thereby selectively attaching the cargo molecule the linked sialic acid or polysialic acid. In some embodiments the bi-functional linker is or comprises a propargyl amine or an azide amine, whereby the resulting selectively modified linked sialic acid or polysialic acid is modified to contain a reactive alkyne, a reactive azide, or both. In some embodiments, the linked sialic acid or polysialic acid is attached to or is otherwise incorporated with a biological molecule. In some embodiments, the linked sialic acid or polysialic acid is attached to or otherwise incorporated with a biological molecule before exposing to the condensing reagent, exposing the lactone, exposing the selectively modified linked sialic acid or polysialic acid, or a combination thereof.

In some embodiments, the selectively modified linked sialic acid or polysialic acid is attached to or otherwise incorporated with a biological molecule after exposing to a dimethyl amine, exposing the lactone, exposing the selectively modified linked sialic acid or polysialic acid, or a combination thereof. In some embodiments, the biologic molecule is a protein. In some embodiments, the protein is an antibody or fragment thereof. In some embodiments, the biologic molecule is a targeting moiety. In some embodiments, the targeting moiety is an antibody or fragment thereof, aptamer, receptor ligand, protein receptor, or any combination thereof. In some embodiments, the biologic molecule is integrated into or is otherwise part of or coupled to one or more components of a cell and/or a cell. Thus, in these embodiments, the linked sialic acid or polysialic acid can be attached and deliver or be delivered by the cell to which it is incorporated with. For example, the selectively modified linked sialic acid or polysialic acid described herein (including any attached cargo) can be delivered to a subject via delivery of the one or more cell components or cell to which it is attached. In some embodiments, the biologic molecule is molecule is integrated into, is otherwise part of, or is coupled to one or more components of a micelle, exosome, liposome, or other vesicle. Attachment of the selectively modified linked sialic acid or polysialic acid to a biological molecule occurs in vivo, ex vivo, in situ, or in vitro.

Any suitable cargo molecule can be attached to the selectively modified linked sialic acid or polysialic acid compounds and compositions described herein. Exemplary cargo molecules include, but are not limited to, biologically active agents, therapeutic agents, imaging agents, spectrometry matrix molecules (e.g., mass spectrometry matrix molecules) and combinations thereof. Additional exemplary cargo molecules include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, radiation sensitizers, chemotherapeutics, genetic modifying agents and systems (e.g., TALENs, Zinc Finger Nucleases, CRISPR-Cas systems etc.), and combinations thereof.

In some embodiments of the assay, the cell or cell population, the tissue, or the component thereof is/are fixed in formalin. In some embodiments, the cell or cell population, the tissue, or the component thereof is attached or immobilized on a surface of an object. As used herein, "surface," in the context herein, refers to a boundary of an object. The surface can be an interior surface (e.g., the interior boundary of a hollow object), or an exterior or outer boundary of an object. Generally, the surface of an object corresponds to the idealized surface of a three dimensional solid that is topological homeomorphic with the object. The surface can be an exterior surface or an interior surface. An exterior surface forms the outermost layer of an object (such as a slide or device). An interior surface surrounds an inner cavity of an object, such as the inner cavity of a tube or capillary. As an example, both the outside surface of a tube and the inside surface of a tube are part of the surface of the tube. However, internal surfaces of the object that are not in topological communication with the exterior surface, such as a tube with closed ends, can be excluded as the surface of an object. In some embodiments, an exterior surface of the product is chemically modified, e.g., a surface that can contact an immune system component or biological agent or cargo of the compounds and compositions described herein. In some embodiments, where the object is porous or has holes in its mean (idealized or surface), the internal faces of passages and holes are not considered part of the surface of the object if its opening on the mean surface of the product is less than 1 μm. The object can be rigid, semi-flexible, flexible, optically opaque, fully or partially optically translucent, or any combination thereof. In some embodiments, the surface is a glass or polymeric slide, well, cell culture vessel, or capillary (including micro capillaries). In some embodiments, the surface is modified so as to enhance attachment of immobilization of the cell or cell population, tissue, component thereof or any combination thereof to the surface. In some embodiments, the cell or cell population, tissue, component thereof is releasably attached or immobilized to the surface. In some embodiments, the cell or cell population, tissue, component thereof are not attached to or otherwise immobilized or associated with a surface.

In some embodiments, the cell or cell population, tissue, components thereof, or any combination thereof are obtained from a subject prior to exposure to the selectively modified linked sialic acid or polysialic acid compounds and compositions described herein.

In some embodiments, the cell or cell population, tissue, components thereof, or any combination thereof is exposed to a candidate agent. The term "agent" broadly encompasses any condition (such as environmental or abiotic stress or condition), substance or agent capable of modulating one or more phenotypic aspects of a cell or cell population as disclosed herein. Such conditions, substances or agents may be of physical, chemical, biochemical and/or biological nature. The term "candidate agent" refers to any condition, substance or agent that is being examined for the ability to modulate one or more phenotypic aspects of a cell or cell population as disclosed herein in a method comprising applying the candidate agent to the cell or cell population (e.g., exposing the cell or cell population to the candidate agent or contacting the cell or cell population with the candidate agent) and observing an effect. It will be appreciated that observation of an effect in embodiments of the assay described herein can be facilitated by the linked sialic acid or polysialic acid compounds and compositions described herein to which the cell or cell population, tissue, or component thereof is exposed to during the assay. Exposure to the candidate agent can be prior to, at the same time, and or after exposure to the linked sialic acid or polysialic acid compounds and compositions described herein. In some embodiments, exposure to the candidate agent can be in vivo, ex vivo, or in vitro. In some embodiments, exposure to the candidate agent can occur prior to or after obtaining the cell or cell population, tissue, or component thereof from a subject. Thus, embodiments of the assay described herein can be utilized for evaluating environmental stress and/or state, for screening of chemical libraries, and to screen or identify structural, syntenic, genomic, and/or organism and species variations. For example, a culture of cells, can be exposed to an environmental stress, such as but not limited to heat shock, osmolarity, hypoxia, cold, oxidative stress, radiation, starvation, a chemical (for example a therapeutic agent or potential therapeutic agent) and the like. After the stress is applied, a representative sample can be subjected to analysis, for example at various time points, and compared to a control, such as a sample from an organism or cell, for example a cell from an organism, or a standard value. By exposing cells, or fractions thereof, tissues, or even whole animals, to different members of the chemical libraries, and performing the methods described herein, different members of a chemical library can be screened for their effect on cells or cell populations, tissues, and/or components thereof, thereof simultaneously in a relatively short amount of time, for example using a high throughput method. In some embodiments, the assay can be used to develop a personalized treatment regimen or strategy based upon the observed effect of a candidate agent on the cell or cell population, tissue, component thereof, or combination thereof for the subject from which the cell or cell population, tissue, component thereof or combination thereof was obtained or was evaluated (such as an in vivo assay).

In some embodiments, the assay can include analyzing the sample with a suitable imaging technique, such as microscopy technique. In some embodiments, analyzing includes an immunodetection of one or more proteins. In some embodiments, analyzing can include analyzing the sample using a suitable mass spectrometry technique.

In some embodiments, the assay can provide diagnostic and/or prognostic information regarding subject from which the cell or cell population, tissue, component thereof, or combination thereof was obtained or evaluated. In some embodiments, the cell or cell population, tissue, component thereof, or combination thereof is from a tumor or suspected tumor or is otherwise suspected to be diseased or otherwise abnormal.

Further embodiments are illustrated in the following Examples which are given for illustrative purposes only and are not intended to limit the scope of the invention.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1—Biotin Azide Preparation

Scheme 1

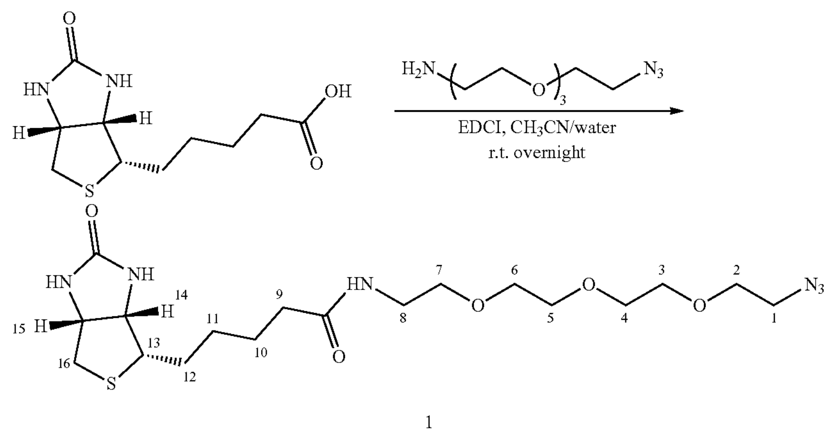

1

Biotin azide was prepared according to Scheme 1. To a cooled (0° C.) mixture of D-biotin (200 mg, 0.82 mmol), 1-ethyl-3-(3-dimethylaminopropyl)carbodiimide hydrochloride (EDC·HCl) (205 mg, 1.1 mmol) and 6 mL of CH3CN was added a mixture of 1-amino-11-azido-3,6,9-trioxaundecane (194 μL, 213.89 mg, 0.98 mmol) in 2 mL MeOH. The reaction mixture was stirred at 0° C. for 0.5 h and was then allowed to warm to ambient temperature. The mixture was stirred at room temperature overnight. Solvent was evaporated and reaction mixture was dissolved in 3 mL MeOH and centrifuged. Supernatant was collected and loaded onto TLC plate. The TLC plate was developed with DCM-MeOH 10/1 to yield xlu-I-135-1 (230 mg, 63%). Structure was confirmed by NMR and MS. $^1$H-NMR data agree with previously reported data[1]. Spectra are shown in FIGS. 1-4 of U.S. Provisional Application 63/010,499, filed on Apr. 15, 2020, which is incorporated by reference as if expressed in its entirety herein. $^1$H NMR (600 MHz; $D_2O$): 4.64 (dd, 1H, $J_{15,16a}$=4.8 Hz, $J_{15,NH}$=8.0 Hz, H-15), 4.46 (dd, 1H, $J_{14,13}$=8.0 Hz, $J_{14,NH}$=4.5 Hz, H-14), 3.77~3.71 (m, 10H, H-2, H-3, H-4, H-5, H-6), 3.66 (t, 2H, J7,8=5.2 Hz, H-7), 3.54 (t, 2H, J1,2=5.0 Hz, H-1), 3.43 (t, 2H, H-8), 3.37 (dt, 1H, $J_{13,12}$=4.9 Hz, H-13), 3.03 (dd, 1H, $J_{16a,16b}$=13.0 Hz, H-16a), 2.82 (d, 1H, H-16b), 2.31 (t, 2H, J9,10=7.3 Hz, H-9). 1.72 (m, o.l., H-12a), 1.68 (m, o.l., H-10), 1.63 (m, o.l., H-12b), 1.46 (m, 2H, H-11); $^{13}$C NMR (150 MHz; $D_2O$): 69.4, 69.3, 69.3, 69.2, 69.0 (C-2, C-3, C-4, C-5, C-6), 68.6 (C-7), 61.8 (C-14), 60.0 (C-15), 55.1 (C-13), 49.9 (C-1), 39.4 (C-16), 38.6 (C-8), 35.2 (C-9), 27.6 (C-11), 27.4 (C-12), 24.8 (C-10).

Example 2—2AB Derivatization of Trisaccharide Model Compounds

Scheme 2

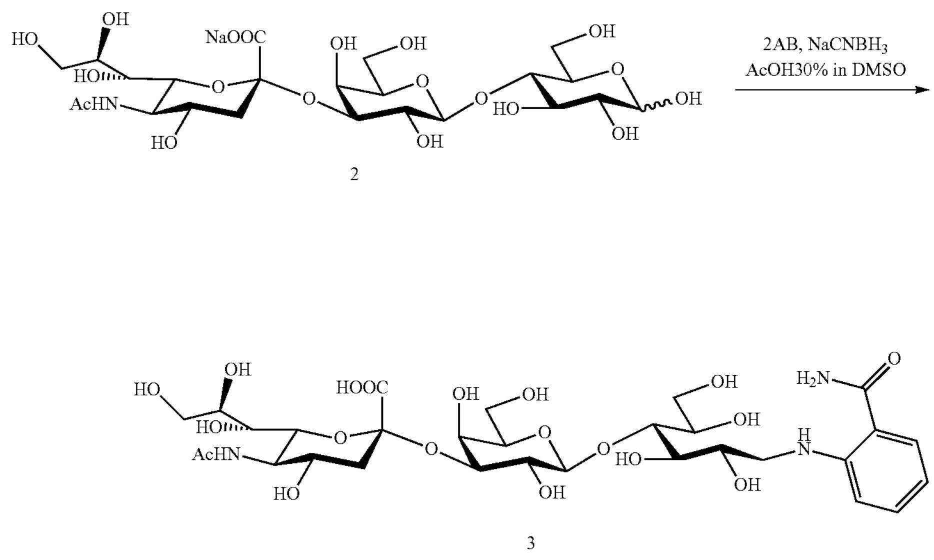

2

3

Chemical Formula: $C_{30}H_{47}N_3O_{19}$
Exact Mass: 753.2804

Scheme 2 shows 2AB derivatization of trisaccharide model compounds. To a mixed solvent of AcOH (0.9 mL) and DMSO (2.1 mL), $NaCNBH_3$ (144 mg, 2.29 mmol) and 2-AB (2-amino benzoamide, 120 mg, 0.88 mmol) was added. Trisaccharide 2 (60 mg, 0.092 mmoL) was added to the flask and the reaction was heated at 60° C. for 4.5 hrs. Reaction mixture was cooled down to room temperature and a mixture solvent of TEA (0.1 mL) and MeCN (40 mL) were added. Product that precipitated out during shaking and supernatant was removed. Each 10 mg reaction mixture was dissolved in 0.3 mL water and loaded onto Sep-Pak C18 cartridge (3 cc, 500 mg). Cartridge was eluted with water (3 mL), 5% MeCN in water (5 mL), and 10% MeCN in water (3 mL). The product was in the 5% MeCN in water eluent. Trisaccharide 3 (46 mg) was isolated and the yield is 67%. $^1$H NMR (400 MHz, $D_2O$) δ 7.55 (m, 1H, Harom), 7.44 (m, 1H, Harom), 6.91 (m, 1H, Harom), 6.78 (m, 1H, Harom), 4.53 (d, 1H, $J_{1,2}$=7.9 Hz, H-1II), 4.09 (m, o.l., H-2I), 4.06 (dd, o.l., $J_{3,4}$=3.1 Hz, $J_{3,2}$=9.7 Hz, H-3II) 3,92 (m, o.l., H-5I), 3.91 (m, o.l. H-4II), 3.90 (m, o.l., H-41), 3.87 (m, o.l., H-5II), 3,85 (m, o.l., H-9aIII), 3.83 (m, o.l., H-3I), 3.83 (m, o.l., H-5III), 3.82 (m, o.l., H-6a1), 3.72 (m, o.l., H-6b1), 3,65 (m, o.l., H-4III), 3.63 (m, o.l., H-7III), 3,61 (m, o.l., H-9bIII, H-6aII, in this sequence), 3.58 (m, o.l., H-6III, H-6bII, in this order), 3.57 (m, o.l., H-8III), 3.55 (m, o.l., H-2II), 3.44 (dd, 1H, $_{J1a\text{-}1b}$=12.8 Hz, $J_{1a\text{-}2}$=4.4 Hz, H-1aI), 3.19 (dd, 1H, $J_{1b\text{-}a}$=8.2 Hz, H-1bI), 2.74 (dd, 1H, $_{J3ax\text{-}3eq}$=12.0 Hz, $J_{4\text{-}3eq}$=4.7 Hz, H-3eqIII), 2.01 (s, 3H, $NHCOCH_3$), 1.77 (t, 1H, $J_{3ax\text{-}4}$=12.0 Hz, H-3axIII); $^{13}$C NMR (100 MHz, $D_2O$) δ 133.4, 128.8, 116.5, 112.9 (Carom), 102.6 (C-1II), 99.4 (C-2III), 79.2 (C-4I), 75.3 (C-3II), 74.4 (C-6III), 72.6 (C-7III), 71.5 (C-5II), 70.8 (C-4II), 70.4 (C-3I), 69.6 (C-2I), 69.1 (C-2II), 68.0 (C-8III), 67.8 (C-4III), 67.0 (C-5I), 62.3 (C-9III), 61.7 (C-6I), 60.4 (C-6II), 51.4 (C-5III), 45.2 (C-1I), 39.4 (C-3III), 21.7 ($NHCOCH_3$). Spectra and results are shown in FIGS. 5-10 of U.S. Provisional Application 63/010,499, filed on Apr. 15, 2020, which is incorporated by reference as if expressed in its entirety herein.

Scheme 3

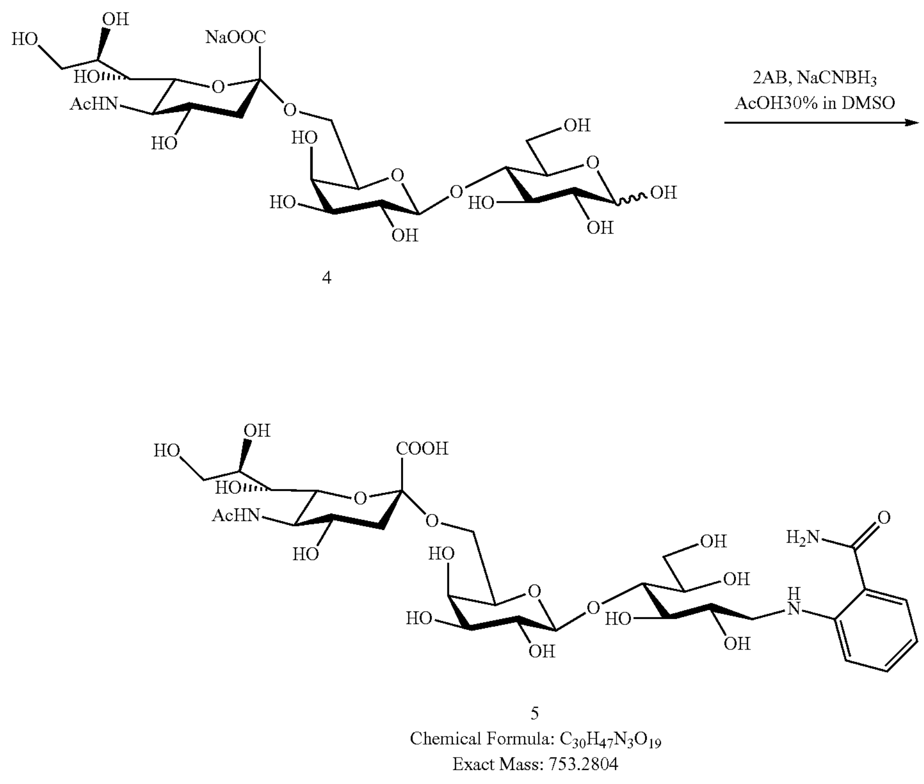

4

5

Chemical Formula: $C_{30}H_{47}N_3O_{19}$
Exact Mass: 753.2804

Trisaccharide 5 was synthesized from trisaccharide 4 in 80% in the same way as described for the synthesis of trisaccharide 3. $^1$H NMR (400 MHz, $D_2O$) δ 7.54 (m, 1H, Harom), 7.45 (m, 1H, Harom), 6.95 (m, 1H, Harom), 6.77 (m, 1H, Harom), 4.45 (d, 1H, J1,2=7.8 Hz, H-1II), 4.09 (m, 1H, H-2I), 3,90 (m, o.l., H-5I, H-4I, H-4II, in this order), 3.86 (m, o.l., H-3I), 3.83 (m, o.l., H-6aII), 3.79 (m, o.l., H-6aI), 3.78 (m, o.l., H-8III), 3,75 (m, o.l., H-9aIII), 3.73 (m, o.l., H-5III), 3.69 (m, o.l., H-5II), 3.68 (m, o.l., H-6bI), 3.64 (m, o.l., H-6bII), 3.63 (m, o.l, H-3II), 3,66 (m, o.l., H-9bIII), 3,61 (m, o.l., H-4III), 3.59 (m, o.l., H-6III), 3.53 (m, o.l., H-7III), 3.52 (m, o.l., H-2II), 3.47 (dd, o.l., $J_{1a\text{-}1b}$=13.3 Hz, $J_{1a\text{-}2}$=4.2 Hz, H-1aI), 3.32 (dd, 1H, $J_{1b\text{-}2}$=7.3 Hz, H-1bI), 2.59 (dd, 1H, $J_{3ax\text{-}3eq}$=12.0 Hz, J4-3 eq=4.6 Hz, H-3eqIII), 2.00 (s, 3H, $NHCOCH_3$), 1.50 (t, 1H, J3ax-4=12.0 Hz, H-3axIII); $^{13}$C NMR (100 MHz, $D_{cxxz}O$) δ 134.2, 129.6, 117.0, 113.5 (Carom), 103.5 (C-1II), 100.7 (C-2III), 80.1 (C-4I), 73.9 (C-5II), 72.8 (C-3II), 73.0 (C-6III), 72.1 (C-8III), 71.7 (C-4II), 71.4 (C-7III), 71.1 (C-3I), 70.3 (C-2I), 68.9 (C-5I), 68.6 (C-2II, C-4III), 63.5 (C-6II), 62.9 (C-9III), 62.4 (C-6I), 52.1 (C-5III), 45.7 (C-1I), 40.2 (C-3III), 22.4 ($NHCOCH_3$). Spectra and results are in FIGS. 11-16 of U.S. Provisional Application 63/010,499, filed on Apr. 15, 2020, which is incorporated by reference as if expressed in its entirety herein.

Example 3—Lactone Formation on 2,3 Linked Trisaccharide Model Compound From the First Amidation Reaction Scheme 4

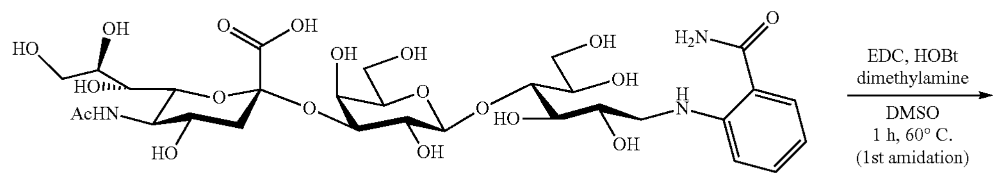

5

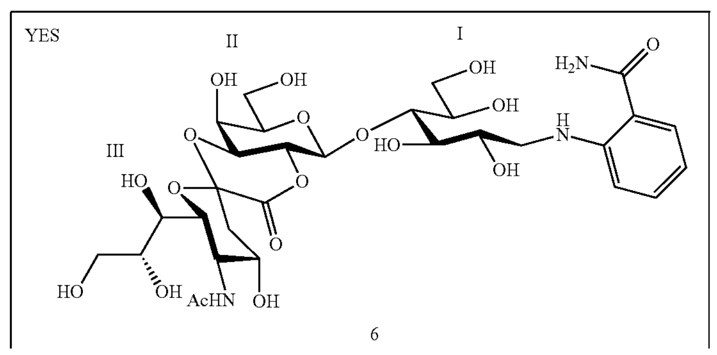

6

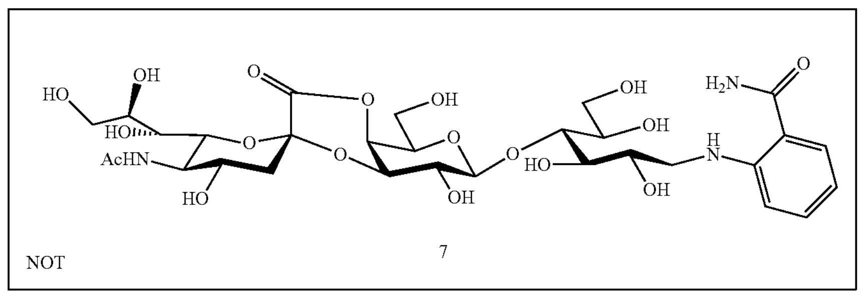

7

A mixture of EDC (1-(3-Dimethylaminopropyl)-3-ethylcarbodiimide, 11 μL, 1.94 mg, 62.5 μmol), HOBt (1-Hydroxybenzotriazole hydrate, about 20% wt water, 21.5 mg, 125 μmol), dimethyl amine (40% wt in water, 7.85 uL, 0.56 mg, 62.5 μmol) in DMSO (250 μL) was added into a flask contain trisaccharide 3 (2.5 mg, 3.32 μmol). Reaction flask was heated up at 60° C. for 1 h. Reaction mixture was placed in speed vac at r.t. for 4 hrs to remove low boiling component EDC and dimethylamine. Then 1 mL MeCN was added to precipitate out the product. The precipitate was dried in speed vac at r.t. for 1 h, and dissolved in d6DMSO for NMR acquisition. As from H-NMR, the conversion from 5 to 6 is quantitative. Compound 6 decomposed in aqueous solvent. Therefore, no purification was performed. $^1$H NMR (600 MHz, DMSO-d6) δ 8.12 (t, o.l., JNH, 1=4.6 Hz, NHI), 8.03 (d, 1H, JNH, 5=7.9 Hz, NHIII), 7.81 (m, 1H, Harom), 7.31 (m, 1H, Harom), 6.69 (m, 1H, Harom), 6.48 (m, 1H, Harom), 5.09 (d, J=5.0 Hz, OH-4II), 4.77 (dd, 1H, $J_{1,2}$=7.7 Hz, $J_{3,2}$=10.0 Hz, H-2II), 4.73 (d, 1H, H-1II), 4.62 (d, o.l., J=5.5 Hz, OH-8III), 4.46 (m, 2H, OH-2I, OH-3I), 4.13 (m, o.l., H-4III, OH-5I), 3.96 (dd, $J_{3,4}$=2.6 Hz, H-3II), 3.94 (m, o.l., OH-6II), 3.87 (m, o.l., H-2I), 3.84 (m, o.l. H-4II), 3.74 (m, o.l., H-4I), 3.72 (m, o.l., H-5I), 3.69 (m, o.l., H-5II), 3.60 (m, o.l., H-6I, H-5III, in this order), 3.54 (m, o.l., H-6aII), 3.50 (m, o.l., H-3I), 3.46 (m, o.l., H-6bII), 3.49 (m, o.l., H-6III), 3.38 (m, o.l., H-9III), 3.37 (m, o.l., H-7III), 3.25 (m, o.l., H-8III), 3.20 (m, o.l., H-1aI), 3.10 (ddd, o.l., J1a-1b=12.5 Hz, J2-1b=6.8 Hz, H-1bI), 2.37 (dd, 1H, $J_{3ax\text{-}3eq}$=12.8 Hz, $J_{4\text{-}3eq}$=4.9 Hz, H-3eqIII), 1.88 (s, 3H, $NHCOCH_3$), 1.52 (t, 1H, $J_{3ax\text{-}4}$=12.2 Hz, H-3axIII); $^{13}$C NMR (150 MHz, DMSO-d6) δ 124.4, 123.0, 117.9, 110.9 (Carom), 98.4 (C-1II), 78.6 (C-4I), 75.0 (C-3II), 75.1 (C-6III), 73.7 (C-2II), 72.9 (C-7III), 70.6 (C-5I, C-5II), 70.2 (C-3I), 69.3 (C-2I), 64.7 (C-4II), 68.2 (C-8III), 65.8 (C-4III), 63.3 (C-9III), 62.2 (C-6I), 59.8 (C-6II), 51.7 (C-5III), 44.5 (C-1I), 41.1 (C-3III), 22.6 ($NHCOCH_3$). Results and spectra shown in Tables 1-2 below and FIGS. 17-20 of U.S. Provisional Application 63/010,499, filed on Apr. 15, 2020, which is incorporated by reference as if expressed in its entirety herein. This proved that it is 2,2 lactone 6, not 2,4 lactone 7. The assignment of H-$2^{II}$ agree with reference[2]. See also e.g., underlined entries in Table 1.

TABLE 1

| $^{1}$H-NMR assignments of amide 8 and lactone 6. H-2[11] move downfield in lactone as compared to amide (3.61 in amide → 4.77 in lactone) | | | | | | | | | | |
|---|---|---|---|---|---|---|---|---|---|---|
| | | H-1 | H-2 | H-3 | H-4 | H-5 | H-6 | H-7 | H-8 | H-9 |
| I | Amide 8 | 3.49, 3.25 | 4.14 | 3.86 | 3.96 | 3.88 | 3.87, 3.76 | NA | NA | NA |
| | Lactone 6 | 3.20, 3.10 | 3.87 | 3.50 | 3.74 | 3.72 | 3.60 | NA | NA | NA |
| | Lactone 6 NH/OH | 8.12 | 4.46 | 4.46 | NA | 4.13 | | NA | NA | NA |
| II | Amide 8 | 4.60 | 3.61 | 4.06 | 3.93 | 3.96 | 3.64 | NA | NA | NA |
| | Lactone 6 | 4.73 | 4.77 agree with refrence[2] | 3.96 J = 2.6, 10.2 | 3.84 | 3.69 Cozy with H-4 | 3.54, 3.46 | NA | NA | NA |
| | Lactone 6 NH/OH | NA | NA | NA | 5.09 | NA | 3.94 | NA | NA | NA |
| III | amide | NA | NA | 1.94, 2.81 | 3.75 | 3.92 | 3.64 | 3.75 | 3.68 | 3.70, 3.67 |
| | Lactone 6 | NA | NA | 1.52, 2.37 | 4.13 | 3.60 | 3.49 | 3.37 | 3.25 | 3.38 |
| | Lactone 6 NH/OH | NA | NA | NA | | 8.03 (d, 1H, J = 7.9) | NA | | 4.62 | |

TABLE 2

| $^{13}$C-NMR assignments of amide 8 and lactone 6 | | | | | | | | | | |
|---|---|---|---|---|---|---|---|---|---|---|
| | | C-1 | C-2 | C-3 | C-4 | C-5 | C-6 | C-7 | C-8 | C-9 |
| I | amide | 45.8 | 70.2 | 71.1 | 79.8 | 71.1 | 62.3 | NA | NA | NA |
| | Lactone | 44.5 | 69.3 | 70.2 | 78.6 | 70.6 | 62.2 | NA | NA | NA |
| II | amide | 103.0 | 69.7 | 75.7 | 68.4 | 71.5 | 61.0 | NA | NA | NA |
| | Lactone | 98.4 | 73.7 | 75.0 | 64.7 | 70.6 | 59.8 | NA | NA | NA |

TABLE 2-continued

| $^{13}$C-NMR assignments of amide 8 and lactone 6 | | | | | | | | | | |
|---|---|---|---|---|---|---|---|---|---|---|
| | | C-1 | C-2 | C-3 | C-4 | C-5 | C-6 | C-7 | C-8 | C-9 |
| III | amide | NA | NA | 39.0 | 67.4 | 51.8 | 74.9 | 74.0 | 67.9 | 63.3 |
| | Lactone | NA | NA | 41.1 | 65.8 | 51.7 | 75.1 | 72.9 | 68.2 | 63.3 |

Example 4—AA Reaction on 2,3 Linked Trisaccharide Model Compound

Scheme 5

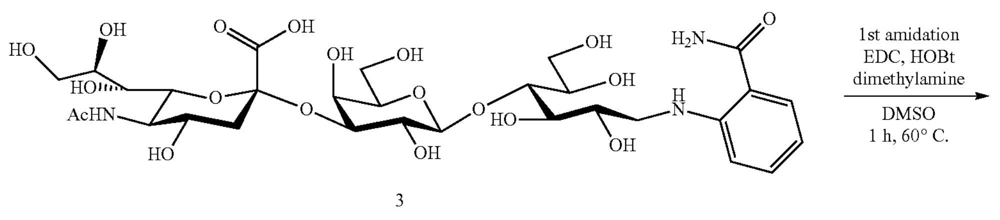

3

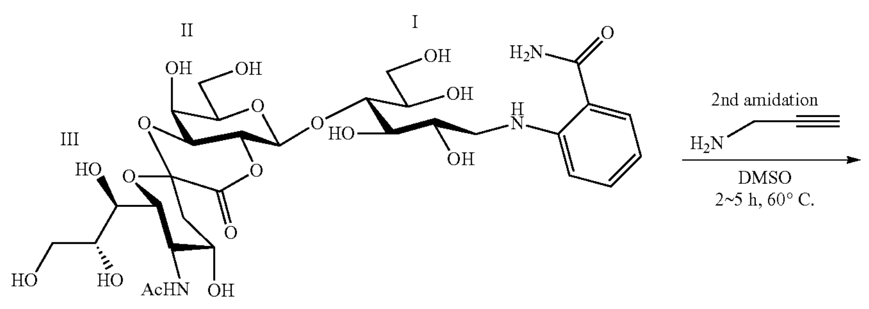

6

-continued

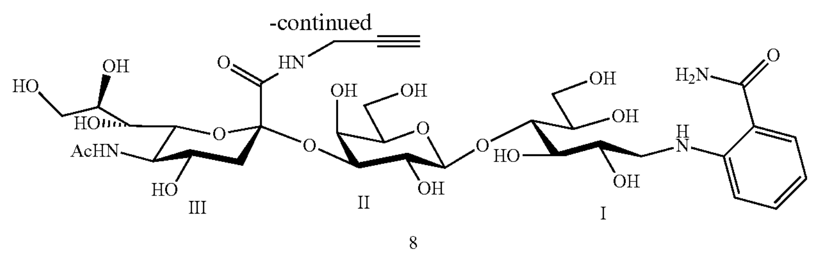

8

The first step (amidation): A mixture of EDC (1-(3-Dimethylaminopropyl)-3-ethylcarbodiimide, 88 μL, 77.6 mg, 0.5 mmol), HOBt (1-Hydroxybenzotriazole ~20% wt water, 172 mg, 1 mmol), dimethyl amine (40% wt in water, 62.8 uL, 22.4 mg, 0.5 mmol) in DMSO (2 mL) was added into a flask contain trisaccharide 3 (20 mg, 25.56 μmol). Reaction flask was heated up at 60° C. for 1 h. The second step (amidation): without any purification, the second step reagent propargyl amine (0.8 mL) was added into the first step n reaction mixture. Reaction was heated up at 60° C. for 5 hrs. Reaction mixture was placed in speed vac for 1 day at r.t. until around 1 mL volume left. MeCN (10 mL) was added and the product was precipitate out. Precipitates was collected and washed with MeCN (10 mL) for 3 times. Each 10 mg reaction mixture was dissolved in 0.3 mL water and loaded onto Sep-Pak C18 cartridge (3 cc, 500 mg). Cartridge was eluted with water (3 mL), 5% MeCN in water (3 mL), and 10% MeCN in water (4 mL), and 25% MeCN in water (3 mL). The product was in the 10% MeCN in water eluent. Amide 8 (16.8 mg) was isolated and the yield was 80%. $^1$H NMR (600 MHz, $D_2O$) δ 7.60 (m, 1H, Harom), 7.48 (m, 1H, Harom), 6.96 (m, 1H, Harom), 6.83 (m, 1H, Harom), 4.60 (d, 1H, J1,2=7.89 Hz, H-1II), 4.14 (ddd, 1H., $J_{1a2}$=4.0 Hz, $J_{1b-2}$=8.2 Hz, 4, $J_{2,3}$=8.2 Hz, H-2I), 4.06 (m, o.l., H-3II, $CH_2CCH$, in this order), 3.96 (m, o.l., H-5II), 3.96 (m, o.l., H-5II, H-4I, in this order), 3.93 (m, o.l. H-4II), 3.92 (m, o.l., H-5III), 3.88 (m, o.l., H-5I), 3.87 (m, o.l., H-6aI), 3.86 (m, o.l., H-3I), 3.76 (m, o.l., H-6bI), 3,75 (m, o.l., H-4III), 3.75 (m, o.l., H-7III), 3.70 (m, o.l., H-9aIII), 3.67 (m, o.l., H-9bIII), 3.64 (m, o.l., H-6aII, H-6bII, H-6III, in this order), 3.68 (m, o.l., H-8III), 3.61 (m, o.l., H-2II), 3.49 (dd, 1H, J1a-1b=13.0 Hz, H-1aI), 3.25 (dd, 1H, H-1bI), 2.81 (dd, 1H, $J_{3ax-3eq}$=12.8 Hz, $J_{4-3eq}$=4.6 Hz, H-3eqIII), 2.74 (s, 1H, CCH), 2.06 (s, 3H, $NHCOCH_3$), 1.94 (t, 1H, $J_{3ax-4}$=12.8 Hz, H-3axIII); $^{13}$C NMR (150 MHz, $D_2O$) δ 133.9, 129.4, 117.1, 113.5 (Carom), 103.0 (C-1II), 79.8 (C-4I), 75.7 (C-3II), 74.9 (C-6III), 74.0 (C-7III), 71.1 (C-5II), 71.1 (C-3I, C-5I), 70.2 (C-2I), 69.7 (C-2II), 68.4 (C-4II), 67.9 (C-8III), 67.4 (C-4III), 63.3 (C-9III), 62.3 (C-6I), 61.0 (C-6II), 51.8 (C-5III), 45.8 (C-1I), 39.0 (CCH), 38.2 (C-3III), 29.1 ($CH_2CCH$), 22.3 ($NHCOCH_3$). The assignment of the sialic acid-alkyne amide (ring III) agreed with the published assignment[3].

Optimization of the second step: For a 1 mg scale reaction, 2 h heating gave quantitative conversion. For a larger scale (20 mg), 5 h was needed to push the reaction to completion. For the AA reaction on slide, as the over carbohydrate loading on one FFPE slide is way less than 1 mg, the second step was performed for 2 h. The reaction was checked by taking the part of the reaction mixture here and it was precipitated with MeCN. The $^1$H-NMR data of the crude reaction mixture in $D_2O$ was acquired. The propargly amine amount was the results of a balance between proper viscosity or the reaction efficiency. For doing AA reaction on FFPE tissue, the reaction mixture needs to maintain certain viscosity to stay on top of the tissue. The more propargly amine was added, the less viscose the propargly-DMSO mixture is. The more propargly amine was used, the faster the reaction is. For propargly amine, propargly amine-DMSO was used at a 2/5 ratio. Results and spectra are shown in FIGS. 21-24 of U.S. Provisional Application 63/010,499, filed on Apr. 15, 2020, which is incorporated by reference as if expressed in its entirety herein.

Example 5—AA Reaction on 2,6 Linked Trisaccharide Model Compound

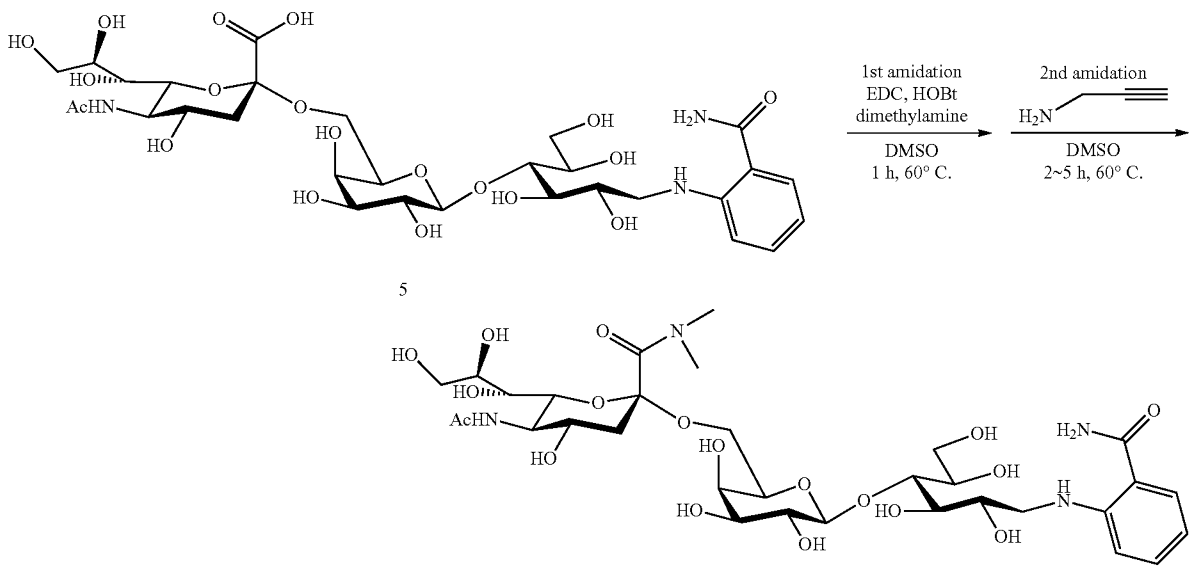

5

9

Amide 9 was synthesized from trisaccharide 5, by applying the same first amidation and second amidation one after another as for the synthesis of amide 8 (Scheme 5). Same workup and purification methods was used. Crude NMR showed quantitative conversion. Isolated yield of compound 9 was about 80%.

$^1$H NMR (600 MHz, $D_2O$) δ 7.60 (m, 1H, Harom), 7.48 (m, 1H, Harom), 6.94 (m, 1H, Harom), 6.82 (m, 1H, Harom), 4.52 (d, 1H, $J_{1,2}$=7.7 Hz, H-1II), 4.12 (m, 1H., H-2I), 3.97 (m, o.l., H-4II, H-5I), 3,96 (m, o.l., H-4III), 3.93 (m, o.l., H-6aI), 3,90 (m, o.l., H-4I), 3.88 (m, o.l., H-3I), 3.83 (m, o.l., H-6aII), 3.86 (m, o.l., H-6bI), 3.82 (m, o.l., H-5III), 3.81 (m, o.l., H-5II), 3,75 (m, o.l., H-9aIII), 3.73 (m, o.l., H-8III), 3,68 (m, o.l., H-9bIII), 3.65 (m, o.l., H-3II, H-6bII, in this order), 3.59 (dd, 1H, J2,3=9.9 Hz, H-2II), 3.54 (m, o.l., H-7III), 3.51 (m, o.l., H-6III), 3.50 (m, o.l., H-1aI), 3.22 (dd, 1H, J1b-2=8.0 Hz, H-1bI), 3.25 (s, 3H, $NCH_3$), 2.85 (s, 3H, $NCH_3$), 2.41 (dd, 1H, $J_{3ax-3eq}$=12.6 Hz, $J_{4-3eq}$=4.9 Hz, H-3eqIII), 2.04 (s, 3H, $NHCOCH_3$), 1.63 (dd, 1H, $J_{3ax-4}$=11.4 Hz, H-3axIII); $^{13}$C NMR (150 MHz, $D_2O$) δ 133.5, 129.0, 116.3, 112.7 (Carom), 102.6 (C-1II), 78.2 (C-4I), 73.3 (C-5II), 72.2 (C-3II), 72.2 (C-6III), 70.8 (C-4III, C-3I, in this order), 70.7 (C-2II), 69.9 (C-8III), 69.8 (C-2I), 68.2, 67.8 (C-4II or C-5I), 67.6 (C-7III), 62.9 (C-6II), 61.7 (C-9III), 61.5 (C-6I), 51.5 (C-5III), 44.9 (C-1I), 37.4 ($NCH_3$), 36.8 (C-3III), 36.5 ($NCH_3$), 21.8 ($NHCOCH_3$).

To prove the reaction mechanism, the reaction was worked-up and purification was performed after the first amidation. The same amide 9 was yielded, which means that amide 9 already formed after the first amidation. Isolated pure amide 9 was added into propargyl amine-DMSO (at a 2/5 ratio, v/v) and heated at 60° C. for 5 h. The amide 9 did not change. Here it was demonstrated that the AA reaction will not label 2,6 sialic acid with alkyne, but at the same time, will label 2,3 sialic acid with an alkyne functionality.

Results and spectra are shown in Tables 3-4 below and FIGS. 25-28 of U.S. Provisional Application 63/010,499, filed on Apr. 15, 2020, which is incorporated by reference as if expressed in its entirety herein.

TABLE 3

$^1$H-NMR assignments of amide 9

| | H-1 | H-2 | H-3 | H-4 | H-5 | H-6 | H-7 | H-8 | H-9 |
|---|---|---|---|---|---|---|---|---|---|
| I | 3.50, 3.22 | 4.12 | 3.88 | 3.90 | 3.97 | 3.93, 3.86 | NA | NA | NA |
| II | 4.52 | 3.59 | 3.65 | 3.97 | 3.81 | 3.80, 3.65 | NA | NA | NA |
| III | NA | NA | 1.63, 2.41 | 3.96 | 3.82 | 3.51 | 3.54 | 3.73 | 3.75, 3.68 |

TABLE 4

$^{13}$C-NMR assignments of amide 9

| | C-1 | C-2 | C-3 | C-4 | C-5 | C-6 | C-7 | C-8 | C-9 |
|---|---|---|---|---|---|---|---|---|---|
| I | 44.9 | 69.8 | 70.8 | 78.2 | 68.2 or 67.8 | 61.5 | NA | NA | NA |
| II | 102.6 | 70.7 | 72.2 | 68.2 or 67.8 | 73.3 | 62.9 | NA | NA | NA |
| III | NA | | 36.8 | 70.8 | 51.5 | 72.2 | 67.8 | 69.9 | 61.7 |

Scheme 7

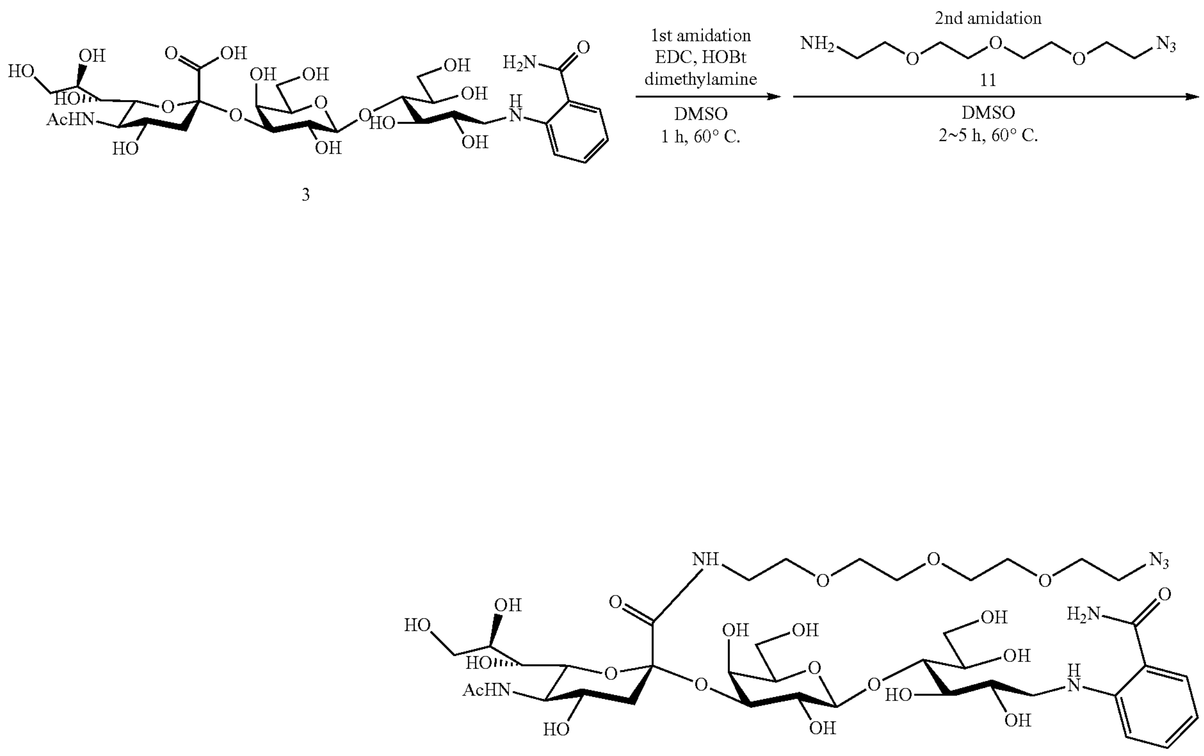

3

11

10

To prove the AA labeling method for 2,3 sialic acid are not limited to alkyne, amide 10 was synthesized (Scheme 7). The synthesis of amide 10 is the same as amide 8 but for two differences. For the 2nd amidation, the propargyl amine was replaced with the amine 11 (Scheme 7) and for purification, amide 10 was eluted in 25% MeCN in water. In comparison, amide 8 was eluted in 10% MeCN in water (Scheme 6). The conversion yield of 3→10 is quantitative as judged by crude mixture before cartridge purification. The isolated yield of amide 10 was about 80%.

Here, it was demonstrated that not only alkyne but also other functionalities can be installed into the 2,3 sialic acid with the AA methods described and demonstrated herein. It will be appreciated that some functionalities can be preferred in certain contexts. For example, the alkyne functionality was not selected for further experiments as propargyl amine much more affordable than amide 11. However, it will be appreciated that for other contexts, it is appropriate to proceed with other functionalities such as alkynes.

$^{1}H$ NMR (600 MHz, $D_2O$) δ 7.61 (m, 1H, Harom), 7.49 (m, 1H, Harom), 6.96 (m, 1H, Harom), 6.83 (m, 1H, Harom), 4.60 (d, 1H, J1,2=7.8 Hz, H-1II), 4.14 (m, 1H., H-2I), 4.07 (dd, 1H, J3,2=9.7 Hz, J3,4=3.1 Hz, H-3II), 3.97 (m, o.l., H-5II), 3.96 (m, o.l., H-4I), 3.93 (m, o.l., H-5III), 3.92 (m, o.l. H-4II), 3.88 (m, o.l., H-3I), 3.87 (m, o.l., H-6aI), 3.83 (m, o.l., H-5I), 3.78 (m, o.l., H-4III), 3.77 (m, o.l., H-7III), 3.76 (m, o.l., H-6bI), 3.75-3.67 (m, o.l., $CH_2$ (linker)×12), 3.70 (m, o.l., H-9aIII), 3.67 (m, o.l., H-9bIII), 3.65 (m, o.l., H-6aII, H-6bII), 3.64 (m, o.l., H-6III), 3.65 (m, o.l., H-8III), 3.62 (dd, 1H, H-2II), 3.52 (m, o.l., $CH_2N_3$×2), 3.50 (m, o.l., $CH_2NH_2$×2), 3.49 (m, al., H-1aI), 3.25 (dd, 1H, $J_{1a-1b}$=13.1 Hz, $J_{2-1b}$=7.9 Hz, H-1bI), 2.78 (dd, 1H, $J_{3ax-3eq}$=12.8 Hz, $J_{4-3eq}$=4.3 Hz, H-3eqIII), 2.06 (s, 3H, $NHCOCH_3$), 1.96 (t, 1H, $J_{3ax-4}$=12.4 Hz, H-3axIII); $^{13}C$ NMR (150 MHz, $D_2O$) δ 134.0, 129.4, 117.0, 113.4 (Carom), 103.0 (C-1II), 79.7 (C-4I), 75.7 (C-3II), 74.8 (C-6III), 74.0 (C-7III), 71.5 (C-5II), 71.4 (C-3I), 71.1 (C-5I), 70.2 (C-2I), 69.9, 69.8, 69.8 ($CH_2O$ (Linker)×3), 69.7 (C-2II), 69.5, 69.5, 68.7 ($CH_2O$ (Linker)×3), 68.4 (C-4II), 68.0 (C-8III), 67.5 (C-4III), 63.3 (C-9III), 62.3 (C-6I), 60.8 (C-6II), 51.9 (C-5III), 50.4 ($CH_2N_3$), 45.7 (C-1I), 39.2 ($CH_2NH$), 37.9 (C-3III), 22.3 ($NHCOCH_3$). Results and spectra are shown in Tables 5-6 below and FIGS. 29-32 of U.S. Provisional Application 63/010,499, filed on Apr. 15, 2020, which is incorporated by reference as if expressed in its entirety herein.

TABLE 5

| $^{1}H$-NMR assignments of amide 10 | | | | | | | | | |
|---|---|---|---|---|---|---|---|---|---|
| | H-1 | H-2 | H-3 | H-4 | H-5 | H-6 | H-7 | H-8 | H-9 |
| I | 3.49, 3.25 | 4.14 | 3.88 | 3.96 | 3.83 | 3.87, 3.76 | NA | NA | NA |
| II | 4.60 | 3.61 | 4.07 | 3.92 | 3.97 | 3.65 | NA | NA | NA |
| III | NA | NA | 1.96, 2.78 | 3.78 | 3.93 | 3.64 | 3.77 | 3.65 | 3.70, 3.67 |

TABLE 6

| $^{13}C$-NMR assignments of amide 10 | | | | | | | | | |
|---|---|---|---|---|---|---|---|---|---|
| | C-1 | C-2 | C-3 | C-4 | C-5 | C-6 | C-7 | C-8 | C-9 |
| I | 45.7 | 70.2 | 71.4 | 79.7 | 71.1 | 62.3 | NA | NA | NA |
| II | 103.0 | 69.7 | 75.7 | 68.4 | 71.5 | 60.8 | NA | NA | NA |
| III | NA | | 37.9 | 67.5 | 51.9 | 74.8 | 74.0 | 68.0 | 63.3 |

Example 6—Lactone Formation on 2,8 Linked Poly Sialic Acid With the First Amidation Scheme 8

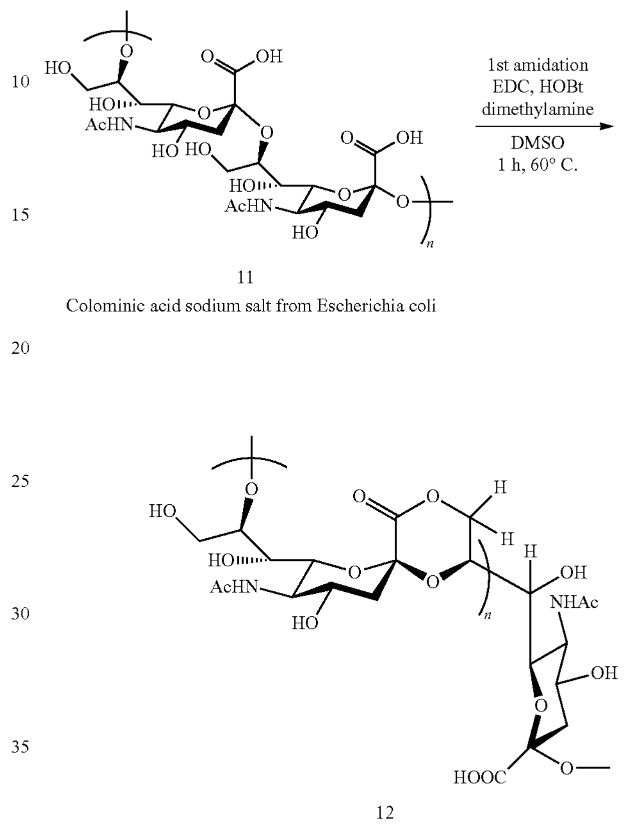

11

Colominic acid sodium salt from Escherichia coli

12

As poly sialic acid lactone 12 was reported[4-8], it was investigated whether or not the AA method could apply to poly sialic acid. The first amidation reaction was applied to compound 11 as shown in Scheme 8. A reagents mixture contained 1 mL DMSO, EDC (44 μL, 38.8 mg, 0.25 mmol, 0.25M), HOBt (1-Hydroxybenzotriazole hydrate, about 20% wt water, 86 mg, 0.5 mmol, 0.5M), and dimethylamine (40% wt in water, 31.4 uL, 11.2 mg, 0.25 mmol, 0.25M). Colomimic acid (10 mg, 31.85 μmol disaccharide repeating unit). Reaction was heated at 60° C. for 1 h. Reaction mixture was placed in speed vac at r.t. for 2 hr. MeCN was used for precipitate and wash the crude product. After drying in speed vac, crude product was dissolved in DMSO-d6 for NMR acquisition. Lactone 12 was not stable in aqueous solvent. No cartridge purification was performed.

$^{1}H$ NMR (600 MHz; DMSO-d6): 8.23 (bs, 1H, NH), 5.29 (bs, 1H, OH-7), 5.14 (bs, 1H, OH-4), 4.57 (m, 1H, H-9a), 4.44 (m, 1H, H-9b), 4.17 (bs, 1H, H-4), 3.99 (bs, 1H, H-8), 3.52 (bs, o.l., H-5), 3.44 (m, o.l., H-7), 3.31 (m, o.l., H-6), 2.28 (bs, 1H, H-3eq), 1.89 (bs, 3H, $NHCOCH_3$), 1.35 (bs, 1H, H-3ax); $^{13}C$ NMR (150 MHz; DMSO-d6): 72.3 (C-6), 69.2 (C-7), 69.4 (C-8), 67.4 (C-9), 65.8 (C-4), 51.4 (C-5), 40.5 (C-3), 22.0 ($NHCOCH_3$). Results and spectra are shown in FIGS. 33-35 of U.S. Provisional Application 63/010,499, filed on Apr. 15, 2020, which is incorporated by reference as if expressed in its entirety herein.

Example 7—AA Reaction on 2,8 Linked Poly Sialic Acid

Scheme 9

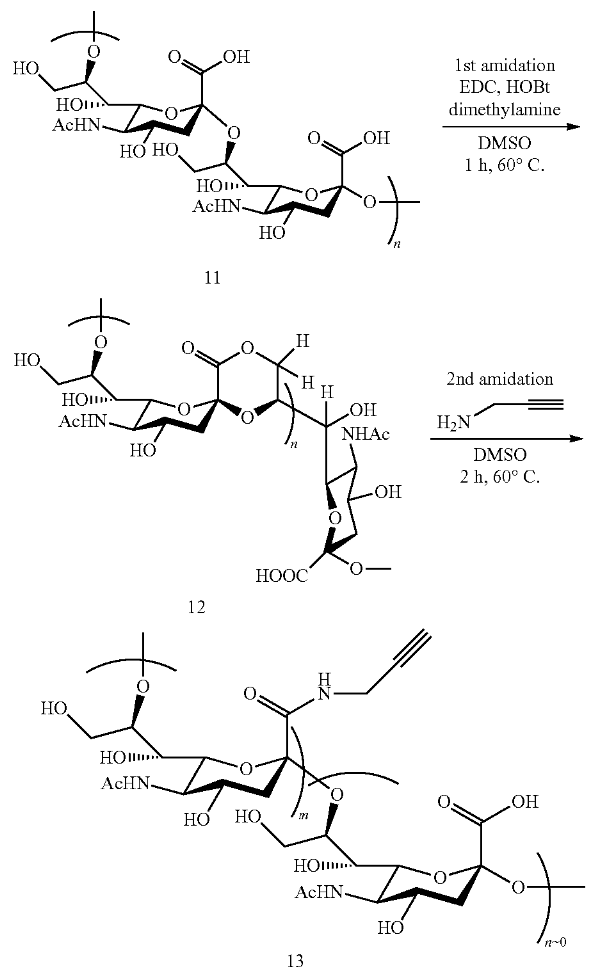

11

12

13

Next, the AA reaction was applied on poly sialic acid as shown in Scheme 9. A reagents mixture of 1 mL DMSO, EDC (44 μL, 38.8 mg, 0.25 mmol, 0.25M), HOBt (1-Hydroxybenzotriazole hydrate, about 20% wt water, 86 mg, 0.5 mmol, 0.5M), and dimethylamine (40% wt in water, 31.4 uL, 11.2 mg, 0.25 mmol, 0.25M). Colomimic acid (10 mg, 31.85 μmol disaccharide repeating unit). The reaction was heated at 60° C. for 1 h. Without any purification, the second amidation reagent propargyl amine (0.4 mL) was added. The reaction mixture was heated at 60° C. for 2 h. Workup and purification was the same as for the synthesis of amide 8. Amide 13 (3.5 mg, 33%) was eluted with 25% and 50% MeCN in water. Crude NMR showed the conversion yield of acid to amide is about 75%. $^1$H NMR (600 MHz; $D_2O$): 4.31 (m, 2H, $CH_2CCH$), 4.16 (m, 1H, H-5), 4.06 (m, o.l., H-9a), 4.03 (m, o.l., H-6), 3,90 (m, o.l., H-9b), 3.84 (m, o.l., H-8), 3,80 (m, o.l., H-4), 3.66 (m, o.l., H-7), 2.82 (m, 1H, H-3eq), 2.75 (m, 1H, CCH), 2.08 (s, 3H, $NHCOCH_3$), 2.00 (m, 1H, H-3ax); $^{13}$C NMR (150 MHz; $D_2O$): 75.8 (C-8), 75.0 (C-6), 67.1 (C-4, C-7), 61.0 (C-9), 52.8 (C-5), 40.3 (C-3), 39.4 (CCH), 29.9 ($CH_2CCH$), 23.0 ($NHCOCH_3$). Trace amount of poly sialic acid 11 was eluted in water. $^1$H NMR (600 MHz; $D_2O$): 4.23 (m, 1H, H-9a), 4.13 (m, 1H, H-8), 3.93 (m, 1H, H-6), 3.85 (m, 1H, H-5), 3,67 (m, o.l., H-9b), 3.66 (m, o.l., H-7), 3,63 (m, o.l., H-4), 2.70 (m, 1H, H-3eq), 2.11 (s, 3H, $NHCOCH_3$), 1.77 (m, 1H, H-3ax); $^{13}$C NMR (150 MHz; $D_2O$): 77.5 (C-8), 72.8 (C-7), 70.6 (C-6), 68.1 (C-4), 60.9 (C-9), 52.1 (C-5), 39.5 (C-3), 22.2 ($NHCOCH_3$). The assignments of C-7 and C-6 are reversed compared with published assignment.[6] Results and spectra are shown in FIGS. 36-44 of U.S. Provisional Application 63/010,499, filed on Apr. 15, 2020, which is incorporated by reference as if expressed in its entirety herein.

Here, it can be demonstrated that the AA labeling methods can covalently label poly sialic acid (2,8 linked) with an alkyne functionality.

Example 8—Click Chemistry on Trisaccharide Alkyne

Scheme 10
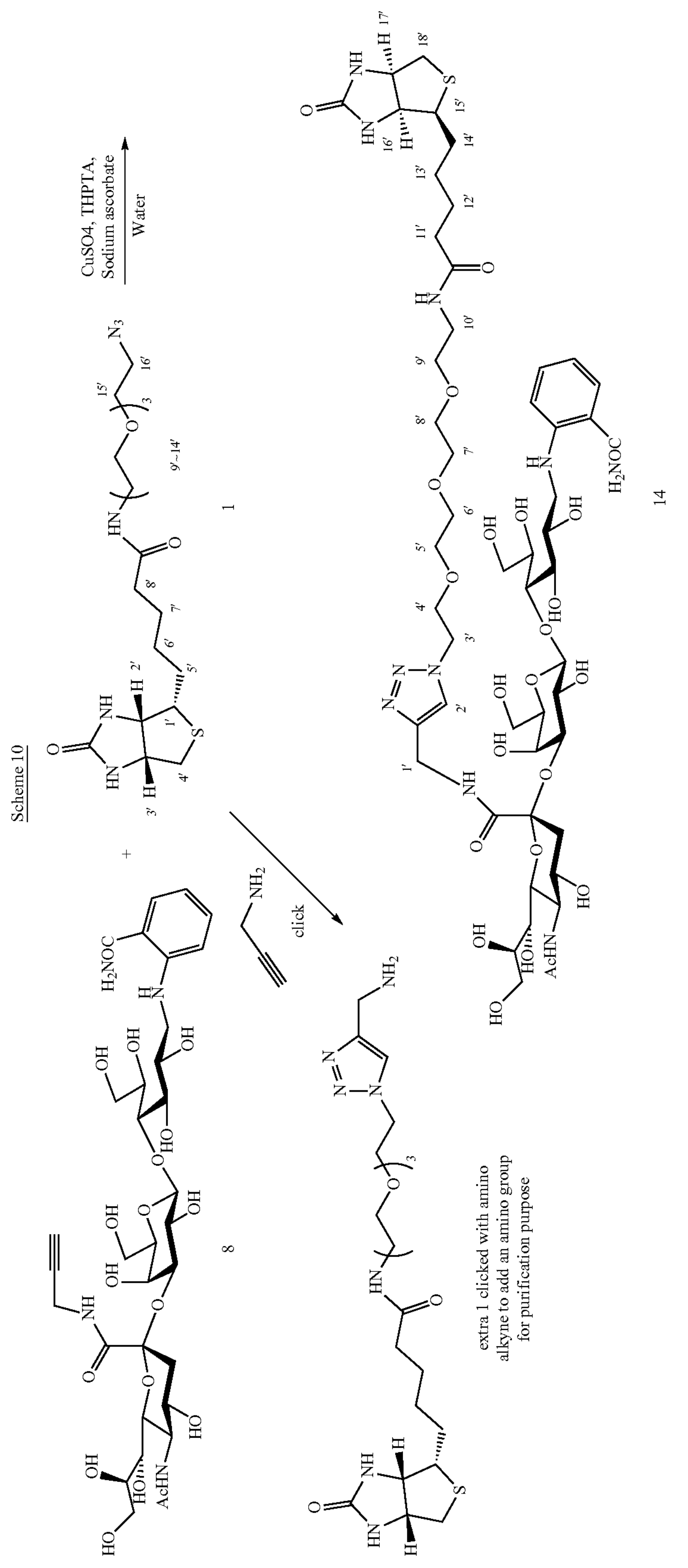

Previous examples have demonstrated that the AA method can covalently add an alkyne functionality of either 2,3 or 2,8 sialic acid. Here this example can demonstrate that the sugar alkyne is clickable. The click protocol with sodium ascorbate and THPTA (Tris(benzyltriazolylmethyl)amine) was chosen and adapted from M. G. Finn's protocol.[9] THPTA is commercially available.

Procedure: As shown in Scheme 10, add A into G. Then add B. Mix C and E separately and add the C and E mixture in to AGB mixture. Then add H, add D. Seal the reaction flask and let it sit at r.t. overnight. For the convenient of purification, 1 uL of propargyl amine (amine alkyne) into the reaction mixture and let sit at r.t. for 6 h. This step converts the azido group in compound 1 into an amine group, which helped the separation of extra biotin and compound 14. Then solvent was removed by lyophilization. Crude mixture was dissolved in water (0.6 mL) and loaded 0.2 mL onto Hypercarb Hypersep cartridge (25 mg, 1 mL, thermos scientific product #60106-304). Cartridge was eluted with 1 mL of 0%, 5%, 10%, 25%. 50%, 60%, 70% MeCN in water. Pure product 14 was eluted with 50% MeCN in water. No starting material 8 was recovered in this cartridge purification. Crude NMR shows the disappearance of the starting material 8. Conversion yield from crude NMR is quantitative. Table 7 shows reagents used.

TABLE 7

Reagent table of click reaction on amide 8

| | | MW | Reagent [C] | Exact reagent [C] in M. G. Finn's protocol Reagent [C] | Molar mmol | Reagents Stock Sin [C] | Reagent Stock Sin prep. Per 1 mL water | Volume of stock sin added |
|---|---|---|---|---|---|---|---|---|
| A | Sugar alkyne 8 | 790.31 tri | 0.39 mM | 2 fold excess as to sugar azide 6~150 μM | $2.52 \times 10^{-3}$ | 0.1 mg/μL | | 2 mg 20 μL |
| B | Biotin-azide | 356.16 | 1.17 mM | Sugar azide 2~50 μM | $7.56 \times 10^{-3}$ | 50 mM | 17.8 mg | 152 μL |
| C | CuSO4 | 159.61 | 0.1 mM | 0.1 mM | $6.46 \times 10^{-3}$ | 20 mM | 3.19 mg | 32.32 μL |
| D | Sodium ascorbate | 198.11 | 5 mM | 5 mM | $32.3 \times 10^{-3}$ | 100 mM | 20 mg | 323 μL |
| E | THPTA | 434.5 | 0.5 mM | 0.5 mM | $3.23 \times 10^{-3}$ | 50 mM | 21.725 mg | 64.6 μL |
| H | Aminoguanidine HCl | 110.55 | 5 mM | 5 mM | $32.3 \times 10^{-}$ | 100 mM | 11 mg | 323 μL |
| G | 0.1M PBS ph7 (10x PBS, 21 mg salt/mL) | | | | | | | 5.66 mL |
| | Overall Volume | | | | | | | 6.46 mL |

$^1$H NMR (600 MHz; $D_2O$): 8.05 (S, 1H, H-2'), 7.61 (m, 1H, Harom), 7.49 (m, 1H, Harom), 6.96 (m, 1H, Harom), 6.83 (m, 1H, Harom), 4.64 (m, o.l., H-3'a, H-3'b), 4.60 (m, o.l., H-17', H-1'a, in this order), 4.57 (d, o.l., $J_{1,2}$=7.9 Hz, H-1II), 4.50 (d, 1H, JH-1'a, H-1'b=15.0 Hz, H-1'b), 4.42 (dd, 1H, $J_{16',15'}$=7.9 Hz, $J_{16',NH'}$=4.3 Hz, H-16'), 4.14 (ddd, 1H., $J_{1a-2}$=4.6 Hz, J2,3=8.0 Hz, H-2I), 4.00 (m, o.l., H-3II), 3.99 (m, o.l., H-4'), 3.97 (m, o.l., H-5II), 3.96 (m, o.l., H-4I), 3.93 (m, o.l., H-5III), 3.88 (m, o.l., H-5I), 3.87 (m, o.l., H-6aI), 3.85 (m, o.l., H-3I), 3.78 (m, o.l., H-7III), 3.77 (m, o.l., H-4III, H-6bI, in this order), 3.70~3.67 (m, o.l., H-9aIII, H-9bIII), 3.71~3.61 (m, o.l., H-5', H-6', H-7', H-8'), 3.69 (m, o.l., H-8III), 3.68 (m, o.l. H-4II), 3.64 (m, o.l., H-9'), 3.62 (m, o.l., H-6aII), 3.59 (m, o.l., H-2II), 3.55 (m, o.l., H-6bII), 3.50 (m, o.l., H-1Ia), 3.49 (m, o.l., H-6III), 3.40 (t, 2H, $J_{10',9'}$=4.9 Hz, H-10'), 3.33 (dt, 1H, $J_{15',14'}$=4.7 Hz, H-15'), 3.25 (dd, 1H, $J_{1a-1b}$=13.1 Hz, $J_{1b-2}$=8.5 Hz, H-1bI), 3.00 (dd, 1H, $J_{18'a,18'b}$=13.0 Hz, $J_{18'a,17'}$=5.0 Hz, H-18'a), 2.80 (d, 1H, H-18'b), 2.80 (dd, 1H, $J_{3ax-3eq}$=12.6 Hz, $J_{4-3eq}$=4.5 Hz, H-3eqIII), 2.28 (t, 2H, J11',12'=7.4 Hz, H-11'), 2.07 (s, 3H, $NHCOCH_3$), 1.94 (t, 1H, J3ax-4=12.6 Hz, H-3axIII), 1.73 (m, al., H-14'a), 1.66 (m, al., H-12'), 1.59 (m, al., H-14b'), 1.42 (m, 2H, H-13'); $^{13}$C NMR (150 MHz; $D_2O$): 133.3, 128.6 (Carom), 122.9 (C-2'), 115.7, 112.5 (Carom), 101.9 (C-1II), 78.8 (C-4I), 74.6 (C-3II), 74.1 (C-6III), 74.1 (C-4II), 73.1 (C-7III), 70.9 (C-5II), 70.7 (C-3I), 70.5 (C-5I), 69.6 (C-2I), ~69.0 (C-5', C-6', C-7', C-8', C-9'), 69.0 (C-2II), 68.0 (C-4'), 66.6 (C-4III), 65.4 (C-8III), 62.0 (C-9III), 61.5 (C-6I), 61.3 (C-16'), 60.2 (C-6II), 59.4 (C-17'), 54.9 (C-15'), 51.1 (C-5III), 49.4 (C-3'), 45.1 (C-1I), 39.4 (C-18'), 38.4 (C-10'), 37.3 (C-3III), 35.1 (C-11'), 33.4 (C-1'), 27.4 (C-13'), 26.9 (C-14'), 24.7 (C-12'), 21.6 ($NHCOCH_3$). Results and spectra are shown in Tables 8-11 below and FIGS. 45-47 of U.S. Provisional Application 63/010,499, filed on Apr. 15, 2020, which is incorporated by reference as if expressed in its entirety herein.

Table 8: $^1$H NMR compare the trisaccharide part of trisaccharide biotin with trisaccharide alkyne.

TABLE 8

$^1$H NMR comparison of the trisaccharide part of trisaccharide biotin with a trisaccharide alkyne.

| | | H-1 | H-2 | H-3 | H-4 | H-5 | H-6 | H-7 | H-8 | H-9 |
|---|---|---|---|---|---|---|---|---|---|---|
| I | Tri-alkyne | 3.49, 3.25 | 4.14 | 3.86 | 3.96 | 3.88 | 3.87, 3.76 | NA | NA | NA |
| | Tri-biotin | 3.50, 3.25 | 4.14 | 3.88 | 3.96 | 3.85 | 3.87, 3.77 | NA | NA | NA |
| II | Tri-alkyne | 4.60 | 3.61 | 4.06 | 3.93 | 3.96 | 3.64 | NA | NA | NA |

TABLE 8-continued

| $^{1}H$ NMR comparison of the trisaccharide part of trisaccharide biotin with a trisaccharide alkyne. | | | | | | | | | | |
|---|---|---|---|---|---|---|---|---|---|---|
| | | H-1 | H-2 | H-3 | H-4 | H-5 | H-6 | H-7 | H-8 | H-9 |
| | Tri-biotin | 4.57 | 3.59 | 4.00 | 3.68 | 3.97 | 3.62, 3.55 | NA | NA | NA |
| III | Tri-alkyne | NA | NA | 2.81, 1.94 | 3.75 | 3.92 | 3.64 | 3.75 | 3.68 | 3.70, 3.67 |
| | Tri-biotin | NA | NA | 2.80, 1.94 | 3.77(first) | 3.93 | 3.49 | 3.78 | 3.69 | 3.70~3.67 |

TABLE 9

| $^{13}C$ NMR compare the trisaccharide part of trisaccharide biotin with trisaccharide alkyne | | | | | | | | | | |
|---|---|---|---|---|---|---|---|---|---|---|
| | | C-1 | C-2 | C-3 | C-4 | C-5 | C-6 | C-7 | C-8 | C-9 |
| I | Tri-alkyne | 45.8 | 70.2 | 71.1 | 79.8 | 71.1 | 62.3 | NA | NA | NA |
| | Tri-biotin | 45.1 | 69.6 | 70.5 | 78.8 | 70.7 | 61.5 | NA | NA | NA |
| II | Tri-alkyne | 103.0 | 69.7 | 75.7 | 68.4 | 71.5 | 61.0 | NA | NA | NA |
| | Tri-biotin | 101.9 | 69.0 | 74.6 | 74.1 | 70.9 | 60.2 | NA | NA | NA |
| III | Tri-alkyne | NA | NA | 39.0 | 67.4 | 51.8 | 74.9 | 74.0 | 67.9 | 63.3 |
| | Tri-biotin | NA | NA | 37.3 | 66.6 | 51.1 | 74.1 | 73.1 | 65.4 | 62.0 |

TABLE 10

| $^{1}H$ NMR comparison of the biotin part of the trisaccharide biotin with a trisaccharide alkyne | | | | | | | | | | | | | | | | |
|---|---|---|---|---|---|---|---|---|---|---|---|---|---|---|---|---|
| | 3' | 4' | 5' | 6' | 7' | 8' | 9' | 10' | 11' | 12' | 13' | 14' | 15' | 16' | 17' | 18' |
| Biotene amine | 3.54 | 3.77~3.71 | | | | | 3.66 | 3.43 | 2.31 | 1.68 | 1.46 | 1.72 1.63 | 3.37 | 4.46 | 4.64 | 3.03, 2.82 |
| Tri-biotin | 4.64 down | 3.99 | 3.71~3.61 | | | | 3.64 | 3.40 | 2.28 | 1.66 | 1.42 | 1.59 1.42 | 3.33 | 4.42 | 4.60 | 3.00, 2.80 |

TABLE 11

| $^{13}C$ NMR comparison of the biotin part of the trisaccharide biotin with a trisaccharide alkyne | | | | | | | | | | | | | | | | |
|---|---|---|---|---|---|---|---|---|---|---|---|---|---|---|---|---|
| | 3' | 4' | 5' | 6' | 7' | 8' | 9' | 10' | 11' | 12' | 13' | 14' | 15' | 16' | 17' | 18' |
| Biotene amine | 49.9 | 69.4, 69.3, 69.3, 69.2, 69.0 | | | | | 68.6 | 38.6 | 35.2 | 24.8 | 27.6 | 27.4 | 55.1 | 61.8 | 60.0 | 39.4 |
| Tri-biotin | 49.4 up | 68.0 up | ~69.0 | | | | | 38.4 | 35.1 | 24.7 | 27.4 | 26.9 | 54.9 | 61.3 | 59.4 | 39.4 |

Example 9—References for Examples 1-8

1. Borcard, F.; Godinat, A; Staedler, D.; Comas Blanco, H.; Dumont, A.-L.; Chapuis-Bernasconi, C.; Scaletta, C.; Applegate, L. A.; Krauss Juillerat, F.; Gonzenbach, U. T.; Gether-Lemaire, S.; Juillerat-Jeanneret, L., Covalent Cell Surface Functionalization of Human Fetal Osteoblasts for Tissue Engineering. Bioconjugate Chemistry 2011, 22 (7), 1422-1432.
2. Ruhaak, L R; Xu, G.; Li, Q.; Goonatilleke, E.; Lebrilla, C. B., Mass Spectrometry Approaches to Glycomic and Glycoproteomic Analyses. Chemical Reviews 2018.
3. B., P. T.; B., S. W.; Joseph, G.; Keisuke, Y.; A., T. T.; Ritu, R.; Kim, W.; Shabaz, M.; V., R. C.; P., B. J. L.; G., D. B., Optimal Synthetic Glycosylation of a Therapeutic Antibody. Angewandte Chemie International Edition 2016, 55 (7), 2361-2367.
4. Zeng, Y.; Ramya, T. N. C.; Dirksen, A.; Dawson, P. E.; Paulson, J. C., High-efficiency labeling of sialylated glycoproteins on living cells. Nat Meth 2009, 6 (3), 207-209.

5. Saludes, J. P.; Ames, J. B.; Gervay-Hague, J., Synthesis and Structural Characterization of Sialic Acid-Glutamic Acid Hybrid Foldamers as Conforma□onal Surrogates of α-2,8-Linked Polysialic Acid. Journal of the American Chemical Society 2009, 131 (15), 5495-5505.
6. Lifely, M. R.; Gilbert, A. S.; Moreno, C., Sialic acid polysaccharide antigens of *Neisseria meningitidis* and *Escherichia coli*: Esterification between adjacent residues. Carbohydrate Research 1981, 94 (2), 193-203.
7. Flaherty, T. M.; Gervay, J., 2D NMR analysis of the polylactone derivative of colominic acid. Complete 1H and 13C NMR chemical shift assignments. Carbohydr. Res. 1996, 281 (1), 173-7.
8. Su, Y.; Kasper, C.; Kirschning, A.; Dräger, G.; Berski, S., Synthesis of New Polysialic Acid Derivatives. Macromolecular Bioscience 2010, 10 (9), 1028-1033.
9. Presolski, S. I.; Hong, V. P.; Finn, M. G., Copper-Catalyzed Azide-Alkyne Click Chemistry for Bioconjugation. Current protocols in chemical biology 2011, 3 (4), 153-162.
10. Holst, S.; Heijs, B.; de Haan, N; van Zeijl, R. J. M.; Briaire-de Bruijn, I. H.; van Pelt, G. W.; Mehta, A. S.; Angel, P. M.; Mesker, W. E.; Tollenaar, R. A.; Drake, R. R.; Bovée, J. V. M. G.; McDonnell, L. A.; Wuhrer, M., Linkage-Specific in Situ Sialic Acid Derivatization for N-Glycan Mass Spectrometry Imaging of Formalin-Fixed Paraffin-Embedded Tissues. Analytical Chemistry 2016, 88 (11), 5904-5913.
11. Pudelko, M.; Lindgren, A.; Tengel, T.; Reis, C. A.; Elofsson, M.; Kihlberg, J., Formation of lactones from sialylated MUC1 glycopeptides. Organic & Biomolecular Chemistry 2006, 4 (4), 713-720.
12. Gervay, J.; Ramamoorthy, P. S.; Mamuya, N. N., Ring opening of sialyllactones with glycine esters: Synthesis of selectively protected glycinyl-NeuAc saccharopeptides. Tetrahedron 1997, 53 (32), 11039-11048.
13. Gervay, J.; Peterson, J. M.; Oriyama, T.; Danishefsky, S. J., An unexpected sialylation: total syntheses of ganglioside GM4 and a positional isomer. The Journal of Organic Chemistry 1993, 58 (20), 5465-5468.
14. Danishefsky, S. J.; Koseki, K.; Griffith, D. A.; Gervay, J.; Peterson, J. M.; McDonald, F. E.; Oriyama, T., Azaglycosylation of complex stannyl alkoxides with glycal-derived iodo sulfonamides: a straightforward synthesis of sialyl-Lewis X antigen and other oligosaccharide domains Journal of the American Chemical Society 1992, 114 (21), 8331-8333.
15. Meng, X.; Yao, W.; Cheng, J.; Zhang, X.; Jin, L.; Yu, H.; Chen, X.; Wang, F.; Cao, H., Regioselective Chemoenzymatic Synthesis of Ganglioside Disialyl Tetrasaccharide Epitopes. Journal of the American Chemical Society 2014, 136 (14), 5205-5208.
16. Sakamoto, H.; Nakamura, S.; Tsuda, T.; Hashimoto, S., Chemoselective glycosidation strategy based on glycosyl donors and acceptors carrying phosphorus-containing leaving groups: a convergent synthesis of ganglioside GM3. Tetrahedron Letters 2000, 41 (40), 7691-7695.
17. Nicole, B.; Gregor, D.; Andreas, L.; Horst, K., Chemoenzymatic-Chemical Synthesis of a (2-3)-Sialyl T Threonine Building Block and Its Application to the Synthesis of the N-Terminal Sequence of Leukemia-Associated Leukosialin (CD 43). Angewandte Chemie International Edition 2001, 40 (12), 2292-2295.
18. Tan, Z.; Shang, S.; Halkina, T; Yuan, Y.; Danishefsky, S. J., Toward Homogeneous Erythropoietin: Non-NCL-Based Chemical Synthesis of the Gln78-Arg166 Glycopep□de Domain Journal of the American Chemical Society 2009, 131 (15), 5424-5431.
19. Wu, B.; Tan, Z.; Chen, G.; Chen, J.; Hua, Z.; Wan, Q.; Ranganathan, K.; Danishefsky, S. J., Mature homogeneous erythropoietin building blocks by chemical synthesis: the EPO 22-37 glycopeptide domain presenting the full N-linked dodecasaccharide. Tetrahedron Letters 2006, 47 (46), 8009-8011.
20. Hanamatsu, H.; Nishikaze, T.; Miura, N.; Piao, J.; Okada, K; Sekiya, S.; Iwamoto, S.; Sakamoto, N; Tanaka, K.; Furukawa, J.-i., Sialic Acid Linkage Specific Derivatization of Glycosphingolipid Glycans by Ring-Opening Aminolysis of Lactones. Analytical Chemistry 2018, 90 (22), 13193-13199.
21. Sekiya, S.; Wada, Y.; Tanaka, K., Derivatization for Stabilizing Sialic Acids in MALDI-MS. Analytical Chemistry 2005, 77 (15), 4962-4968.
22. Toyoda, M.; Ito, H.; Matsuno, Y.-k.; Narimatsu, H.; Kameyama, A., Quantitative Derivatization of Sialic Acids for the Detection of Sialoglycans by MALDI MS. Analytical Chemistry 2008, 80 (13), 5211-5218.
23. Endo, S.-i.; Morita, M.; Ueno, M.; Maeda, T.; Terabayashi, T., Fluorescent labeling of a carboxyl group of sialic acid for MALDI-MS analysis of sialyloligosaccharides and ganglioside. Biochemical and Biophysical Research Communications 2009, 378 (4), 890-894.
24. J., H. D.; Kavitha, B.; N., S. C., Application of negative ion MS/MS to the identification of N-glycans released from carcinoembryonic antigen cell adhesion molecule 1 (CEACAM1). Journal of Mass Spectrometry 2009, 44 (1), 50-60.
25. Harvey, D. J.; Royle, L.; Radcliffe, C. M.; Rudd, P. M.; Dwek, R. A., Structural and quantitative analysis of N-linked glycans by matrix-assisted laser desorption ionization and negative ion nanospray mass spectrometry. Analytical Biochemistry 2008, 376 (1), 44-60.
26. Wheeler, S. F.; Domann, P; Harvey, D. J., Derivatization of sialic acids for stabilization in matrix-assisted laser desorption/ionization mass spectrometry and concomitant differentiation of α(2→3)- and α(2→6)-isomers. Rapid Communications in Mass Spectrometry 2009, 23 (2), 303-312.
27. Alley, W. R.; Novotny, M. V., Glycomic Analysis of Sialic Acid Linkages in Glycans Derived from Blood Serum Glycoproteins. Journal of Proteome Research 2010, 9 (6), 3062-3072.
28. Reiding, K. R.; Blank, D; Kuijper, D. M.; Deelder, A. M.; Wuhrer, M., High-Throughput Profiling of Protein N-Glycosylation by MALDI-TOF-MS Employing Linkage-Specific Sialic Acid Esterification. Analytical Chemistry 2014, 86 (12), 5784-5793.
29. de Haan, N.; Reiding, K. R.; Haberger, M.; Reusch, D.; Falck, D.; Wuhrer, M., Linkage-Specific Sialic Acid Derivatization for MALDI-TOF-MS Profiling of IgG Glycopeptides. Analytical Chemistry 2015, 87 (16), 8284-8291.
30. Pongracz, T.; Wuhrer, M.; de Haan, N., Expanding the Reaction Space of Linkage-Specific Sialic Acid Derivatization. Molecules 2019, 24 (19).
31. Lageveen-Kammeijer, G. S. M.; de Haan, N; Mohaupt, P.; Wagt, S.; Filius, M.; Nouta, J.; Falck, D.; Wuhrer, M., Highly sensitive CE-ESI-MS analysis of N-glycans from complex biological samples. Nature Communications 2019, 10 (1), 2137.
32. Yang, S.; Jankowska, E.; Kosikova, M.; Xie, H.; Cipollo, J., Solid-Phase Chemical Modification for Sialic Acid Linkage Analysis: Application to Glycoproteins of Host Cells Used in Influenza Virus Propagation. Analytical Chemistry 2017, 89 (17), 9508-9517.

33. Yang, S.; Wu, W. W.; Shen, R.-F.; Bern, M.; Cipollo, J., Identification of Sialic Acid Linkages on Intact Glycopeptides via Differential Chemical Modification Using IntactGIG-HILIC. Journal of The American Society for Mass Spectrometry 2018, 29 (6), 1273-1283.
34. Li, H.; Gao, W.; Feng, X.; Liu, B.-F.; Liu, X., MALDI-MS analysis of sialylated N-glycan linkage isomers using solid-phase two step derivatization method. Analytica Chimica Acta 2016, 924, 77-85.
35. Nishikaze, T.; Tsumoto, H.; Sekiya, S.; Iwamoto, S.; Miura, Y.; Tanaka, K, Differentiation of Sialyl Linkage Isomers by One-Pot Sialic Acid Derivatization for Mass Spectrometry-Based Glycan Profiling. Analytical Chemistry 2017, 89 (4), 2353-2360.
36. Jiang, K.; Zhu, H.; Li, L.; Guo, Y.; Gashash, E.; Ma, C.; Sun, X.; Li, J.; Zhang, L.; Wang, P. G., Sialic acid linkage-specific permethylation for improved profiling of protein glycosylation by MALDI-TOF MS. Analytica Chimica Acta 2017, 981, 53-61.
37. Nishikaze, T., Sialic acid derivatization for glycan analysis by mass spectrometry. Proceedings of the Japan Academy, Series B 2019, 95 (9), 523-537.
38. Sletten, E. M.; Bertozzi, C. R., Bioorthogonal Chemistry: Fishing for Selectivity in a Sea of Functionality. Angewandte Chemie International Edition 2009, 48 (38), 6974-6998.
39. Bertozzi, C. R., A Decade of Bioorthogonal Chemistry. Accounts of Chemical Research 2011, 44 (9), 651-653.
40. Devaraj, N. K., The Future of Bioorthogonal Chemistry. ACS Central Science 2018, 4 (8), 952-959.
41. Kayser, H.; Zeitler, R.; Kannicht, C.; Grunow, D.; Nuck, R.; Reutter, W., Biosynthesis of a nonphysiological sialic acid in different rat organs, using N-propanoyl-D-hexosamines as precursors. Journal of Biological Chemistry 1992, 267 (24), 16934-8.
42. Mahal, L K; Yarema, K. J.; Bertozzi, C. R., Engineering Chemical Reactivity on Cell Surfaces Through Oligosaccharide Biosynthesis. Science (New York, N.Y.) 1997, 276 (5315), 1125.
43. Charter, N. W.; Mahal, L K.; Koshland Jr, D. E.; Bertozzi, C. R., Biosynthetic incorporation of unnatural sialic acids into polysialic acid on neural cells. Glycobiology 2000, 10 (10), 1049-1056.
44. Jacobs, C. L.; Goon, S.; Yarema, K. J.; Hinderlich, S.; Hang, H. C.; Chai, D. H.; Bertozzi, C. R., Substrate Specificity of the Sialic Acid Biosynthetic Pathway. Biochemistry 2001, 40 (43), 12864-12874.
45. Mahal, L. K.; Charter, N. W.; Angata, K.; Fukuda, M.; Koshland, D E, Jr.; Bertozzi, C. R., A small-molecule modulator of poly-alpha 2,8-sialic acid expression on cultured neurons and tumor cells. Science (New York, N.Y.) 2001, 294 (5541), 380-1.
46. Saxon, E.; Bertozzi, C. R., Cell Surface Engineering by a Modified Staudinger Reaction. Science (New York, N.Y.) 2000, 287 (5460), 2007.
47. Saxon, E.; Luchansky, S. J.; Hang, H. C.; Yu, C.; Lee, S. C.; Bertozzi, C. R., Investigating Cellular Metabolism of Synthetic Azidosugars with the Staudinger Ligation. Journal of the American Chemical Society 2002, 124 (50), 14893-14902.
48. Hsu, T.-L.; Hanson, S. R.; Kishikawa, K.; Wang, S.-K.; Sawa, M.; Wong, C.-H., Alkynyl sugar analogs for the labeling and visualization of glycoconjugates in cells. Proceedings of the National Academy of Sciences 2007, 104 (8), 2614.
49. Luchansky, S. J.; Goon, S.; Bertozzi, C. R., Expanding the Diversity of Unnatural Cell-Surface Sialic Acids. ChemBioChem 2004, 5 (3), 371-374.
50. Han, S.; Collins, B. E.; Bengtson, P.; Paulson, J. C., Homomultimeric complexes of CD22 in B cells revealed by protein-glycan cross-linking Nature Chemical Biology 2005, 1 (2), 93-97.
51. Yarema, K. J.; Sun, Z., A photochemical snapshot of CD22 binding. Nature Chemical Biology 2005, 1 (2), 69-70.
52. Tanaka, Y.; Kohler, J. J., Photoactivatable Crosslinking Sugars for Capturing Glycoprotein Interactions. Journal of the American Chemical Society 2008, 130 (11), 3278-3279.
53. Bond, M. R.; Zhang, H.; Vu, P. D.; Kohler, J. J., Photocrosslinking of glycoconjugates using metabolically incorporated diazirine-containing sugars. Nature Protocols 2009, 4 (7), 1044-1063.
54. Kim, E. J.; Sampathkumar, S.-G.; Jones, M. B.; Rhee, J. K.; Baskaran, G.; Goon, S.; Yarema, K. J., Characterization of the Metabolic Flux and Apoptotic Effects of O-Hydroxyl- and N-Acyl-modified N-Acetylmannosamine Analogs in Jurkat Cells. Journal of Biological Chemistry 2004, 279 (18), 18342-18352.
55. Viswanathan, K.; Lawrence, S.; Hinderlich, S.; Yarema, K. J.; Lee, Y. C.; Betenbaugh, M. J., Engineering Sialic Acid Synthetic Ability into Insect Cells: Identifying Metabolic Bottlenecks and Devising Strategies To Overcome Them. Biochemistry 2003, 42 (51), 15215-15225.
56. Xie, R.; Hong, S.; Feng, L.; Rong, J.; Chen, X., Cell-Selective Metabolic Glycan Labeling Based on Ligand-Targeted Liposomes. Journal of the American Chemical Society 2012, 134 (24), 9914-9917.
57. Feng, L.; Hong, S.; Rong, J.; You, Q.; Dai, P.; Huang, R.; Tan, Y.; Hong, W.; Xie, C.; Zhao, J.; Chen, X., Bifunctional Unnatural Sialic Acids for Dual Metabolic Labeling of Cell-Surface Sialylated Glycans. Journal of the American Chemical Society 2013, 135 (25), 9244-9247.
58. Palaniappan, K. K.; Bertozzi, C. R., Chemical Glycoproteomics. Chemical Reviews 2016, 116 (23), 14277-14306.
59. Laughlin, S. T.; Bertozzi, C. R., Imaging the glycome. Proceedings of the National Academy of Sciences 2009, 106 (1), 12-17.
60. Du, J.; Meledeo, M. A.; Wang, Z.; Khanna, H. S.; Paruchuri, V. D. P.; Yarema, K. J., Metabolic glycoengineering: Sialic acid and beyond. Glycobiology 2009, 19 (12), 1382-1401.
61. Wmtil, P. R.; Horstkorte, R.; Reutter, W., Metabolic Glycoengineering with N-Acyl Side Chain Modified Mannosamines. Angewandte Chemie International Edition 2016, 55 (33), 9482-9512.
62. Wen, L.; Zheng, Y.; Jiang, K.; Zhang, M.; Kondengaden, S. M.; Li, S.; Huang, K.; Li, J.; Song, J.; Wang, P. G., Two-Step Chemoenzymatic Detection of N-Acetylneuraminic Acid-α(2-3)-Galactose Glycans. Journal of the American Chemical Society 2016, 138 (36), 11473-11476.
63. Wen, L.; Liu, D.; Zheng, Y.; Huang, K.; Cao, X.; Song, J.; Wang, P. G., A One-Step Chemoenzymatic Labeling Strategy for Probing Sialylated Thomsen-Friedenreich Antigen. ACS Central Science 2018, 4 (4), 451-457.
64. Wollscheid, B.; Bausch-Fluck, D.; Henderson, C.; O'Brien, R.; Bibel, M.; Schiess, R.; Aebersold, R.; Watts, J. D., Mass-spectrometric identification and relative quantification of N-linked cell surface glycoproteins. Nature Biotechnology 2009, 27, 378.

65. Zeng, Y.; Ramya, T. N. C.; Dirksen, A.; Dawson, P. E.; Paulson, J. C., High-efficiency labeling of sialylated glycoproteins on living cells. Nature Methods 2009, 6, 207.

Example 10—AA_XL Protocol on Model Proteins and Formalin-Fixed, Paraffin-Embedded (FFPE) Slides

Material

Deuterium oxide (D2O, 99.9%), Dimethyl sulfoxide-d6 (DMSO-d6, 99.9%), DMSO, (anhydrous), sodium cyanoborohydride (NaCNBH3, 95%), 2-amino benzoamide (2AB, anthranilamide, 98%), colominic acid sodium salt (from *Escherichia coli*, CAS #70431-34-4), α-Cyano-4-hydroxycinnamic acid (CHCA, for MALDI-IMS), N-(3-Dimethylaminopropyl)-N'-ethylcarbodiimide (EDC, ≥97%), 1-Hydroxybenzotriazole hydrate (HOBt, with ≥20 wt. % water), dimethylamine (40 wt. % in water), propargylamine (98%), copper (II) sulfate (CuSO4, 99%), aminoguanidine hydrochloride (98%), sodium ascorbate (99%), tris(3-hydroxypropyltriazolylmethyl)amine (THPTA, 95%), Mayer's hematoxylin solution, trifluoroacetic acid (TFA), sodium dodecyl sulfate (SDS, 99%), Trisma base (99%) and Hydrochloric acid (37% in water) were obtained from Sigma-Aldrich (St. Louis, MO). SilverQuest silver staining kit (Invitrogen), SeeBlue and BenchMark protein ladder (Invitrogen), Bolt 4-12% Bis-Tris Plus gel, matching MOPS SDS running buffer and transfer buffer (Invitrogen), Bolt LDS loading buffer (non-reductive, Invitrogen), Sep-Pak C18 cartridge, Hypercarb Hypersep cartridge, Cytoseal, xylene (histological grade), cover glass (Slip-Rite, 23×50, #1), chloroform (HPLC grade), acetic acid (AcOH), water (HPLC grade), acetonitrile (MeCN, HPLC grade) and ammonia in water (28~30 wt. %) were obtained from Thermo Fisher Scientific (Waltham, MA). Ethanol (200 proof) were obtained from Decon Lab (King of Prussia, PA). 11-Azido-3,6,9-trioxaundecan-1-mine (azido-PEG3-amine, NH2-PEG3-N3, 95%) and D-biotin (98%) were obtained from AK Scientific (Union City, CA). Biotin alkyne (CAS# 773888-45-2, 98%) was obtained from Synthonix (Wake Forest, NC). 3'sialyllactose, 6'sialyllactose, 3'sialyllactose-BSA and 6'sialyllactose-BSA were obtained from Carbosynth (San Diego, CA). Horseradish peroxidase-3,3'-diaminobenzidine (HRP-DAB) staining kits were obtained from R&D Systems. Recombinant PNGase F PRIME™ was obtained from N-Zyme Scientific (Doylestown, PA). Biotinylated Aleuria Aurantia Lectin (b-AAL) was obtained from Vector Laboratorie (Burlingame, CA). Streptavidin-IR800, protein blocking reagent and nitrocellulose membrane (pore size 0.2 μm) were obtained for LI-COR (Lincoln, Nebraska). Incubation chamber (200 μL, Cat. #70324-20) was obtained from Electron Microscopy Sciences (Hatfield, PA). Sialidase (SialEXO) was obtained from Genovis (Cambridge, MA). Gel (10×8, 10%, 10 wells), matching Tris-MOPS running buffer and transfer buffer were obtained from GenScript (Piscataway, NJ).

Development of AA_XL Protocol Using Oligosaccharide Model Compounds

Scheme 12
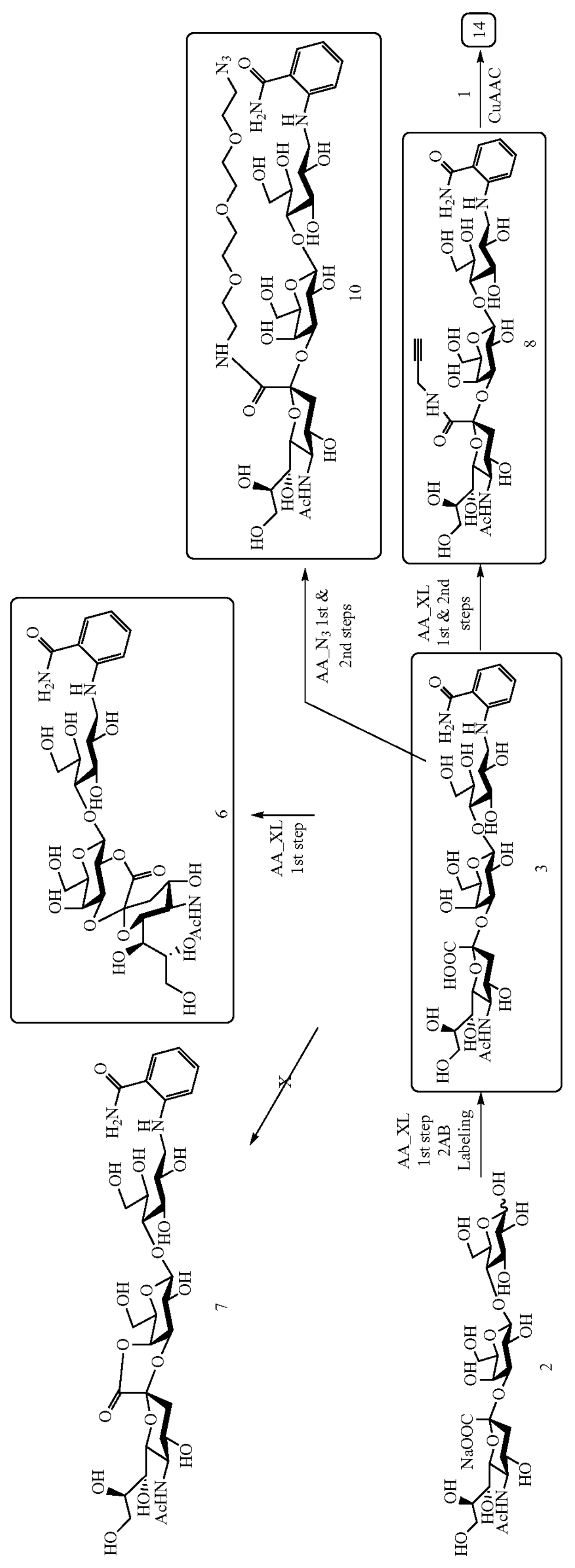
2
3
6
7
8
10
14

-continued
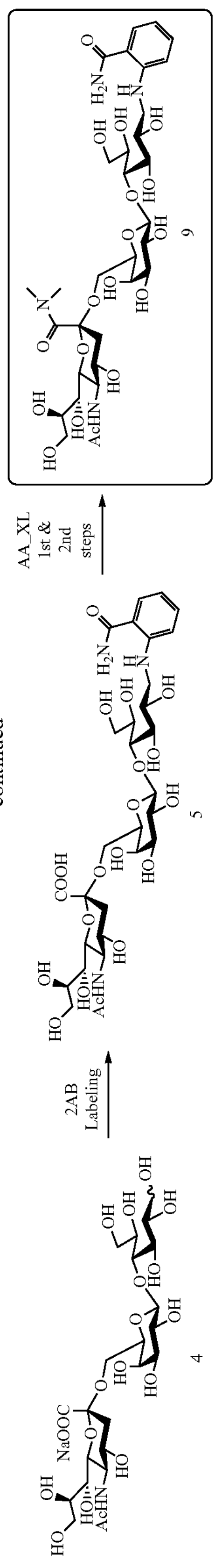
4
5
9
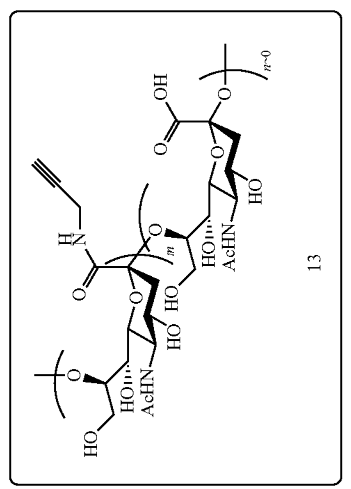
11
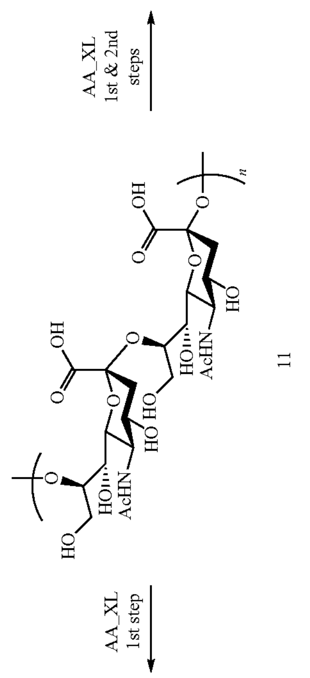
13
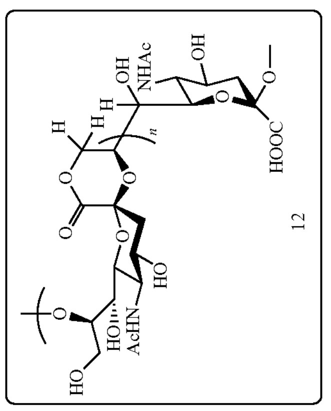
12
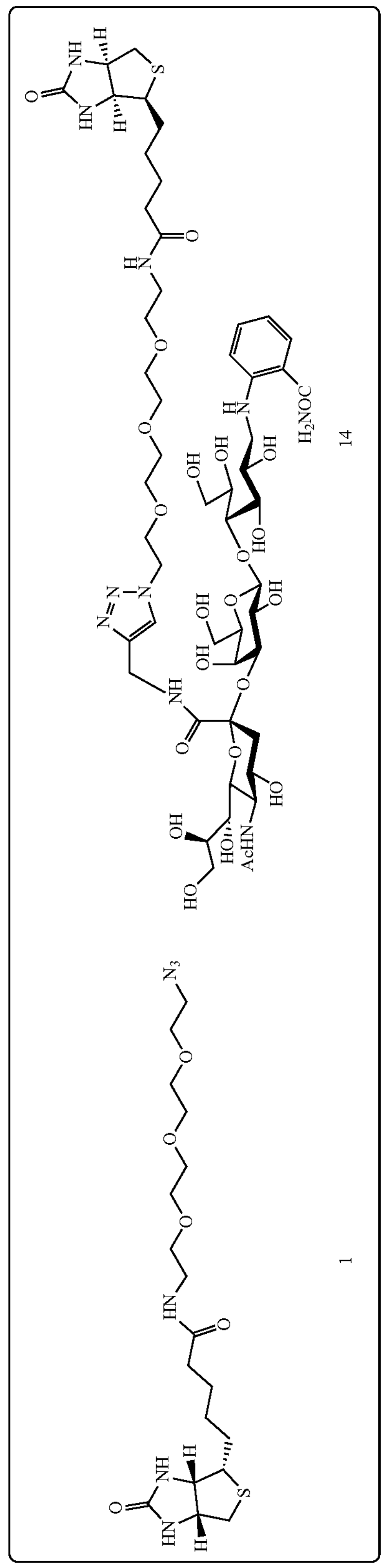
1
14

2.1 General Protocol

Reaction was carried out in conical reaction vial with sealed cap. NMR spectra were measured at 25° C., at 600 MHz for 1H and at 150 MHz for 13C. Assignments of NMR signals were aided by 1D and 2D experiments (DEPT, COSY, HSQC, HMQC, and HMBC) run with the software supplied with the spectrometers. With $D_2O$ as solvent, 1H and 13C chemical shifts were referenced to signals of H2O (4.80 ppm) and methanol (external, 49.50 ppm). With DMSO-d6 as solvent, 1H and 13C chemical shifts were referenced to signals of DMSO (2.50 ppm) and DMSO (39.51 ppm). Workup: reaction mixture was placed in speed vac upto 1 day at r.t. until most volatile reagent and solvent were removed. Acetonitrile (10 times the left volume) was added and the product was precipitate out. Precipitates was collected and washed with acetonitrile for 3 times. 1H NMR of crude mixture before purification indicate conversion yield. Cartridge purification: each 10 mg reaction mixture was dissolved in 0.3 mL water and loaded onto Sep-Pak C18 cartridge (3 cc, 500 mg). Cartridge was eluted with water (3 mL), 5% MeCN in water (3 mL), and 10% MeCN in water (4 mL). Eluent was collected in Eppendorf tube (about 0.5 mL each), and spotted on cellulose chromatography paper. 2AB labeling compounds were detected under UV light (254 nm).

2AB Labeling of Trisaccharide Model Compounds

To a mixed solvent of AcOH (0.9 mL) and DMSO (2.1 mL), add $NaCNBH_3$ (144 mg, 2.29 mmol) and 2-AB (2-amino benzoamide, 120 mg, 0.88 mmol). 2-amino benzoamide (60 mg, 0.092 mmoL) was added to the flask and the reaction was heated at 60° C. for 4.5 hrs. Reaction mixture was cooled down to room temperature and a mixture solvent of TEA (0.1 mL) and MeCN (40 mL) were added. Product precipitated out during shaking and supernatant was removed. Cartridge purification yield trisaccharide 3, Scheme 12 (46 mg, 67%). Trisaccharide 5, Scheme 12 was synthesized from trisaccharide 4, Scheme 12 in 80% in the same way as described for the synthesis of trisaccharide 3, Scheme 12.

AA_XL on Model Compounds

For the first step, EDC (44 μL, 38.8 mg, 0.25 mmol, 0.25M), HOBt (1-Hydroxybenzotriazole hydrate, about 20% wt water, 86 mg, 0.5 mmol, 0.5M), and dimethylamine (40% wt in water, 31.4 uL, 11.2 mg, 0.25 mmol, 0.25M) were added into DMSO (1 mL, anhydrous) to make the $1^{st}$ step reaction mixture. Add model compound into reaction mixture (~200 uL per each 1 mg model compounds). Incubate at 60° C. for 1 h. For AA_XL $2^{nd}$ step, add propargyl amine (0.4 mL per 1 mL DMSO in $1^{st}$ step reaction mixture). Incubate at 60° C. for 2~5 hrs depending on the scale of the reaction. Workup and purification was described in general protocol. With this protocol, amide 8, Scheme 12 and 9, Scheme 12 was synthesized from trisaccharide 3 and 5, Scheme 12 with quantitative conversion yield and 80% isolation yield. Amide 13, Scheme 12 was synthesized form polysaccharide 11, Scheme 12 with 75% conversion yield and 35% isolation yield. To test the stability of 9, Scheme 12, isolated pure amide 9, Scheme 12 was added into propargyl amine-DMSO (2/5, v/v) and heated at 60° C. for 5 h, the amide 9, Scheme 12 didn't change.

Lactone Formation with AA_XL First Step

AA_XL the first step and general workup was applied to trisaccharide 5, Scheme 12 (2.5 mg, 3.32 μmol). The crude mixture was dissolved in DMSO-d6 for NMR acquisition. As from H-NMR, the conversion from 5, Scheme 12 to lactone 6, Scheme 12 is quantitative. Lactone 6, Scheme 12 decomposed in aqueous solvent. Therefore, no purification was performed. Lactone 12, Scheme 12 was synthesized the same way as lactone 6, Scheme 12. 1D and 2D NMR'[1-5] indicate quantitative conversion.

AA_N3 replace propargal amine in AA_XL with same volume of $NH_2$-PEG3-$N_3$ is the AA_N3 protocol. With AA_N3 protocol, amide 10, Scheme 12 is synthesized form trisaccharide 3, Scheme 12 with quantitative conversion yield and 80% isolation yield.

CuAAC on Trisaccharide Alkyne

CuAAC mixture for carbohydrate alkyne with sodium ascorbate and THPTA (Tris(benzyltriazolylmethyl)amine)[6] was prepared as in Table 12. To above mixture (6.5 mL), alkyne 8, Scheme 12 (2 mg, 2.5 μmol) was added. The reaction flask was filled with nitrogen and left in dark at r.t. overnight. For purification purpose, 1 μL propargyl amine was added into the reaction mixture to convert leftover biotin-PEG3-azide to Biotin-PEG3-amine. The second click reaction was left at r.t. for 6 hrs. Water was removed by lyophilization. 1H NMR on crude mixture indicate quantitative conversion. Several rounds of cartridge purification with Hypercarb Hypersep cartridge (25 mg, 1 mL, thermos scientific product #60106-304) yield pure product 14, Scheme 12 (0.5 mg, 16%)

TABLE 12

CuAAC mixture for carbohydrate alkyne prepared by AA_XL

| | | MW | Reagent [C] | ReagemtsStock Sln [C] | Reagent stock Sln prep. Per 1 mL water | Volumn of stock sln added |
|---|---|---|---|---|---|---|
| A | Biotin-$PEG_3$-azide 1 | 356.16 | 1.0 mM | 50 mM | 17.8 mg | 10 μL |
| B | CuSO4 | 159.61 | 0.1 mM | 20 mM | 3.19 mg | 2.5 μL |
| C | Sodium ascorbate | 198.11 | 5 mM | 100 mM | 20 mg | 25 μL |
| D | THPTA | 434.5 | 0.5 mM | 50 mM | 21.725 mg | 5 μL |
| E | Aminioguanidine HCl | 110.55 | 5 mM | 100 mM | 11 mg | 25 μL |
| F | 10xPBS | | | | | 432.5 μL |
| | Overall volume | | | | | 500 μL |

Mix B and D in an Eppendorf tube. Add A and F into another Eppendorf tube. Sequentially add B&D mixture, E and C into the A&F mixture. Reagent A, B, D, E and F could be prepared as a stock solution. Sodium ascorbate solution (C) needs to be prepared fresh.

AA_XL and CuAAc on Model Proteins
Scheme 13
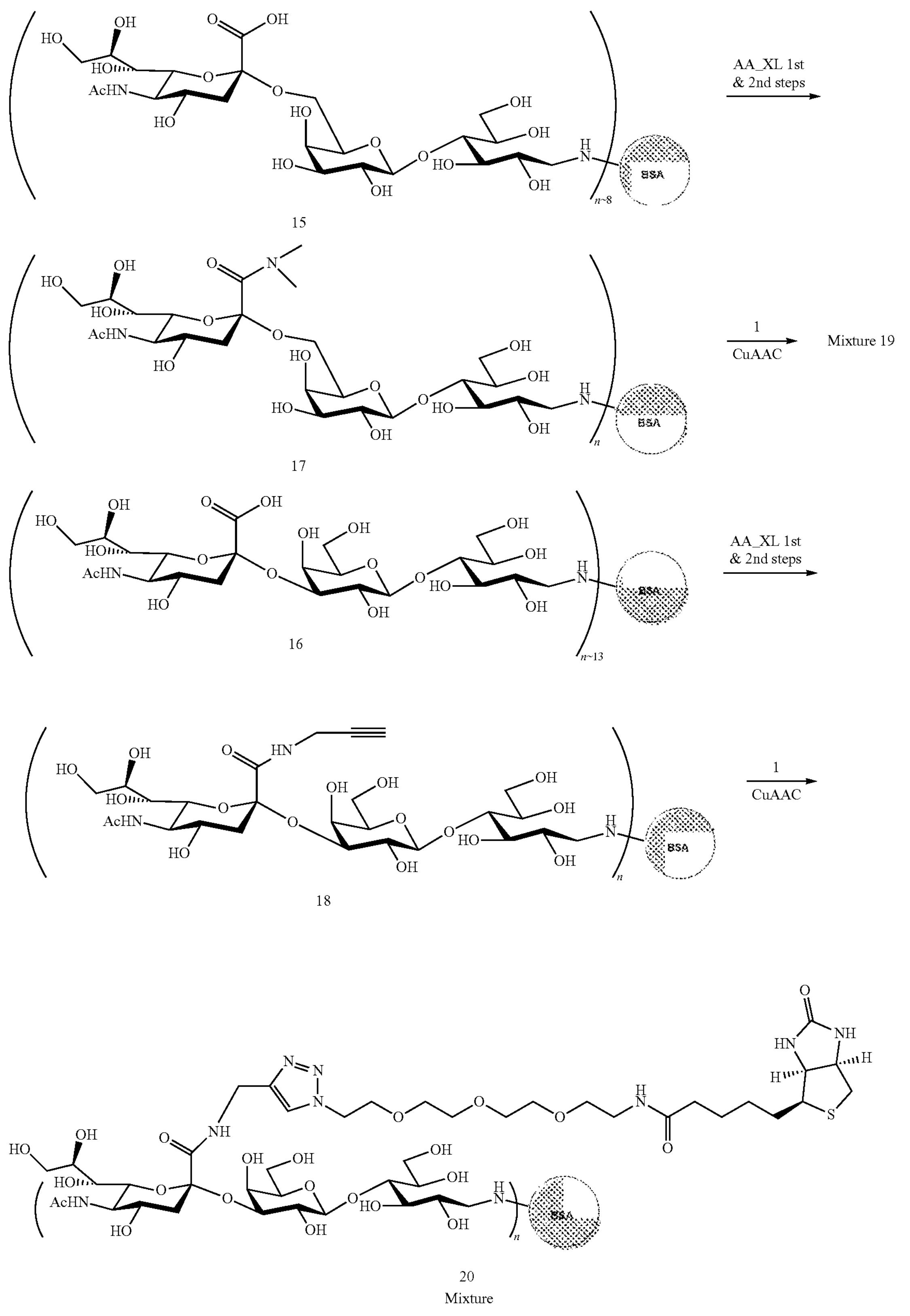
15
17
16
18
20
Mixture

Apply AA_XL and CuAAc Reactions on 6'sialyllactose-BSA 15 and 3'sialyllactose-BSA 16

50 μL AA_XL $1^{st}$ step reaction mixture was added into 6'sialyllactose-BSA 15, Scheme 13 (30 μg). Reaction flask was sealed and heated for 1 hr at 60° C. For the $2^{nd}$ step, proparglyamine (20 uL) was added. Reaction flask was sealed and heated for 2 hr at 60° C. After cooling down to r.t., 10×PBS (1.4 mL) was added. The resulting solution was passed through (Amicon Ultra 3K Cat #UFC800308), and wash with 10×PBS buffer. The amount of the resulting protein 17 (11.25 μg, 37.5% wt. recovery) was characterized by both BCA protein assay and CBB stain on SDS-page. Protein 18, Scheme 13 was prepared from 3'sialyllactose-BSA 16, Scheme 13 with the same protocol. CuAAC mixture as in Table 12 (10 μL) was added into lypheopized protein 18, Scheme 13 (1 μg, from 0.1 μg/μL 10×PBS sln, contain maximum $1.72\times10^{-4}$ μmol alkyne). Reaction flask was sealed with parafilm. Reaction was left at r.t. overnight in dark to yield mixture 20, Scheme 13. Mixture 19, Scheme 13 was prepared the same way from protein 17, Scheme 13.

SDS Page and Western Blotting:

Click reaction mixture 19, Scheme 13 (0.8 μg) and 20, Scheme 13 (0.8 μg) was mixed with loading buffer (Laemmli SDS sample buffer, reducing, Alfa Aesar), heated and loaded on gel (GenScript, 10×8, 10%, 10 wells of 80 Gel was developed with Tris-MOPS running buffer (GenScipt, cat #M00138) at r.t. about 100 V and transferred to nitrocellulose membrane (LI-COR, pore size 0.2 μm) in transfer buffer (GenScipt, cat #M00139) at 310 mA for 1.5 hr in an ice-water bath. Membrane was placed in 50 mL Eppendorf tube (front face up). PBS blocking buffer (5 mL, LI-COR) was add, and Eppendorf tube was rotate at r.t. for 1 h. The membrane was wash with PBST 0.1% (3 min×5) and PBS (3 min×1). Streptavidin-IR800 (5 mL, 1×5000 in PBS) was added and tube was rotated at r.t. wrapped with aluminum foil for 1 h. Membrane was washed with PBST 0.1% (3 min×5) in a black container and then with PBS (1 min×3). Membrane was scan with LI-COR at 800 nm.

AA_XL on Formalin-Fixed, Paraffin-Embedded (FFPE) Slides

General Protocol of On-Slide Tissue Preparation for MALDI IMS

Figure 3:
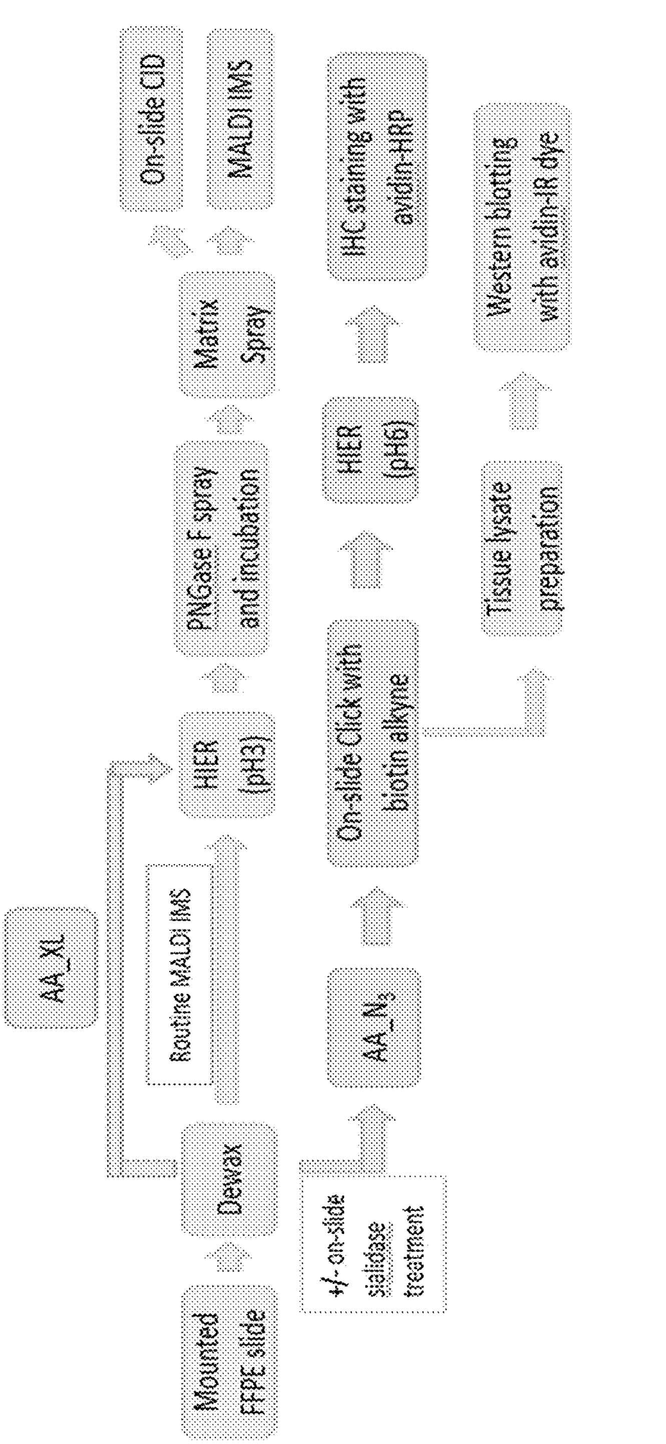
FIG. 3 shows a workflow for AA_XL or AA_$N_3$ treated FFPE slides.

FIG. 3 shows a workflow for AA_XL or $AA\_N_3$ treated FFPE slides. General protocols were reported in 2014[7] and elaborated on in 2018[8-9]. Briefly, FFPE tissue was sectioned at 5 μm, dehydrated overnight at 37° C. and stored in a cool, dry environment. As for dewax, slides were heated at 60° C. for 1 hr, cooled for 5 min at r.t. and put through the following incubations (fresh aliquots): Xylene (3 min×2), 200 proof ethanol (1 min×2), 95% ethanol (1 min×1), 70% ethanol (1 min×1) and distilled water (3 min×3). As for heat-induced epitope retrieval (HIER), slides was placed into a mailer filled with 10 mM citraconic anhydride buffer (pH 3), and the mailer was placed into a vegetable steamer for 30 min. Buffer exchange was performed (replace half the buffer with distill water and incubate at r.t. for 5 min, repeat two more times). After buffer exchanged, slides was washed with distill water and placed in vacuum dedicator till dry. As for PNGase F spray and incubation, the enzyme was applied to slides using M3 TMSprayer (Tissue MALDI Sample Preparation System, HTX technologies, LLC) at 0.1 μg/μL in water using parameters of 45° C., 10 psi, 25 μL/min, 1200 velocity(mm/min), and 15 passes with a 2.5 mm offset. The slides were then placed in a humidity chamber and incubated at 37° C. for 2 hrs and then dried in vacuum desiccator. As for matrix spray, CHCA (α-cyano-4-hydroxycinnamic acid, 7 mg/mL in 50% acetonitrile/49.9% water/0.1% trifluoroacetic acid) was sprayed onto slide using the same M3 TM-Sprayer using parameters of 77° C., 10 psi, 100 μL/min, 1300 velocity (mm/min), and 10 passes with a 3.0 mm offset. As for MALDI IMS data acquisition and process, tissue slides were analyzed by MALDI-FT-ICR (solariX Legacy 7.0 T, Bruker) and timsTOF flex (Bruker) in positive mode. Data were visualized in flexImaging 4.0 (Bruker) and analyzed by SCiLS Lab software 2017a (Bruker). All images were normalized to total ion current. TimsTOF flex was used to acquire on tissue MS/MS data by collision-induced dissociation (CID) following previous reported method[10]. A 10 Da window was used for precursor selection. The collision energies was individually optimized and ranged from 80 to 140 eV. Spectra from single laser shot was used for most analysis.

AA_XL on FFPE Slides for MALDI IMS

Dewaxed slides were dried in vacuum desiccator for at least 30 min. AA_XL first step reaction mixture was freshly prepared (Table 13) and applied onto the tissue on the slide (200 to about 400 μL each slide). Cover glass was placed on top of the tissue. Slides were placed into a Pyrex lunch box with a lock lid. The lunch box was incubated in 60° C. oven for 1 hr. After the incubation, slide was taken out and let cool down inside hood for 5 min. This cooling down step prevent tissue from pilling off from the slide while removing the cover glass. Cover glass was removed by letting drop by weight. A stream of DMSO (anhydrous) could be placed on the top edge of the cover glass to help it drop. No other solvent should be applied on tissue. Pulling cover glass by hand might lead to tissue pilling off. The bigger the volume of first step reaction mixture applied, the easier the cover glass will be removed. Slide was placed perpendicular on paper tower to remove most of the reaction mixture (FIG. 4A). Vacuum dry setup (FIG. 4B) was used to remove the rest of the reaction mixture. Vacuum dry step was limited to 10 seconds, because over dry will make reagent stuck on tissue. DMSO (anhydrous, 400 μL) was applied to the tissue, and was removed the same way as reaction mixture. This DMSO washing step was repeated for two more times. Second step reaction mixture (200 to about 400 μL, Table 13) was applied onto the tissue. Cover glass was placed on top of the tissue. Tissue slide was placed inside a lunch box sealed and incubated in the 60° C. oven for 2 hrs. After incubation, slides was taken out, cooled down and the cover glass was removed with the aid of a stream of EtOH placed on the top edge of the cover glass. Slides were placed in mailer and washed by gentle shaking with the flowing solvents: 100% EtOH (2 min×2), Carnoys solution (30% chloroform, 60% ethanol, 10% acetic acid) (10 min×2), 100% EtOH (2 min×2), 0.1% TFA in pure ethanol (10 ml, poured over 30 second), water (3 min×2). Slides can optionally be stored in vacuum desiccator or proceeded for MALDI IMS as described in the section immediately preceding regarding discussing the general protocol starting with HIER See also Scheme 14.

Scheme 14

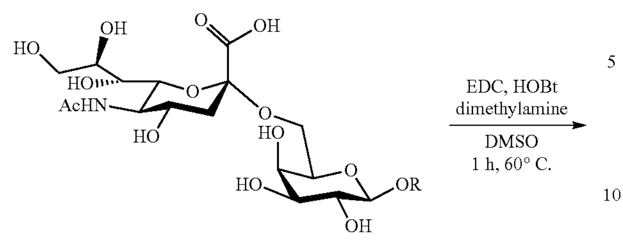

2,6 sialic acid

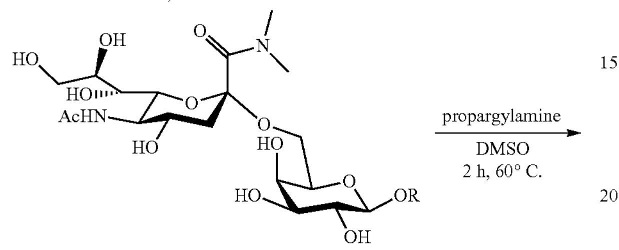

+27.0473 Da

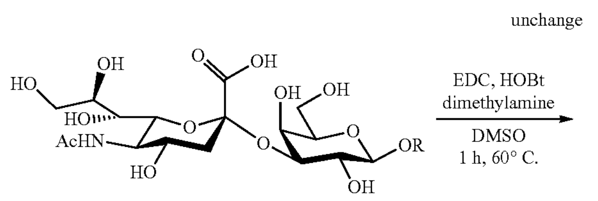

2,3 sialic acid

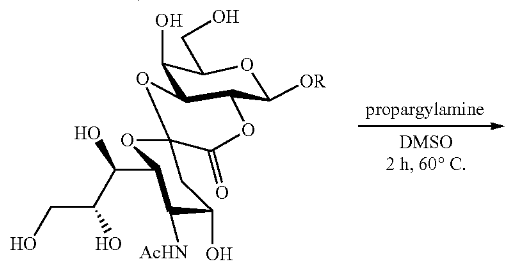

-18.0106 Da

-continued

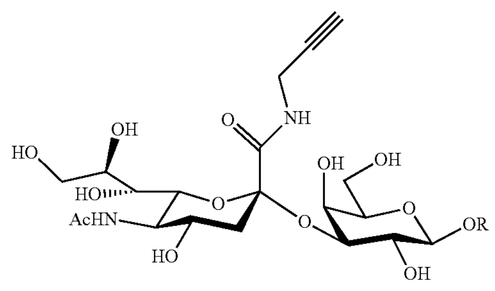

+37.0316 Da

TABLE 13

| AA_XL reaction reagent mixture | | | |
|---|---|---|---|
| | Concentration (M) | Mole (mmol) | Weight or Volume |
| Reaction solution for the 1st step (0.5 mL, for 1 slide) | | | |
| EDC | 0.25 | 0.125 | 22 μL |
| HOBt | 0.5 | 0.25 | 42.2 mg |
| dimethylamine | 0.25 | 0.125 | 15.8 μL |
| DMSO | | | 0.5 mL |
| Reaction solution for the 2nd step (0.7 mL, for 1 slide) | | | |
| Propargylamine | | | 200 μL |
| DMSO | | | 500 μL |

AA Protocol and AA_N3 Protocol

Compare to AA_XL protocol, the only difference for AA or AA_N3 are the second step reaction mixture (Table 14). For AA, propargylamine in AA_XL was replaced by the same volume of ammonia in water. For AA_N3, propargylamine in AA_XL was replaced by same volume of $NH_2$-$PEG_3$-$N_3$.

TABLE 14

| Reaction mixture, product and mass shifts for AA_XL. AA and AA_ N3 comparison | | | | |
|---|---|---|---|---|
| | | AA_XL | AA | $AA\_N_3$ |
| Reaction mixture | 1st step | the same | | |
| | 2nd step | propargylamine/ DMSO v/v 2:5 | ammonia in water (28%)/DMSO v/v 2:5 | $NH_2$—$PEG_3$—$N_3$/DMSO v/v 2:5 |
| Product | 2,6 sialic acid | the same, as in Scheme 14. | | |
| | 2,3 & 2,8 sialic acid | in Scheme 14 | 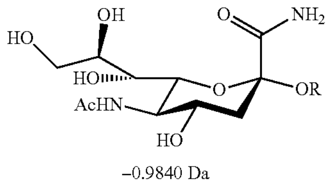 –0.9840 Da | 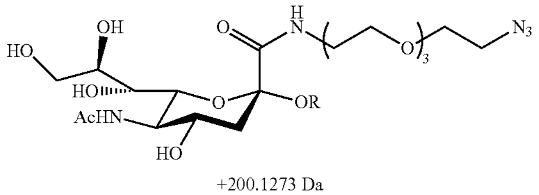 +200.1273 Da |

Four Slides: AA_XL, AA, Only the Washes, Dewax Comparison

Four prostate tissue (10191A) FFPE slides were dewaxed, the first slide, went through AA_XL protocol; the second slide went through AA protocol, the third slide subjected to only the washes (only washes) after the second step of AA_XL reaction. The fourth slide stay as only dewaxed (dewaxed). All four slides were then subject to HIER (10 mM citrate buffer, pH 6.0) using Decloaker program 5 (95° C., 15 min), and processed for MALDI IMS as described in the general protocol section of this Example above starting with PNGase F spray and incubation.

Sialidase Treated FFPE Slides

FFPE tissue was dewaxed and subject to HIER (pH 3). A humidity chamber was prepared with a Pyrex lunch box with a lock lid and a tip rack (FIG. 55). Water was added into the humidity chamber, and an incubation chamber (200 μL, Electron Microscopy Sciences, Cat. # 70324-20) was placed on the tip rack. 200U of a sialidase mix (for removal of α2-3, α2-6 and α2-8 sialic acids, SialEXO, Genovis) in 200 μL incubation buffer (20 mM Tris buffer, pH 6.8) was added into the incubation chamber. FFPE tissue slides was placed on top of the chamber face down. The humidity chamber with the tissue slides was incubated at 37° C. overnight. Carbon dioxide bubbles accumulated inside the incubation chamber, which indicate the success of the sialic acid cleavage reaction. Enzyme solution was discarded and the slide was washed with DI water (3 min×3). Tissue was subject to sialidase (100 U in 200 μL incubation buffer) and incubated at 37° C. for 8 more hrs. Small amount of carbon dioxide bubbles was observed, which indicate more sialic acid cleavage. After washing (DI water, 3 min×3), tissue was subject to sialidase (100 U in 200 μL incubation buffer) and incubated at 37° C. for overnight. No more bubbles was observed, tissue slide was washed with DI water (3 min×3).

CuAAC on AA_$N_3$ Slides

FFPE tissue slide was dewaxed, subjected to AA_N3 reaction and washes (Scheme 15). If the slides were dry, rehydrate the slide with 200 μL DI water (incubate for 1 min and discard). Reaction setup was as described in previous section regarding the sialidase treated FFPE slides in this Example. Slide was placed face down onto incubation chamber with freshly prepared click reaction mixture (200 Table 15). Lunch box was filled with argon, sealed and wrapped with aluminum foil. Reaction was left at room temperature overnight. The next morning, slides were placed in mailer and washed by gentle shaking with the flowing solvents: water (3 min x 3), EtOH (2 min×1), Carnoys sln. (10 min×2), EtOH (2 min×1), water (3 min×3). As for catalyst free negative control, reaction mixture was prepared by replacing $CuSo_4$ (B) and THPTA (D) with same volume of 10×PBS (F). The reaction setup, reaction time and washes are the same.

Scheme 15

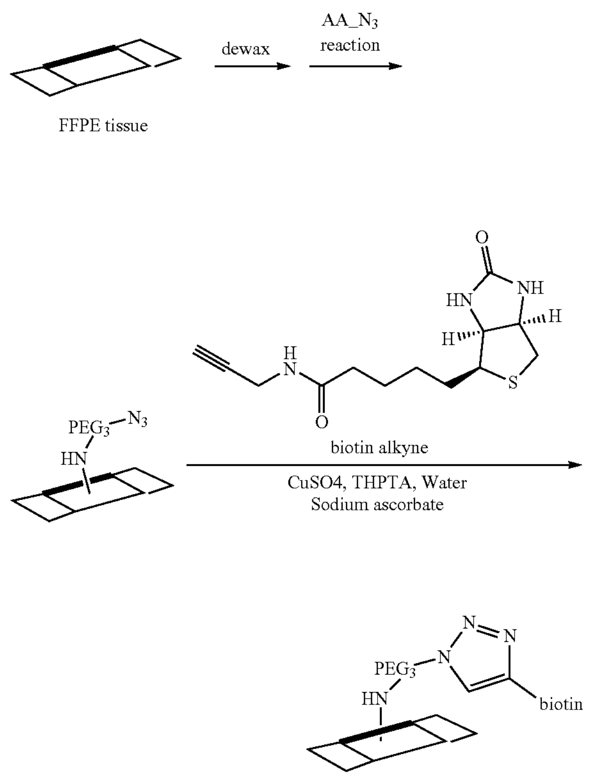

TABLE 15

Click reaction mixture for AA_$N_3$ treated slide

| | | MW | Reagent [C] | Reagents Stock Sln. [C] | Reagent stock Sln. prep. Per 1 mL water | Volume of stock sln. added |
|---|---|---|---|---|---|---|
| A | biotin-alkyne | 281.12 | 1.0 mM | 25 mM | 7.0 mg DMSO/Water 1/1 (1 mL) | 20 μL |
| B | $CuSO_4$ | 159.61 | 0.1 mM | 20 mM | 3.19 mg | 2.5 μL |
| C | sodium ascorbate | 198.11 | 5 mM | 100 mM | 20 mg | 25 μL |
| D | THPTA | 434.5 | 0.5 mM | 50 mM | 21.725 mg | 5 μL |
| E | aminioguanidine HCl | 110.55 | 5 mM | 100 mM | 11 mg | 25 μL |
| F | 10xPBS | | | | | 422.5 μL |
| | Overall volume | | | | | 500 μL |

Mix B and D in an Eppendorf tube. Add A and F into another Eppendorf tube. Sequentially add B&D mixture, E and C into the A&F mixture. Reagent A, B, D, E and F could be prepared as a stock solution. Sodium ascorbate solution (C) needs to be prepared fresh.

CuAAC on AA_XL Slides

FFPE tissue slide was dewaxed, subjected to AA_XL reaction and washes (Scheme 16). The CuAAC setup and washes are the same as described in the section tilled "CuAAC on AA_$N_3$ slides" of this Example. The only difference is that CuAAC for AA_XL mixture was prepared as described in Table 12.

Scheme 16

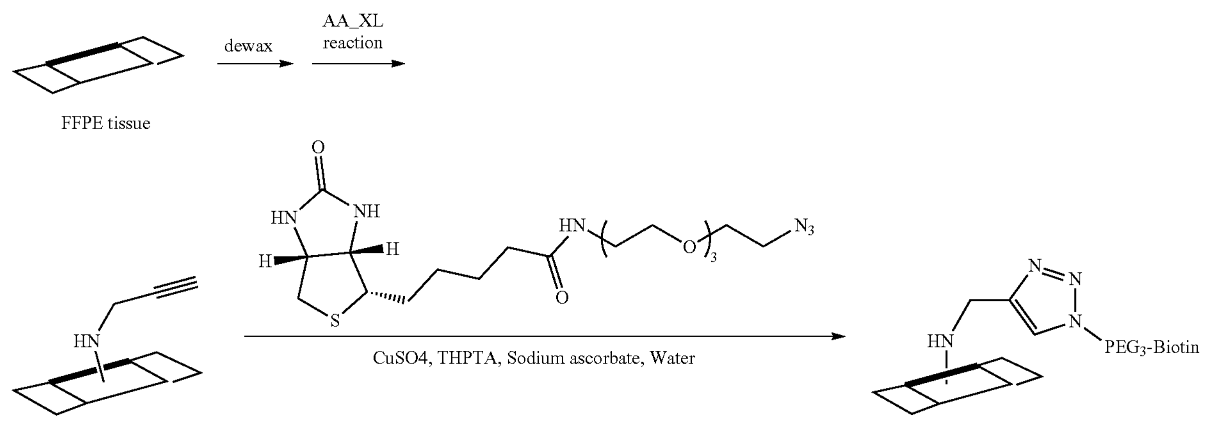

Immunohistochemical (IHC) Staining for AA_N3 CuAAc Treated FFPE Slides.

Before IHC staining, slide A, its catalyst free control slide B, and sialic acid free control slide C are prepared as following: As for slide A, dewaxed FFPE tissue slide was subject to AA_$N_3$ protocol (described in section titled "AA protocol and AA_$N_3$ protocol" in this Example), CuAAC protocol (described in the section titled "Four slides AA_XL, AA, only the washes, dewax comparison" of this Example) and HIER (pH6, described in the section titled "Four slides AA_XL, AA, only the washes, dewax comparison" of this Example). Compare to slide A, the only difference in slide B is that catalyst free CuAAC was performed (as described in described in section titled "AA protocol and AA_$N_3$ protocol" in this Example). Compare to slide A, sialidase treated FFPE slide (described in the section titled "AA_XL on FFPE slides for MALDI IMS" of this Example) was used in slide C, and no more HIER was performed after CuAAC. Three slides were then subject to IHC staining together. Reagents in Horseradish peroxidase-3,3'-diaminobenzidine (HRP-DAB) staining kits (R&D Systems) were used except for the protein blocking step. Tissue slide was placed inside humidity chamber (described in 4.5) face up. Incubation solution (200 room temperature) was applied for each step, and tissue was covered by cover glass (new for each step). Incubations are at room temperature. Washing setup is described in the section titled "AA_XL on FFPE slides for MALDI IMS" of this Example. Incubation and washing steps are as following: slides were incubated with peroxidase blocking solution (R&D kit) for 30 min and washed with PBS (5 min×3). Slides were then incubated with protein blocking reagent (Odyssey, LI-COR) for 30 min. Incubation solution was aspirated. Slides were incubated with HSS-HRP (R&D kit) for 30 min and washed with PBS (5 min×4). Slides were incubated with DAB solution (R&D system, 1 drop DAB Chromogen in 1 mL buffer, mixed thoroughly, filtered through PTFE filter if necessary) for 15 min and washed with DI water (5 min×2). Right after the washing, slides were incubated in Mayer's hematoxylin solution (1 min), washed with water (1 min×3), and sequentially incubated in 70% EtOH in water (1 min), 100% EtOH (15 sec), 2% ammonia in water (10 sec), 70% EtOH in water (1 min), 95% EtOH in water (1 min), 100% EtOH (1 min×2) and xylene (3 min×2). Slides were dried in hood for 10 min. Cytoseal XYL (2 to about 4 drops, ThermoFisher) was applied onto the tissue and cover glass was placed. Slide was dried overnight, and extra gel was removed by dipping into xylene. Slides was imaged in a Nanozoomer 2.0RS (Hamamatsu, Hamamatsu-city, Japan).

Tissue Lysate Preparation and Western Blotting

Before tissue lysate extraction, slide A, its catalyst free control slide B, sialic acid free control slide C and only dewaxed slide D were prepared as following: As for slide A, dewaxed FFPE tissue slide was subject to AA_$N_3$ protocol (described in section titled "AA protocol and AA_$N_3$ protocol" in this Example), CuAAC protocol ((described in the section titled "Four slides AA_XL, AA, only the washes, dewax comparison" of this Example). Compare to slide A, the only difference in slide B is that catalyst free CuAAC was performed (as described in 4.6). Compare to slide A, sialidase treated FFPE slide (described in the section titled "Sialidase treated FFPE slides" of this Example) was used in slide C. Slide D was only dewaxed with no further protocol. Slides A~D was then subject to same tissue lysate extraction protocols[11]. Tissue was removed with clean blazer, transferred into Eppendorf tube and weighed. Tissue pellets were homogenized using a probe sonicator (Fisher Scientific FB120, 20% amp, 30 sec) in 100 volumes of protein extraction buffer (300 mM Tris-HCl pH 8.0 and 2% SDS). Samples were incubated at 90° C. for 120 min. The extracts were centrifuged for 20 min at 16,000×g at 4° C. Supernatant A~D was kept in 4° C. The concentration of the supernatant was normalized with silver stain (SilverQuest silver staining kit; Invitrogen). Around the same amount of lysate A~D was mixed with loading buffer (Bolt LDS loading buffer, non-reductive), heated (70° C., 10 min) and loaded to SDS-Page (Bolt 4-12% Bis-Tris Plus gel; Invitrogen) well 3~6 and as a duplication in well 10~13. Protein ladder (5 μL, SeeBlue; Invitrogen) was loaded on well 2&9. Protein ladder (1 μL, BenchMark; Invitrogen) was loaded on well 8&15. Biotinylated Aleuria Aurantia Lectin (0.03 μg b-AAL, Vector) was loaded on well 14. b-AAL (0.06 μg) was loaded on well 8. Gel was developed with MOPS SDS running buffer (Bolt; Invitrogen) at r.t. ~100 V and transferred to nitrocellulose membrane (LI-COR, pore size 0.2 μm) in transfer buffer (Bolt; Invitrogen) at ~160 mA for 4 hr 45 min in an ice-water bath. Membrane was blotted and scanned as described in the section titled "SDS Page and western blotting" of this Example.

Results

Table 16 shows m/z values of N-linked glycans presented in the four slides comparison study.

TABLE 16

| Observed Mass | Theoretical Mass | Error in PPM | ±[Da] | ±PPM | Glycan Structure |
|---|---|---|---|---|---|
| 1589.5221 | 1589.5446 | −14.1550 | 0.1670 | 105.0615 | Hex4HexNAc3NeuAc1 |
| 1616.5918 | 1616.5919 | −0.0619 | 0.0810 | 50.1054 | Hex4HexNAc3NeuAc1 + 27 |
| 1626.5490 | 1626.5762 | −16.7222 | 0.0970 | 59.6345 | Hex4HexNAc3NeuAc1 + 37 |
| 1735.6163 | 1735.6025 | 7.9511 | 0.1880 | 108.3197 | Hex4HexNAc3NeuAc1dHex1 |
| 1762.6376 | 1762.6498 | −6.9214 | 0.0880 | 49.9248 | Hex4HexNAc3NeuAc1dHex1 + 27 |
| 1772.6377 | 1772.6341 | 2.0309 | 0.0890 | 50.2078 | Hex4HexNAc3NeuAc1dHex1 + 37 |
| 1792.6317 | 1792.6240 | 4.2954 | 0.1100 | 61.3626 | Hex4HexNAc4NeuAc1 |
| 1819.6719 | 1819.6713 | 0.3297 | 0.2070 | 113.7568 | Hex4HexNAc4NeuAc1 + 27 |
| 1829.6462 | 1829.6556 | −5.1376 | 0.1790 | 97.8326 | Hex4HexNAc4NeuAc1 + 37 |
| 1954.6516 | 1954.6768 | −12.8922 | 0.1420 | 72.6463 | Hex5HexNAc4NeuAc1 |
| 1981.7244 | 1981.7241 | 0.1514 | 0.0990 | 49.9565 | Hex5HexNAc4NeuAc1 + 27 |
| 1991.7143 | 1991.7084 | 2.9623 | 0.1000 | 50.2082 | Hex5HexNAc4NeuAc1 + 37 |
| 2100.7425 | 2100.7347 | 3.7130 | 0.1050 | 49.9825 | Hex5HexNAc4NeuAc1dHex1 |
| 2127.7805 | 2127.7820 | −0.7050 | 0.1060 | 49.8171 | Hex5HexNAc4NeuAc1dHex1 + 27 |
| 2137.7662 | 2137.7663 | −0.0468 | 0.1070 | 50.0522 | Hex5HexNAc4NeuAc1dHex1 + 37 |
| 2272.7946 | 2272.8195 | −10.9556 | 0.1960 | 86.2365 | Hex5HexNAc4NeuAc2 + 27 |
| 2294.7866 | 2294.8015 | −6.4929 | 0.1380 | 60.1359 | Hex5HexNAc4NeuAc2 + Na + 27 |
| 2299.8686 | 2299.8668 | 0.7827 | 0.1150 | 50.0029 | Hex5HexNAc4NeuAc2 + 27*2 |
| 2418.8749 | 2418.8774 | −1.0335 | 0.1210 | 50.0232 | Hex5dHexlHexNAc4NeuAc2 + 27 |
| 2440.8607 | 2440.8594 | 0.5326 | 0.1220 | 49.9824 | Hex5dHexlHexNAc4NeuAc2 + Na + 27 |
| 2428.8676 | 2428.8617 | 2.4291 | 0.1210 | 49.8176 | Hex5dHex1HexNAc4NeuAc2 + 37 |
| 2450.8527 | 2450.8437 | 3.6722 | 0.1230 | 50.1868 | Hex5dHex1HexNAc4NeuAc2 + Na + 37 |
| 2168.7651 | 2168.8086 | −20.0571 | 0.2050 | 94.5219 | Hex4HexNAc5NeuAc1dHex1 + 27 |
| 2178.7628 | 2178.7929 | −13.8150 | 0.1240 | 56.9122 | Hex4HexNAc5NeuAc1dHex1 + 37 |
| 2303.8435 | 2303.8141 | 12.7614 | 0.1150 | 49.9172 | Hex51HexNAc5NeuAc1dHex1 |
| 2330.8650 | 2330.8614 | 1.5445 | 0.1890 | 81.0859 | Hex51HexNAc5NeuAc1dHex1 + 27 |
| 2340.8363 | 2340.8457 | −4.0156 | 0.1170 | 49.9819 | Hex51HexNAc5NeuAc1dHex1 + 37 |
| 2465.8870 | 2465.8669 | 8.1513 | 0.1230 | 49.8810 | Hex6HexNAc5NeuAc1dHex1 |
| 2492.9135 | 2492.9142 | −0.2808 | 0.1250 | 50.1421 | Hex6HexNAc5NeuAc1dHex1 + 27 |
| 2502.9043 | 2502.8985 | 2.3173 | 0.1250 | 49.9421 | Hex6HexNAc5NeuAc1dHex1 + 37 |

Figure 2:
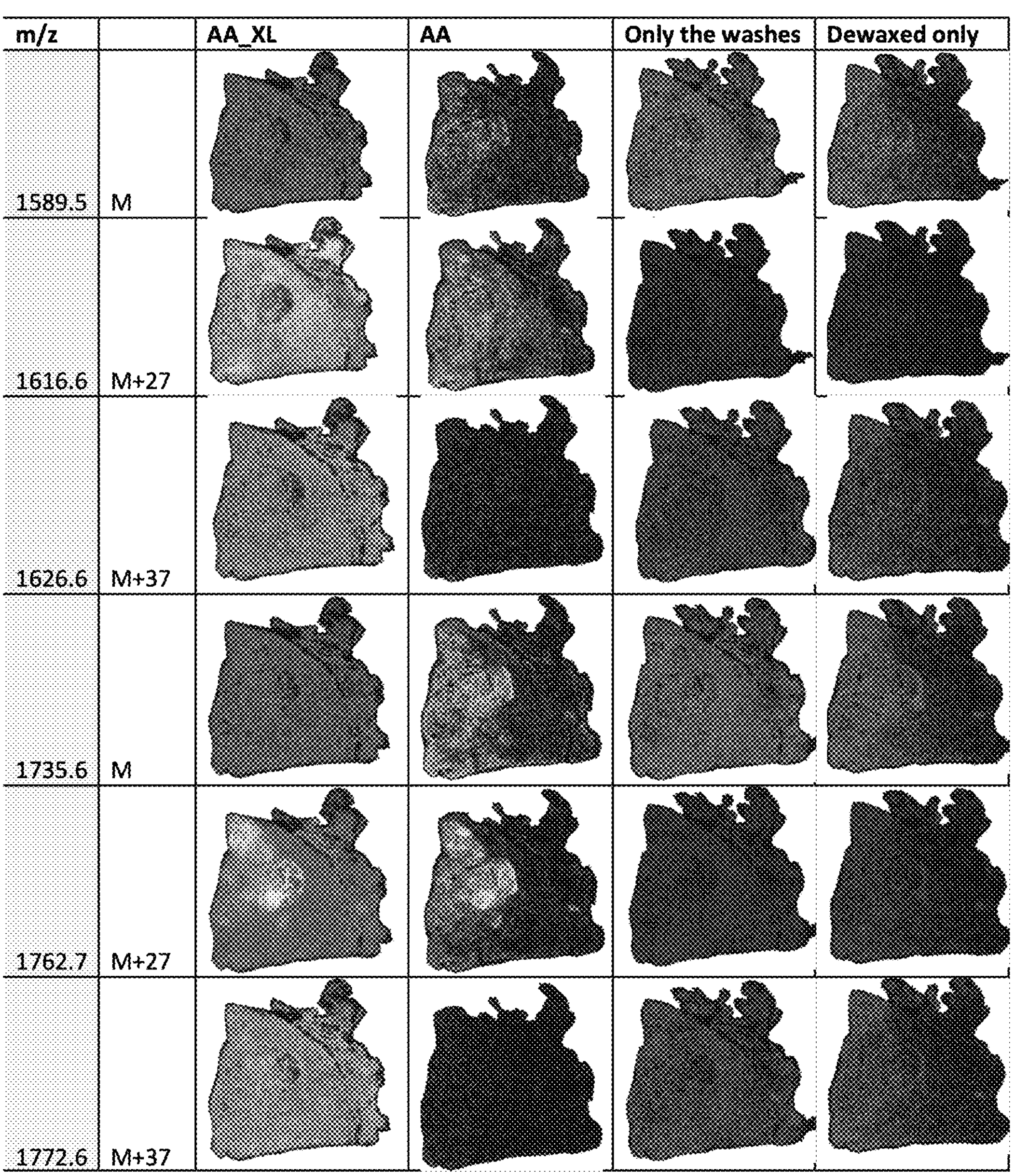
FIG. 2 shows a table presenting MALDI IMS data from a comparison study of four slides prepared using different conditions/methods (AA_XL, AA, washes only, and dewaxed only).

FIG. 2 shows a table presenting MALDI IMS data from a comparison study of four slides prepared using different conditions/methods (AA_XL, AA, washes only, and dewaxed only).

FIG. 5 shows a western blot analysis for mixture 20 and 19. 3'sialyllactose-BSA were subject to AA_XL and CuAAC with biotin azide as described in Scheme 2 to yield mixture 20. With the same protocol, 6'sialyllactose-BSA was converted to mixture 19. Gel (loaded with ladder, mixture 20, mixture 19 and biotin-AAL) was developed and transferred. Membrane was blotted with streptavidin-IR800 and scanned with LI-COR.

Figure 6:
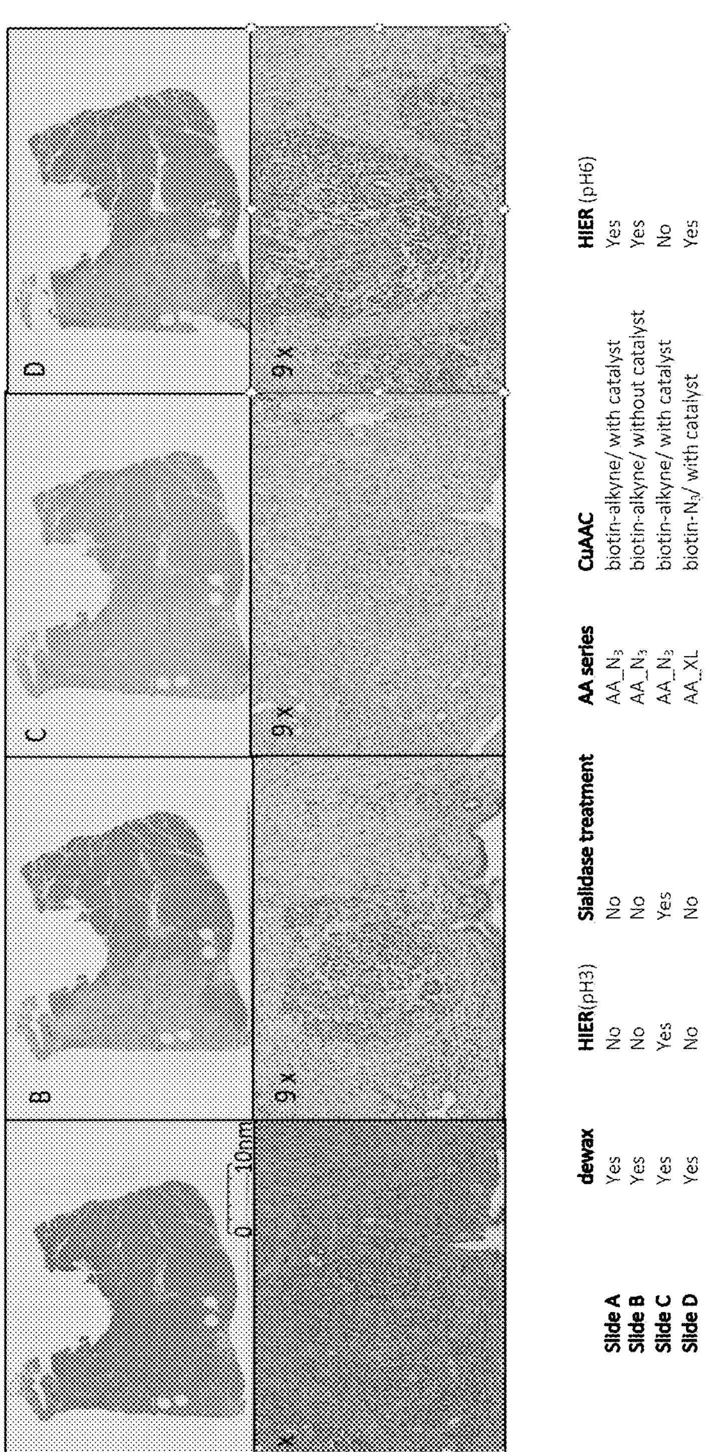
FIG. 6 shows IHC staining of various slides A-D AA_$N_3$_CuAAC treated slide A, its catalyst free control B, its sialic acid free control C, and AA_XL_CuAAC treated slide D. Preparation of slides A to D was described in the table. All four slides then were subjected to IHC staining with HRP-DAB kit, stained with hematoxylin, mounted with Cytoseal and scanned by Nanozoomer.

FIG. 6 shows IHC staining of various slides A-D $AA\_N_3\_CuAAC$ treated slide A, its catalyst free control B, its sialic acid free control C, and AA_XL_CuAAC treated slide D. Preparation of slides A to D was described in the table. All four slides then went through IHC staining with HRP-DAB kit, stained with hematoxylin, mounted with Cytoseal and scanned by Nanozoomer.

CuAAC on slides are two-phase reaction. Sialic acid on FFPE tissue is on the solid phase, and CuAAC reagents in aqueous solution are on liquid phase. In $AA\_N_3$ treated slide, $NH_2$-$PEG_3$-$N_3$ was installed onto sialic acid. $PEG_3$ makes azide more approachable for CuAAC reagent in aqueous solution, hence lead to higher reaction yield. While, in AA_XL treated slide, $NH_2$—$CH_2$-alkyne is too hydrophobic to be approached by CuAAC reagents in aqueous solution, hence lead to lower reaction yield. Therefore, $AA\_N_3\_CuAAC$ treated slide A stains much stronger than AA_XL_CuAAC treated slide D.

Figure 7:
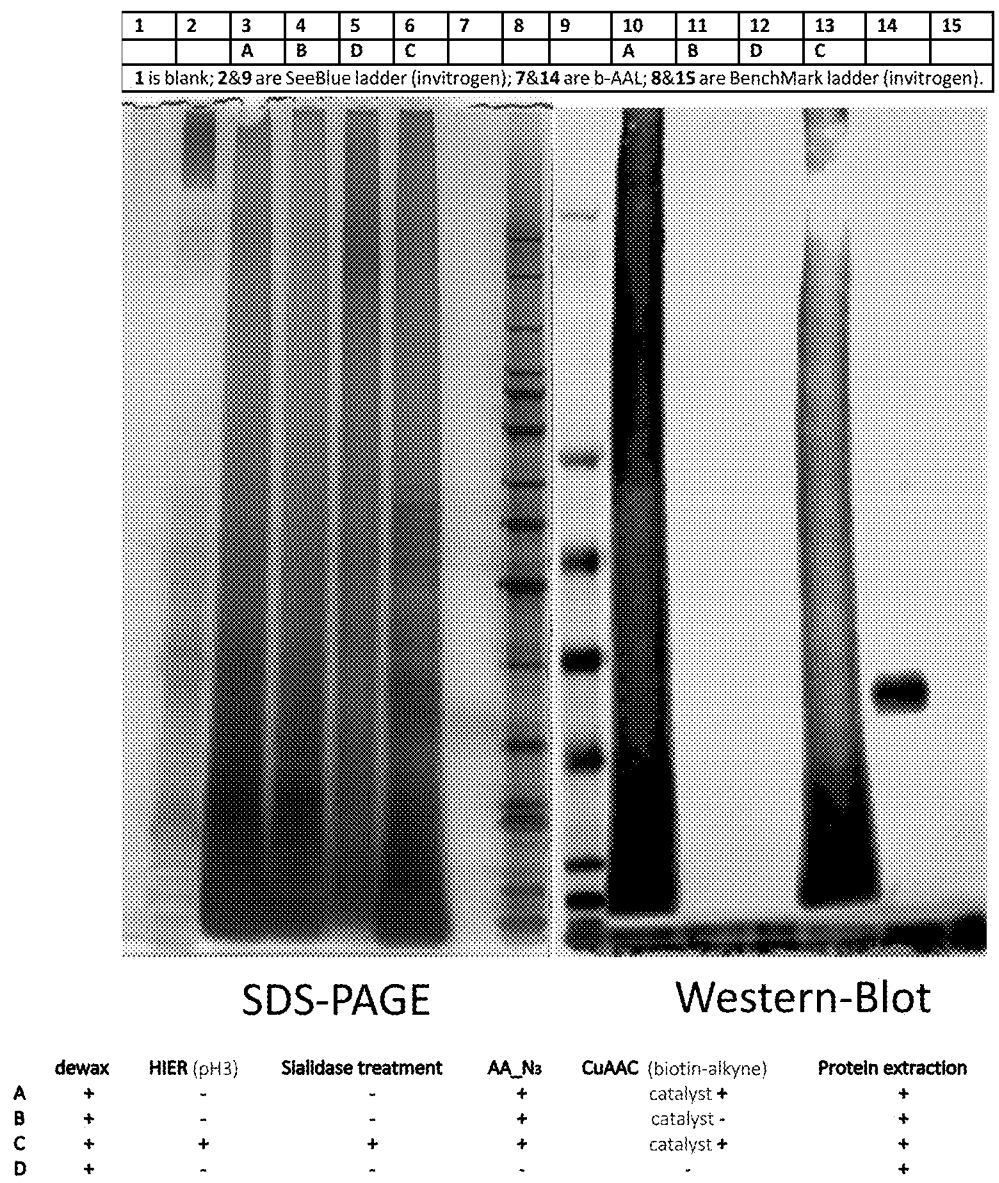
FIG. 7 shows SDS-PAGE and Western blotting for tissue lysates.

FIG. 7 shows SDS-PAGE and Western blotting for tissue lysates. Slides A to D were prepared as described in the above table. Tissue pallets were prepared and extracted with 300 mM Tris-HCl buffer (pH8.0, with 2% SDS, 100 volume). The concentration of the tissue lysate was normalized with silver stain. Protein ladders, b-AAL (positive control) and lysate (A to D) were loaded on gel (well 2 to 8), with well 9 to 15 as duplication. After development, half the gel was silver stained. The other half was transferred to membrane and blotted with streptavidin-IR800. Blotted membrane was scanned with LI-COR.

References for Example 10

1. Zeng, Y.; Ramya, T. N. C.; Dirksen, A.; Dawson, P. E.; Paulson, J. C., High-efficiency labeling of sialylated glycoproteins on living cells. *Nat Meth* 2009, 6 (3), 207-209.
2. Saludes, J. P.; Ames, J. B.; Gervay-Hague, J., Synthesis and Structural Characterization of Sialic Acid-Glutamic Acid Hybrid Foldamers as Conformational Surrogates of α-2,8-Linked Polysialic Acid. *Journal of the American Chemical Society* 2009, 131 (15), 5495-5505.
3. Lifely, M. R.; Gilbert, A. S.; Moreno, C., Sialic acid polysaccharide antigens of *Neisseria meningitidis* and *Escherichia coli*: Esterification between adjacent residues. *Carbohydrate Research* 1981, 94 (2), 193-203.
4. Flaherty, T. M.; Gervay, J., 2D NMR analysis of the polylactone derivative of colominic acid. Complete 1H and 13C NMR chemical shift assignments. *Carbohydr. Res.* 1996, 281 (1), 173-7.
5. Su, Y.; Kasper, C.; Kirschning, A.; Drager, G.; Berski, S., Synthesis of New Polysialic Acid Derivatives. *Macromolecular Bioscience* 2010, 10 (9), 1028-1033.
6. Presolski, S. I.; Hong, V. P.; Finn, M. G., Copper-Catalyzed Azide-Alkyne Click Chemistry for Bioconjugation. *Current protocols in chemical biology* 2011, 3 (4), 153-162.
7. Powers, T. W.; Neely, B. A.; Shao, Y.; Tang, H.; Troyer, D. A.; Mehta, A. S.; Haab, B. B.; Drake, R. R., MALDI imaging mass spectrometry profiling of N-glycans in formalin-fixed paraffin embedded clinical tissue blocks and tissue microarrays. *PLoS One* 2014, 9 (9), e106255-e106255.

8. Angel, P. M.; Mehta, A.; Norris-Caneda, K.; Drake, R. R., MALDI Imaging Mass Spectrometry of N-glycans and Tryptic Peptides from the Same Formalin-Fixed, Paraffin-Embedded Tissue Section. *Methods Mol Biol* 2018, 1788, 225-241.

9. Angel, P. M.; Comte-Walters, S.; Ball, L. E.; Talbot, K.; Mehta, A.; Brockbank, K. G. M.; Drake, R. R., Mapping Extracellular Matrix Proteins in Formalin-Fixed, Paraffin-Embedded Tissues by MALDI Imaging Mass Spectrometry. *J Proteome Res* 2018, 17 (1), 635-646.

10. McDowell, C. T.; Klamer, Z.; Hall, J.; West, C. A.; Wisniewski, L.; Powers, T. W.; Angel, P.; Mehta, A. S.; Lewin, D. N.; Haab, B.; Drake, R., Imaging Mass Spectrometry and Lectin Analysis of N-linked Glycans in Carbohydrate Antigen Defined Pancreatic Cancer Tissues. *Molecular & amp; Cellular Proteomics* 2020, mcp.RA120.002256.

11. Kawashima, Y; Kodera, Y.; Singh, A.; Matsumoto, M.; Matsumoto, H., Efficient extraction of proteins from formalin-fixed paraffin-embedded tissues requires higher concentration of tris(hydroxymethyl)aminomethane. *Clinical Proteomics* 2014, 11 (1), 4.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. An assay to spatially resolve 2,3 linked N-glycans, 2,6 linked N-glycans, and 2,8 linked N-glycans in situ or ex vivo comprising:

exposing, in situ or ex vivo, a cell or cell population, a tissue, or the component thereof to reagents that selectively modify 2,3 linked, 2,6 linked, or a 2,8 linked sialic acids or polysialic acid present on N-glycans of the cell or cell population, tissue, or component thereof, thereby generating a selectively modified 2,3, linked, 2,6, linked, or a 2,8 linked sialic acids or polysialic acids in the cell or cell population, the tissue, or the component thereof, wherein the selectively modified 2,3 linked or the 2,8 linked sialic acids or polysialic acids are selectively modified at the 2 position by attachment of a bifunctional linker via a lactone intermediate of the 2,3 linked or the 2,8 linked sialic acids or polysialic acids, and wherein the selectively modified 2,6 linked sialic acids are modified at the 2-position by attachment of a bifunctional linker by direct amidation, wherein the bifunctional linker comprises a primary amine and a reactive functionality and wherein the selectively modified 2,3 linked, 2,6 linked, or 2,8 linked sialic acid or polysialic acid further comprises a cargo molecule, wherein the cargo molecule is attached to the bifunctional linker, the bifunctional linker and cargo molecule together introducing a linkage specific defined mass modification;

detecting, quantifying, or both one or more characteristics of the cell or cell population, tissue, or component thereof by mass spectrometry imaging of spatial distributions of the selectively modified 2,3 linked, 2,6 linked, or the 2,8 linked sialic acid or polysialic acid, and wherein the assay spatially resolves the 2,3 linked, 2,6 linked, and 2,8 linked sialic acids based on different mass modifications introduced by the linkage specific bifunctional linker and cargo molecule.

2. The assay of claim 1, wherein attaching the bifunctional linker to the lactone intermediate comprises exposing the 2,3 linked, or the 2,8 linked sialic acid or polysialic acid to a condensing reagent under suitable reaction conditions to form a lactone at the 2,3 or 2,8 linkages so as to form the lactone intermediate of the 2,3 linked, or the 2,8 linked sialic acid or polysialic acid; and exposing the lactone intermediate to a bifunctional linker comprising the reactive functionality with a primary amine under suitable reaction conditions to selectively attach the bifunctional linker to the 2 position of the 2,3 linked, or 2,8 linked sialic acid or polysialic acid thereby selectively modifying the 2,3 linked, or 2,8 linked sialic acid or polysialic acid with the bi-functional linker.

3. The assay of claim 1, wherein the cargo molecule is attached to the bifunctional linker by exposing bifunctional linker with a reactive cargo molecule whereby the reactive cargo molecule reacts with an available reactive functionality on the bifunctional linker to attach the cargo molecule to the bifunctional linker so as to selectively attach the cargo molecule to the 2,3 linked, 2, 6 linked, or 2,8 linked sialic acid or polysialic acid.

4. The assay of claim 1, wherein the bifunctional linker is or comprises a propargyl amine or an azide amine, whereby the resulting selectively modified 2,3 linked, 2, 6 linked, or 2,8 linked sialic acid or polysialic acid is modified to contain a reactive alkyne, a reactive azide, or both.

5. The assay of claim 1, wherein the selectively modified 2,3 linked, 2, 6 linked, or 2,8 sialic acid or polysialic acid is attached to or is otherwise incorporated with a biological molecule.

6. The assay of claim 2, wherein the selectively modified 2,3 linked or 2,8 linked sialic acid or polysialic acid is attached to or otherwise incorporated with a biological molecule before exposing the 2,3 linked, or 2,8 linked sialic acid or polysialic acid to the condensing reagent, exposing the lactone intermediate to a bifunctional linker, or both.

7. The assay of claim 2, wherein the 2,3 linked or 2,8 linked sialic acid or polysialic acid is attached to or otherwise incorporated with a biological molecule after exposing the 2,3 linked, or 2,8 linked sialic acid or polysialic acid to a dimethyl amine, exposing the lactone to a bifunctional linker, or both.

8. The assay of claim 5, wherein the biologic molecule is a protein.

9. The assay of claim 8, wherein the protein is an antibody.

10. The assay of claim 5, wherein the biologic molecule is (a) integrated into or is otherwise part of or coupled to one or more components of a cell; or (b) is integrated into, is otherwise part of, or is coupled to one or more components of a micelle, exosome, or other vesicle.

11. The assay of claim 1, wherein the bifunctional linker is selected from the group consisting of: Azido-PEG4-Amine, azido-propylamine, methyltetrazine amine, methyltetrazine-$PEG_4$-amine, Azido-PEG3-Amine, Biotin-PEG3-amine, isotope-targeted glycoproteomic biotin amine, Desthiobiotin-linker-amine, DBCO-linker-amine, FITC-linker-amine, CHCA-linker-amine, DHB-linker-amine, biotin-linker-amine, azido-linker-amine, and an alkyne-linker-amine.

12. The assay of claim 1, wherein the cargo molecule is a mass spectrometry matrix molecule, an imaging agent, a therapeutic agent, a biologically active agent, or any combination thereof.

13. The assay of claim 1, wherein the cell or cell population, the tissue, or the component thereof is/are fixed in formalin.

14. The assay of claim 1, wherein the one or more characteristics of the cell or cell population, the tissue, or the component thereof detected, quantified, or both is gene expression, protein expression, metabolites, growth, protein modification, cell or tissues composition, and combinations thereof.

15. The assay of claim 1, wherein detecting, quantifying, or both comprises mass spectrometry, a cell or tissue staining technique, an affinity detection technique, an immunodetection technique, sequencing, a cell or tissue imaging technique, or any combination thereof.

16. The assay of claim 1, wherein the selectively modified 2,3, linked, 2,6, linked, or a 2,8 linked sialic acids or polysialic acids are present in a cell membrane or extracellular matrix.

17. The assay of claim 1, wherein the selectively modified 2,3, linked, 2,6, linked, or a 2,8 linked sialic acids or polysialic acids are present in a glycoprotein or a glycolipid.

18. The assay of claim 1, wherein the cargo molecule generates or enhances a detectable signal for mass spectrometry analysis.

* * * * *